(12) United States Patent
Haseba et al.

(10) Patent No.: US 9,593,094 B2
(45) Date of Patent: Mar. 14, 2017

(54) LIQUID CRYSTAL MEDIUM, OPTICAL DEVICE, AND LIQUID CRYSTAL COMPOUND

(71) Applicants: JNC CORPORATION, Tokyo (JP); JNC PETROCHEMICAL CORPORATION, Tokyo (JP)

(72) Inventors: Yasuhiro Haseba, Chiba (JP); Koki Sago, Chiba (JP); Shinichi Yamamoto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/791,267

(22) Filed: Jul. 3, 2015

(65) Prior Publication Data
US 2016/0002536 A1  Jan. 7, 2016

(30) Foreign Application Priority Data
Jul. 3, 2014 (JP) .................. 2014-137672

(51) Int. Cl.
| | | |
|---|---|---|
| G02F 1/1333 | (2006.01) | |
| C07D 319/06 | (2006.01) | |
| C09K 19/58 | (2006.01) | |
| C09K 19/30 | (2006.01) | |
| C09K 19/34 | (2006.01) | |
| C09K 19/04 | (2006.01) | |

(52) U.S. Cl.
CPC ........ *C07D 319/06* (2013.01); *C09K 19/3066* (2013.01); *C09K 19/3458* (2013.01); *C09K 19/586* (2013.01); *C09K 2019/0448* (2013.01); *C09K 2019/0466* (2013.01); *C09K 2019/3422* (2013.01)

(58) Field of Classification Search
CPC .............. C09K 19/586; C09K 19/3066; C09K 19/3458; C09K 2019/3422; C09K 2019/0448; C09K 2019/0466; G02F 1/1333; C07D 319/06
USPC ............. 252/299.01, 299.6, 299.63; 349/182
See application file for complete search history.

(56) References Cited

U.S. PATENT DOCUMENTS

| | | | |
|---|---|---|---|
| 5,728,319 A | 3/1998 | Matsui et al. | |
| 5,858,272 A | 1/1999 | Haseba et al. | |
| 8,858,830 B2* | 10/2014 | Yamamoto | C09K 19/3402 252/299.01 |
| 9,175,222 B2* | 11/2015 | Sago | C09K 19/3402 |
| 2006/0006363 A1 | 1/2006 | Heckmeier et al. | |
| 2006/0050354 A1 | 3/2006 | Heckmeier et al. | |
| 2006/0227283 A1 | 10/2006 | Ooi et al. | |
| 2008/0259254 A1 | 10/2008 | Kikuchi et al. | |
| 2009/0135368 A1 | 5/2009 | Haseba et al. | |
| 2011/0242473 A1 | 10/2011 | Haseba et al. | |
| 2011/0253935 A1 | 10/2011 | Jansen et al. | |
| 2012/0099039 A1 | 4/2012 | Haseba et al. | |
| 2013/0135544 A1* | 5/2013 | Yamamoto | C09K 19/3402 349/33 |
| 2013/0306908 A1 | 11/2013 | Jansen et al. | |

(Continued)

FOREIGN PATENT DOCUMENTS

| | | |
|---|---|---|
| EP | 959060 | 11/1999 |
| EP | 1824946 | 8/2007 |

(Continued)

OTHER PUBLICATIONS

Hirotsugu Kikuchi, Masayuki Yokota, Yoshiaki Hisakado, Huai Yang and Tisato Kajiyama, "Polymer-stabilized liquid crystal blue phases", Nature Materials, Sep. 2, 2002, p. 64-p. 68, vol. 1, Nature Publishing Group.
Yoshiaki Hisakado, Hirotsugu Kikuchi, Toshihiko Nagamura and Tisato Kajiyama, "Large Electro-optic Kerr Effect in Polymer-Stabilized Liquid-Crystalline Blue Phases", Advanced Materials, Jan. 6, 2005, p. 96-p. 98, vol. 17, Wiley-VCH Verlag Gmbh & Co.
Yasuhiro Haseba and Hirotsugu Kikuchi, "Electro-optic effects of the optically isotropic state induced by the incorporative effects of a polymer network and the chirality of liquid crystal", Journal of the SID, Jun. 14, 2006, p. 551-p. 556, Society for Information Display.

*Primary Examiner* — Geraldina Visconti
(74) *Attorney, Agent, or Firm* — Jianq Chyun IP Office

(57) ABSTRACT

A liquid crystal medium having stability to heat, light and so forth, a wide liquid crystal phase temperature range, a low driving voltage and a small permittivity and exhibiting an optically isotropic liquid crystal phase is described. An optical device or the like having a short response time, a large contrast ratio, a low driving voltage and a small permittivity is also described. The liquid crystal composition contains an achiral component (T) and a chiral agent, and exhibits an optically isotropic liquid crystal phase. The achiral component (T) includes at least one compound represented by formula (1):

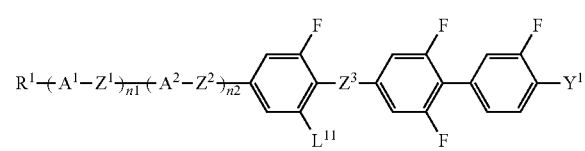

(1)

wherein, for example, $R^1$ is alkyl having 1 to 12 carbons, $A^1$ and $A^2$ are 1,4-phenylene, $Z^1$ and $Z^2$ are single bonds, $Z^3$ is —COO— or —$CF_2O$—, $L^{11}$ is hydrogen, fluorine or chlorine, $Y^1$ is fluorine, chlorine, —$CF_3$ or —$OCF_3$, n1 and n2 are each independently 0 or 1, and $n1+n2 \geq 1$.

15 Claims, 1 Drawing Sheet

(56) References Cited

U.S. PATENT DOCUMENTS

| | | | |
|---|---|---|---|
| 2014/0132868 A1* | 5/2014 | Sago | C09K 19/3402 349/42 |
| 2015/0240159 A1* | 8/2015 | Yamamoto | C09K 19/20 349/86 |

FOREIGN PATENT DOCUMENTS

| | | |
|---|---|---|
| EP | 1690917 | 10/2008 |
| EP | 2838975 | 2/2015 |
| JP | 07-509025 | 10/1995 |
| JP | 10-081679 | 3/1998 |
| JP | 2003-327966 | 11/2003 |
| JP | 2005-157109 | 6/2005 |
| JP | 2005-336477 | 12/2005 |
| JP | 2006-506477 | 2/2006 |
| JP | 2006-506515 | 2/2006 |
| JP | 2006-089622 | 4/2006 |
| JP | 2006-127707 | 5/2006 |
| JP | 2006-225655 | 8/2006 |
| JP | 2006-299084 | 11/2006 |
| JP | 2009-144135 | 7/2009 |
| JP | 2011-225566 | 11/2011 |
| WO | 9611897 | 4/1996 |
| WO | 9823561 | 6/1998 |
| WO | 2005080529 | 9/2005 |
| WO | 2005090520 | 9/2005 |
| WO | 2006063662 | 6/2006 |
| WO | 2010058681 | 5/2010 |
| WO | 2010134430 | 11/2010 |
| WO | 2012100809 | 8/2012 |
| WO | 2013080724 | 6/2013 |
| WO | 2013156113 | 10/2013 |

* cited by examiner

Optical system for measurement
(using a comb-electrode cell)

LIQUID CRYSTAL MEDIUM, OPTICAL DEVICE, AND LIQUID CRYSTAL COMPOUND

CROSS-REFERENCE TO RELATED APPLICATION

This application claims the priority benefits of Japan application no. 2014-137672, filed on Jul. 3, 2014. The entirety of the above-mentioned patent application is hereby incorporated by reference herein and made a part of this specification.

TECHNICAL FIELD

The invention relates to a liquid crystal compound useful as a material for, e.g., an optical device, a liquid crystal composition, an optical device using the liquid crystal composition, and so forth.

BACKGROUND ART

Liquid-crystal display devices using liquid crystal compositions are widely utilized in displays such as clocks, electronic calculators, mobile phones, personal computers, televisions and so forth. These liquid-crystal display devices utilize refractive index anisotropy, dielectric anisotropy or the like of liquid crystal compounds. As an operating mode in the liquid-crystal display device, twisted nematic (TN), super twisted nematic (STN), bistable twisted nematic (BTN), electrically controlled birefringence (ECB), optically compensated bend (OCB), in-plane switching (IPS), vertical alignment (VA) and so on that perform display mainly using one or more polarizers have been known. Further, a mode that exhibits electric birefringence by applying an electric field in an optically isotropic liquid crystal phase has also been studied in recent years (Patent Literatures 1 to 13 and Non-patent Literatures 1 to 3).

Further, a wavelength variable filter, a wavefront control element, a liquid crystal lens, an aberration correction element, an aperture control element, an optical head device and so forth using the electric birefringence in a blue phase as one of the optically isotropic liquid crystal phases have been proposed (Patent Literatures 10 to 12).

A classification based on the driving mode of the element includes the passive matrix (PM) type and the active matrix (AM) type. The PM type is classified into the static type, the multiplex type and so on. The AM type is classified into the thin-film transistor (TFT) type, the metal insulator metal (MIM) type and so on according to the type of switching elements.

As the liquid crystal composition used in the LCD device, examples of optically isotropic liquid crystal compositions that contain a compound having two biphenylene groups and a difluoromethoxy linking group, or a tetracyclic compound having a dioxane ring are reported in Patent Literatures 14 to 24. These compounds have large dielectric anisotropy, and have an effect of reducing a driving voltage when used in a display device such as a display or the like.

However, in the mode that exhibits electric birefringence by applying an electric field in an optically isotropic liquid crystal phase, when a liquid crystal composition using the compound having a large dielectric anisotropy is used for reducing the driving voltage, the permittivity of the liquid crystal composition tends to increase.

For example, in a display mode using a polymer stabilized blue phase (PSBP) as a polymer/liquid-crystal composite material, when a polymer/liquid-crystal composite material having large permittivity is used in an optical device, the time for injecting charges into the thin film transistor (TFT) is increased, and problems such as increase in driving voltage, reduction in transmittance and so forth occur.

To solve such problems, a polymer/liquid-crystal composite material characterized by a low driving voltage and a low permittivity is demanded.

PRIOR-ART LITERATURES

Patent Literatures

1: JP2003-327966 A (Abstract)
2: WO2005/90520 A1=US20080259254 A1
3: JP2005-336477 A (Abstract)
4: JP2006-089622 A (Abstract)
5: JP2006-299084 A (Abstract)
6: JP2006-506477 A=US20060006363 A1
7: JP2006-506515 A=US20060050354 A1
8: WO2006/063662 A1=EP1824946 A 1
9: JP2006-225655 A=EP1690917 B1
10: JP2005-157109 A=US20060227283 A1
11: WO2005/80529 A1 (Abstract)
12: JP2006-127707 A (Abstract)
13: WO1998/023561 A1=EP959060 A1
14: WO2010/058681 A1=US20110242473 A1
15: WO96/11897 A1=U.S. Pat. No. 5,728,319 A
16: JP1998-081679=U.S. Pat. No. 5,858,272 A
17: JP2009-144135 A=US20090135368 A1
18: WO2010/058681 A1=US20110242473 A1
19: WO2010/134430 A1=US20120099039 A1
20: WO2013/080724 A1=US20130135544 A1
21: JPH07-509025 A (Abstract)
22: JP2011-225566 A=US20110253935 A1
23: WO2012/100809 A1=US20130306908 A1
24: WO2013/156113 A1=EP2838975 A1

Non-Patent Literatures

1: *Nature Materials*, 1, 64, (2002)
2: *Adv. Mater.*, 17, 96, (2005)
3: *Journal of the SID*, 14, 551, (2006)

SUMMARY OF THE INVENTION

Accordingly, a liquid crystal medium that has stability to heat, light and so on, a wide liquid crystal phase temperature range, a low driving voltage and small permittivity and exhibits an optically isotropic liquid crystal phase is required, and an optical device that can be used in a wide temperature range and has a short response time, a large contrast ratio, a low driving voltage and small permittivity is also required.

The invention provides, for example, a liquid crystal compound, a liquid crystal medium (a liquid crystal composition, a polymer/liquid-crystal composite material, or the like), a mixture of a polymerizable monomer and a liquid crystal composition, an optical device containing a liquid crystal medium and so on, a liquid crystal compound, and so on as follows.

The invention provides a compound, a liquid crystal medium (a liquid crystal composition or a polymer/liquid-crystal composite), an optical device containing a liquid crystal medium, and so on as follows. The invention includes the following items.

Item 1 is a liquid crystal composition that contains an achiral component (T) and a chiral agent and exhibits an optically isotropic liquid crystal phase, the achiral component (T) including, as a first component, at least one compound (1) represented by formula (1):

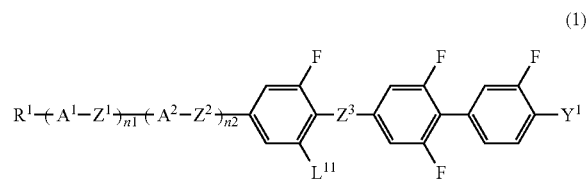
(1)

wherein $R^1$ is hydrogen, alkyl having 1 to 12 carbons, alkenyl having 2 to 12 carbons, alkynyl having 2 to 12 carbons, or alkoxy having 1 to 11 carbons; $A^1$ and $A^2$ are each independently 1,4-cyclohexylene, 1,3-dioxane-2,5-diyl, tetrahydropyran-2,5-diyl, 1,4-phenylene, 3-fluoro-1,4-phenylene, 3,5-difluoro-1,4-phenylene, 3-fluoro-5-chloro-1,4-phenylene, pyrimidine-2,5-diyl or pyridine-2,5-diyl; $Z^1$ and $Z^2$ are each independently a single bond, or alkylene having 1 to 4 carbons; $Z^3$ is —COO— or —CF$_2$O—; $L^{11}$ is hydrogen, fluorine or chlorine; $Y^1$ is fluorine, chlorine, —CF$_3$ or —OCF$_3$; n1 and n2 are each independently 0 or 1, and n1+n2≥1.

Item 2 is the liquid crystal composition of item 1 in which the achiral component (T) includes at least one compound represented by any one of formulae (1-1) to (1-12).

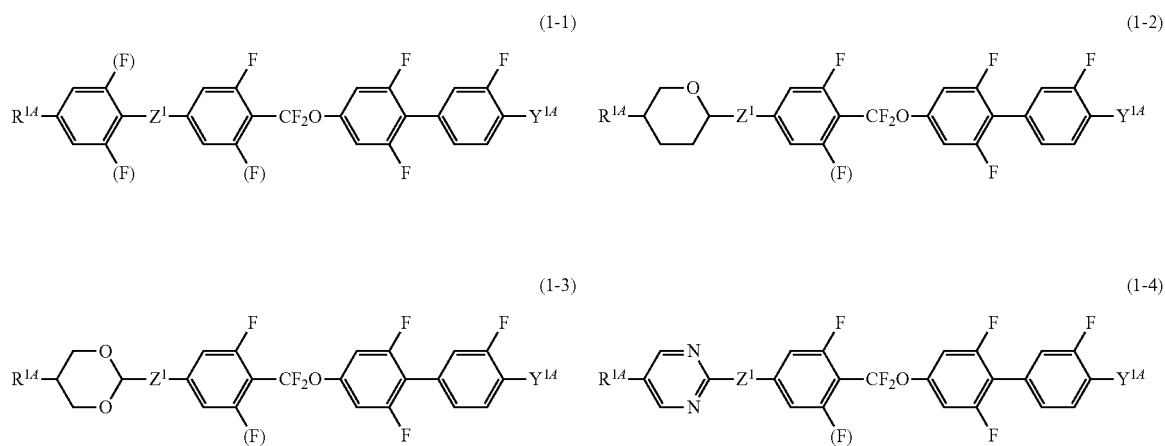

(1-1) (1-2) (1-3) (1-4)

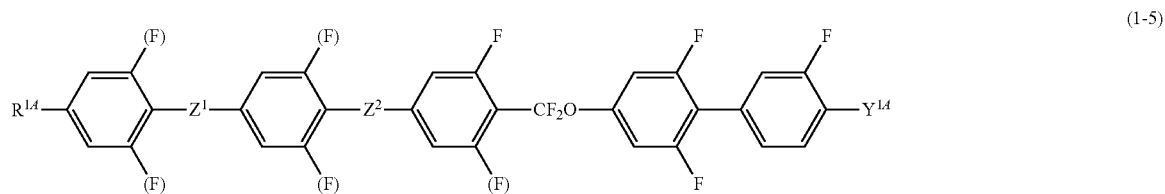

(1-5)

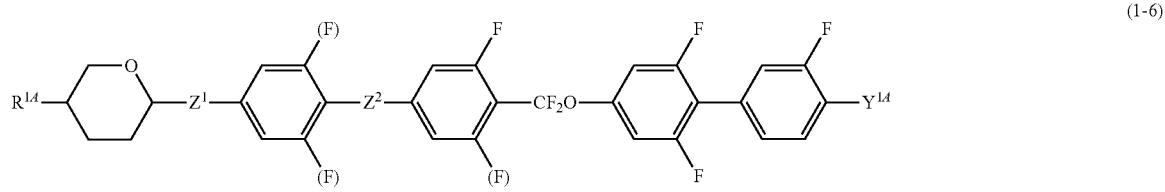

(1-6)

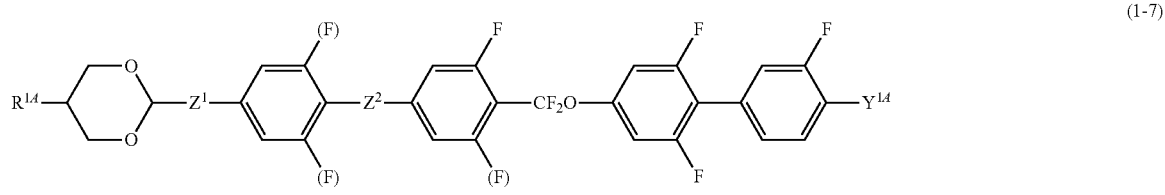

(1-7)

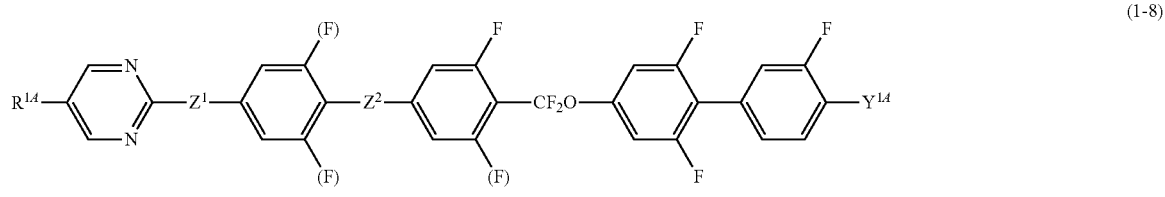

(1-8)

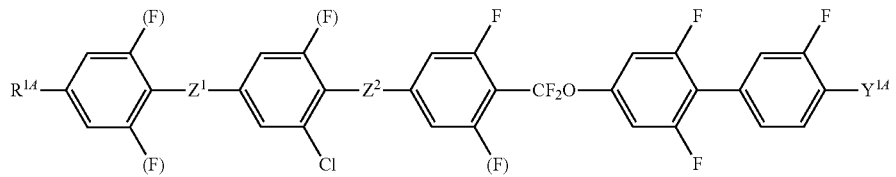
(1-9)

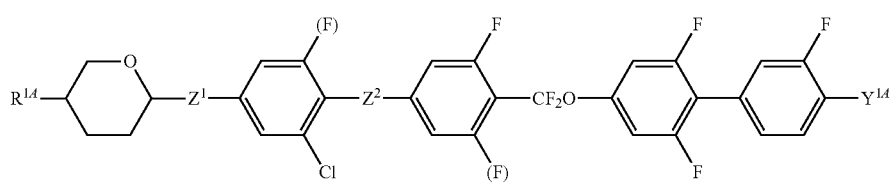
(1-10)

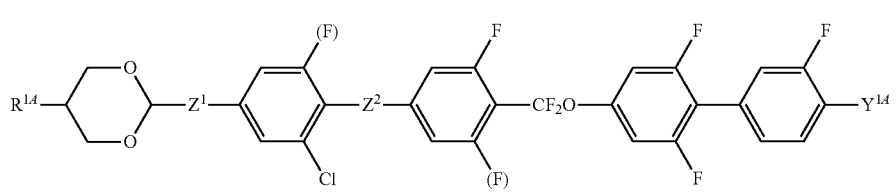
(1-11)

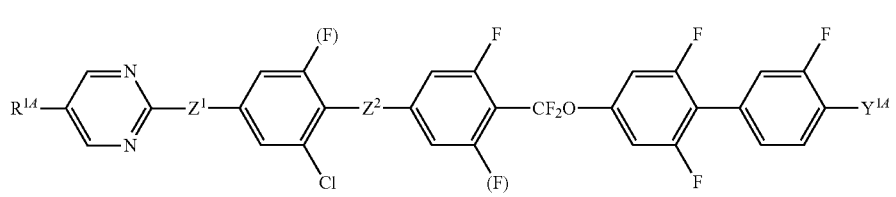
(1-12)

In formulae (1-1) to (1-12), $R^{14}$ is alkyl having 1 to 12 carbons or alkenyl having 2 to 12 carbons, $Z^1$ and $Z^2$ are each independently a single bond or alkylene having 1 to 4 carbons, $Y^{14}$ is fluorine, —$OCF_3$ or —$CF_3$, and (F) is fluorine or hydrogen.

Item 3 is the liquid crystal composition of item 1 or 2 which further includes, as a second component of the achiral component (T), at least one selected from the group consisting of a compound (3) represented by formula (3) and a compound (7) represented by formula (7).

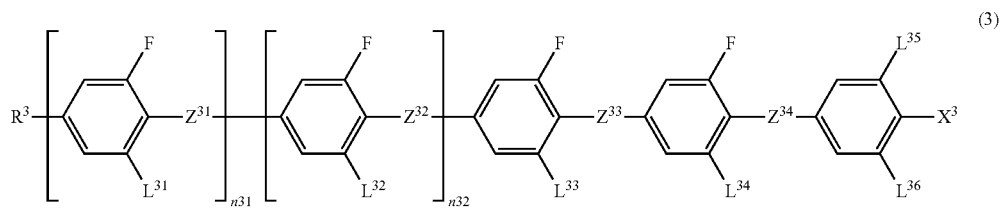
(3)

In formula (3), $R^3$ is hydrogen, or alkyl having 1 to 12 carbons, wherein at least one —$CH_2$— in $R^3$ may be replaced with —O—, —S—, —COO— or —OCO—, at least one —$CH_2$—$CH_2$— in $R^3$ may be replaced with —CH=CH—, —CF=CF— or at least one hydrogen in $R^3$ may be replaced with fluorine or chlorine, and in $R^3$, —O— and —CH=CH— are not adjacent to each other and —CO— and —CH=CH— are not adjacent to each other; $Z^{31}$, $Z^{32}$, $Z^{33}$ and $Z^{34}$ are each independently a single bond, or alkylene having 1 to 4 carbons, wherein at least one —$CH_2$— in the alkylene may be replaced with —O—, —COO— or —$CF_2$O—; $L^{31}$, $L^{32}$, $L^{33}$, $L^{34}$, $L^{35}$ and $L^{36}$ are each independently hydrogen or fluorine; $X^3$ is hydrogen, halogen, —$SF_5$, or alkyl having 1 to 10 carbons, wherein at least one —$CH_2$— in $X^3$ may be replaced with —O—, —S—, —COO— or —OCO—, at least one —$CH_2$—$CH_2$— in $X^3$ may be replaced with —CH=CH—, —CF=CF— or —C≡C—, at least one hydrogen in $X^3$ may be replaced with fluorine or chlorine, and in $X^3$, —O— and —CH=CH— are not adjacent to each other and —CO— and —CH=CH— are not adjacent to each other; n31 and n32 are each independently 0 or 1; and when $Z^{33}$ is —$CF_2$O— or —COO—, $Z^{34}$ is a single bond and $L^{34}$ is fluorine, both $L^{35}$ and $L^{36}$ are fluorine.

—COO—, $Z^{73}$ is a single bond and both $L^{75}$ and $L^{76}$ are fluorine, both $L^{77}$ and $L^{78}$ are fluorine; and when n71=0, $Z^{71}$ is —$CF_2$O— or —COO—, $Z^{73}$ is a single bond and both $L^{75}$ and $L^{76}$ are fluorine, both $L^{77}$ and $L^{78}$ are fluorine.

Item 4 is the liquid crystal composition of item 3 in which the compound (3) is a compound represented by any one of formulae (3-1) to (3-3).

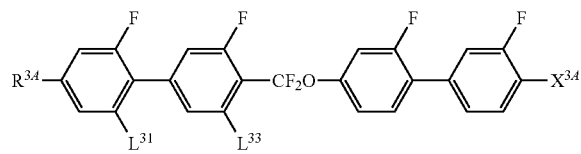

(3-1)

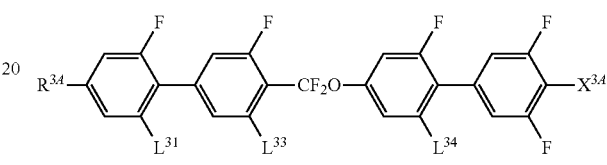

(3-2)

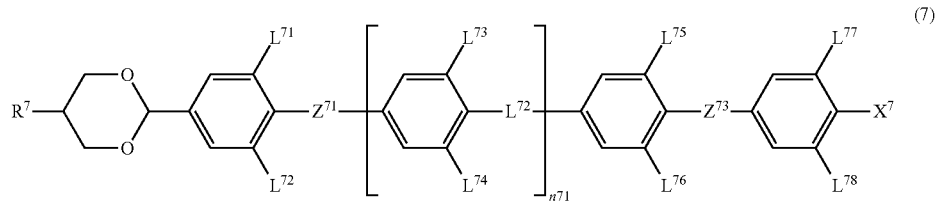

(7)

In formula (7), $R^7$ is hydrogen, or alkyl having 1 to 12 carbons, wherein at least one —$CH_2$— in $R^7$ may be replaced with —O—, —S—, —COO— or —OCO—, at least one —$CH_2$—$CH_2$— in $R^7$ may be replaced with —CH=CH—, —CF=CF— or —C≡C—, at least one hydrogen in $R^7$ may be replaced with fluorine or chlorine, and in $R^7$, —O— and —CH=CH— are not adjacent to each other and —CO— and —CH-CH are not adjacent to each other; $L^{71}$, $L^{72}$, $L^{73}$, $L^{74}$, $L^{75}$, $L^{76}$, $L^{77}$ and $L^{78}$ are each independently hydrogen or fluorine; $Z^{71}$, $Z^{72}$ and $Z^{73}$ are each independently a single bond, —OCO— or —$CF_2$O—; $X^7$ is hydrogen, halogen, —$SF_5$, or alkyl having 1 to 10 carbons, wherein at least one —$CH_2$— in $X^7$ may be replaced with —O—, —S—, —OCO— or —OCO—, at least one —$CH_2$—$CH_2$— in $X^7$ may be replaced with —CH=CH—, —CF=CF— or —C≡C—, at least one hydrogen in $X^7$ may be replaced with fluorine or chlorine, and in $X^7$, —O— and —CH=CH— are not adjacent to each other and —CO— and —CH=CH— are not adjacent to each other; n71 is 0 or 1; when n71=1, $Z^{72}$ is —$CF_2$O— or -continued

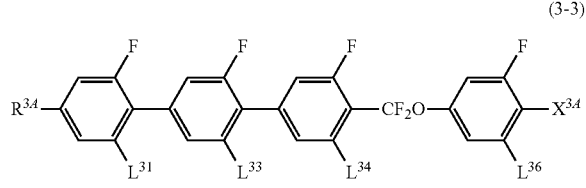

(3-3)

In formulae (3-1) to (3-3), each $R^{3A}$ is independently alkyl having 1 to 12 carbons, alkenyl having 2 to 12 carbons or alkoxy having 1 to 11 carbons, $L^{31}$, $L^{33}$, $L^{34}$ and $L^{36}$ are each independently hydrogen or fluorine, and $X^{3A}$ is fluorine, chlorine, —$CF_3$ or —$OCF_3$.

Item 5 is the liquid crystal composition of item 3, wherein the compound (7) is a compound represented by any one of formulae (7-1) to (7-8).

(7-1) 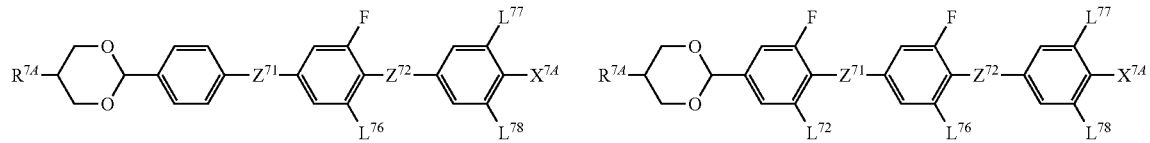
(7-2) 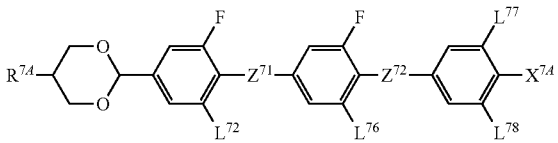
(7-3) 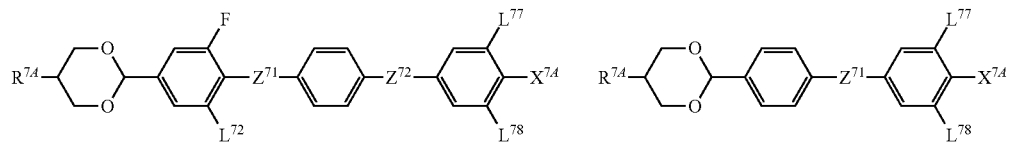
(7-4) 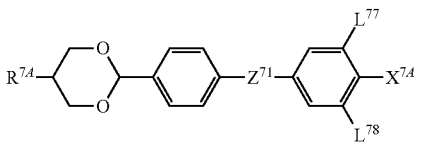
(7-5) 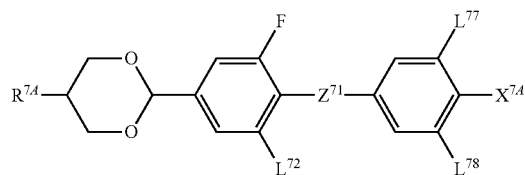
(7-6) 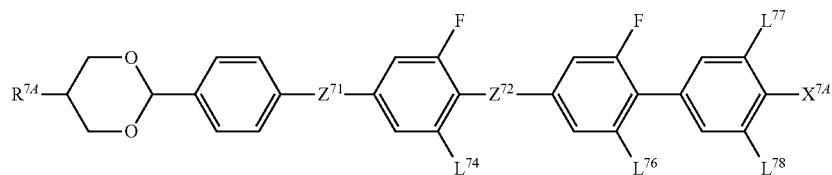
(7-7) 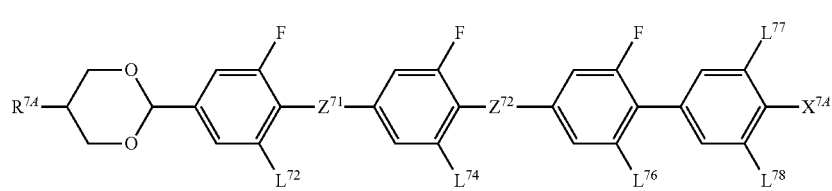
(7-8) 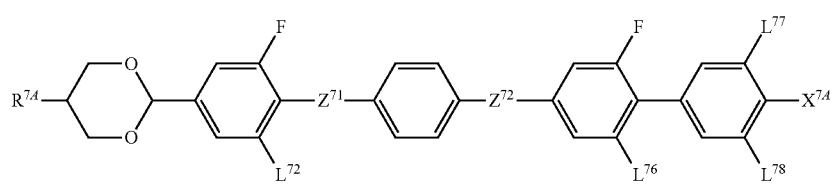

In formulae (7-1) to (7-8), each $R^{74}$ is independently hydrogen, alkyl having 1 to 12 carbons, alkenyl having 2 to 12 carbons, or alkoxy having 1 to 11 carbons; $L^{72}$, $L^{74}$, $L^{76}$, $L^{77}$ and $L^{78}$ are each independently hydrogen or fluorine; each $X^{74}$ is independently fluorine, chlorine, $-CF_3$ or $-OCF_3$; $Z^{71}$ and $Z^{72}$ are each independently a single bond, $-COO-$ or $-CF_2O-$, and at least one of $Z^{71}$ and $Z^{72}$ is $-COO-$ or $-CF_2O-$; and when $L^{76}$ is fluorine, both $L^{77}$ and $L^{78}$ are fluorine.

Item 6 is the liquid crystal composition of item 3 in which the compound (7) is a compound represented by any one of formulae (7-2-1) to (7-2-7).

(7-2-1)
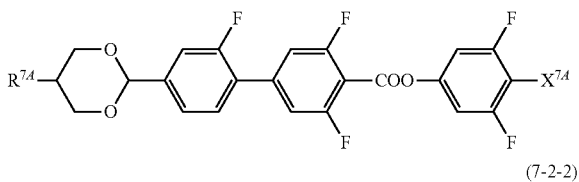

(7-2-2)
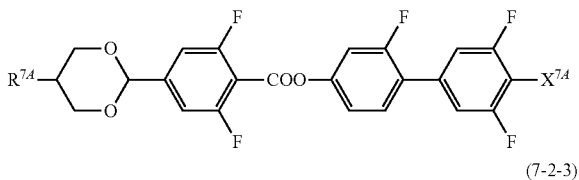

(7-2-3)
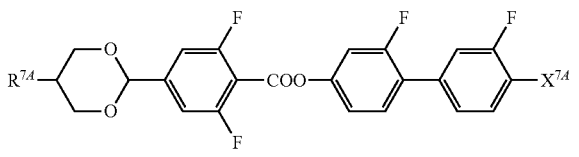

(7-2-4)
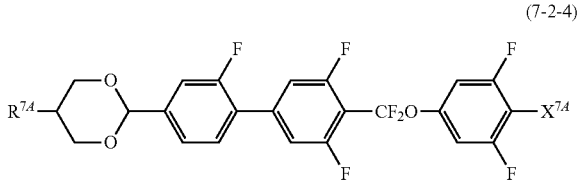

(7-2-5)
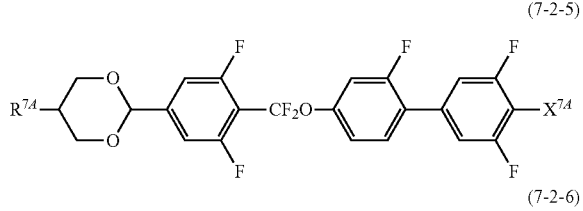

(7-2-6)
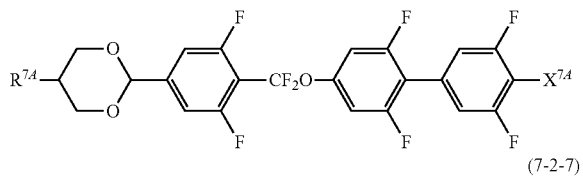

(7-2-7)
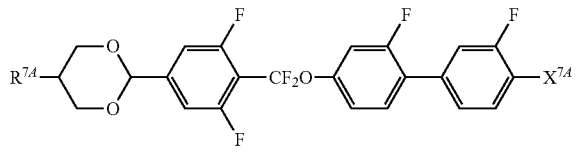

In formulae (7-2-1) to (7-2-7), each $R^{74}$ is independently alkyl having 1 to 12 carbons, alkenyl having 2 to 12 carbons or alkoxy having 1 to 11 carbons, and $^{74}$ is fluorine, chlorine, $-CF_3$ or $-OCF_3$.

Item 7 is the liquid crystal composition of any one of items 3 to 6 which contains a total of 10 to 30 wt % of the compound (1), a total of 20 to 60 wt % of the compound (3) and a total of 30 to 70 wt % of the compound (7), based on the total weight of the achiral component (T).

Item 8 is the liquid crystal composition of any one of items 1 to 7 which further includes, as a third component of the achiral component (T), at least one selected from the group consisting of a compound (4) represented by formula (4) and a compound (2) represented by formula (2).

(4)
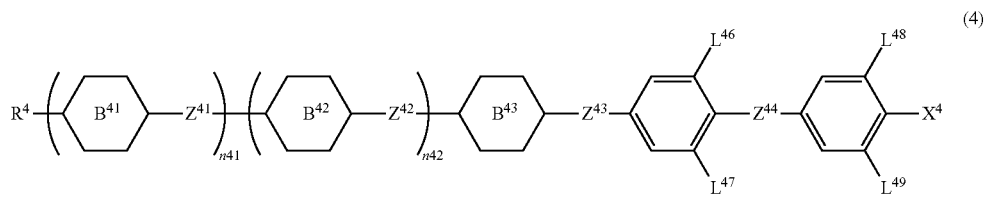

In formula (4), $R^4$ is alkyl having 1 to 12 carbons, alkenyl having 2 to 12 carbons, or alkoxy having 1 to 11 carbons; $B^{41}$, $B^{42}$ and $B^{43}$ are each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2,5-diyl, wherein at least one of $B^{41}$, $B^{42}$ and $B^{43}$ is 1,4-cyclohexylene, 1,4-phenylene or pyrimidine-2,5-diyl; $Z^{41}$, $z^{42}$, $Z^{43}$ and $Z^{44}$ are each independently a single bond, ethylene, $-COO-$, $-OCO-$, $-CF_2O-$ or $-OCF_2-$; $L^{46}$, $L^{47}$, $L^{48}$ and $L^{49}$ are each independently hydrogen or fluorine; $X^4$ is fluorine, chlorine, $-CF_3$ or $-OCF_3$; n41 and n42 are each independently 0 or 1; and when $Z^{43}$ is —$CF_2O$— or —COO—, $Z^{44}$ is a single bond and both $L^{46}$ and $L^{47}$ are fluorine, both $L^{48}$ and $L^{49}$ are fluorine.

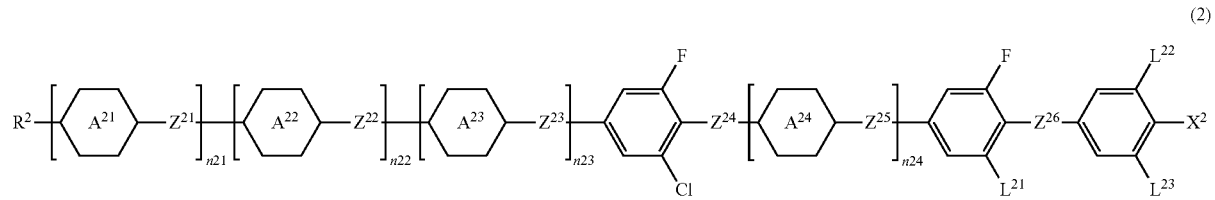

(2)

In formula (2), $R^2$ is hydrogen, or alkyl having 1 to 12 carbons, wherein at least one —$CH_2$— in $R^2$ may be replaced with —O—, —S—, —COO—, —OCO—, —CH═CH—, —CF═CF— or at least one hydrogen in $R^2$ may be replaced with halogen or alkyl having 1 to 3 carbons, and in $R^2$, —O— and —CH═CH— are not adjacent to each other and —CO— and —CH═CH— are not adjacent to each other; $A^{21}$, $A^{22}$, $A^{23}$ and $A^{24}$ are each independently 1,4-cyclohexylene, 1,3-dioxane-2,5-diyl, 1,4-phenylene, 1,4-phenylene in which one or two hydrogens are replaced with fluorine, 1,4-phenylene in which two hydrogens are replaced with fluorine and chlorine respectively, pyridine-2,5-diyl, or pyrimidine-2,5-diyl; $Z^{21}$, $Z^{22}$, $Z^{23}$, $Z^{24}$, $Z^{25}$ and $Z^{26}$ are each independently a single bond, or alkylene having 1 to 4 carbons, wherein at least one —$CH_2$— in the alkylene may be replaced with —O—, —COO— or —$CF_2O$—; $L^{21}$, $L^{22}$ and $L^{23}$ are each independently hydrogen or fluorine; $X^2$ is fluorine, chlorine, —$CF_3$ or —$OCF_3$; n21, n22, n23 and n24 are each independently 0 or 1, and 1≤n21+n22+n23+n24≤2; and when $Z^{26}$ is a single bond and $L^{21}$ is fluorine, both $L^{22}$ and $L^{23}$ are fluorine.

Item 9 is the liquid crystal composition of item 8 in which the compound (4) is a compound represented by any one of formulae (4-1) to (4-10).

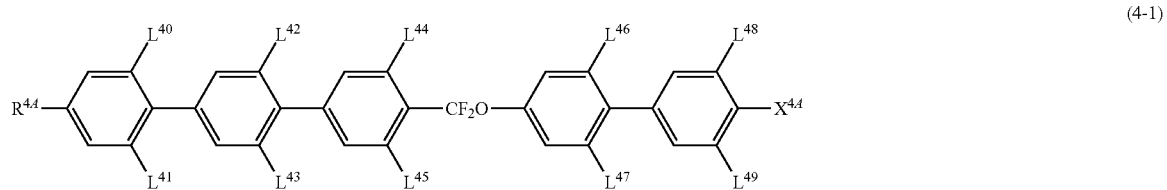

(4-1)

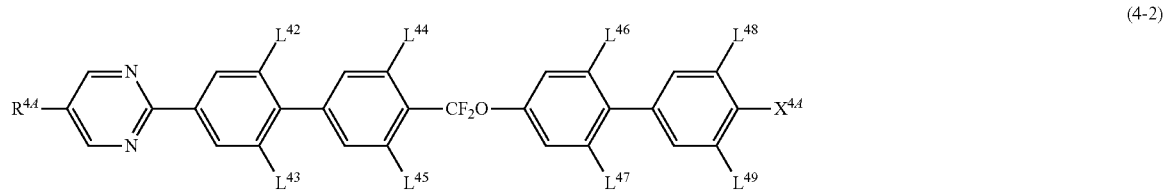

(4-2)

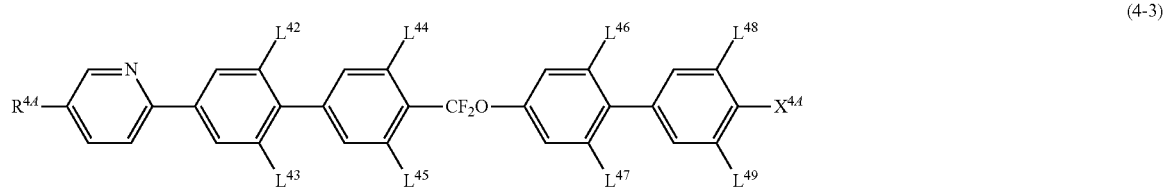

(4-3)

(4-4) (4-5)

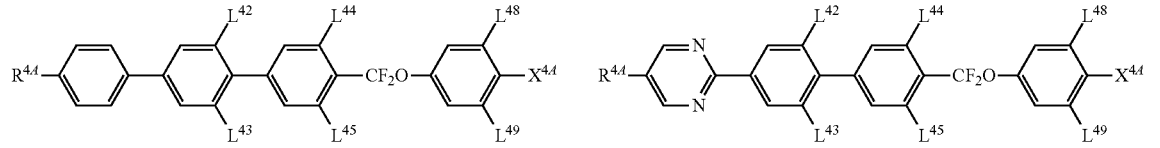

(4-6) (4-7)

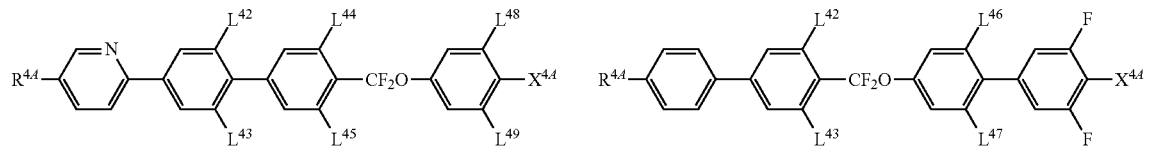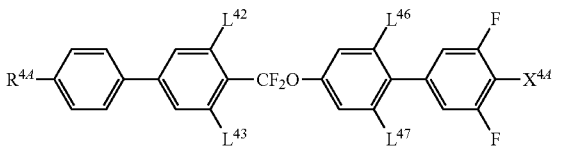

-continued

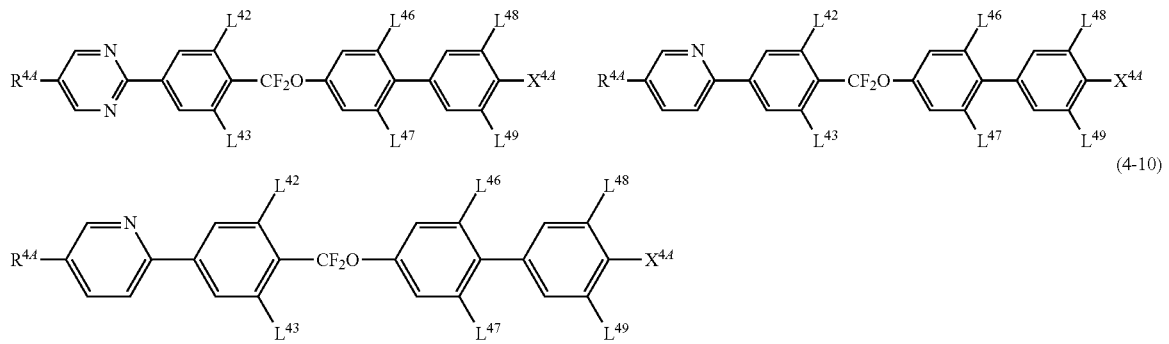

In formulae (4-1) to (4-10), each $R^{4A}$ is independently alkyl having 1 to 12 carbons, alkenyl having 2 to 12 carbons or alkoxy having 1 to 11 carbons, $X^{4A}$ is fluorine, chlorine, —$CF_3$ or —$OCF_3$, $L^{40}$ to $L^{49}$ are each independently hydrogen or fluorine, and when both $L^{46}$ and $L^{47}$ are fluorine, both $L^{48}$ and $L^{49}$ are fluorine.

Item 10 is the liquid crystal composition of item 8 in which the compound (2) is a compound represented by any one of formulae (2-1-1-2), (2-1-2-1), (2-1-3-1), (2-1-3-2), (2-1-4-2) and (2-1-4-3).

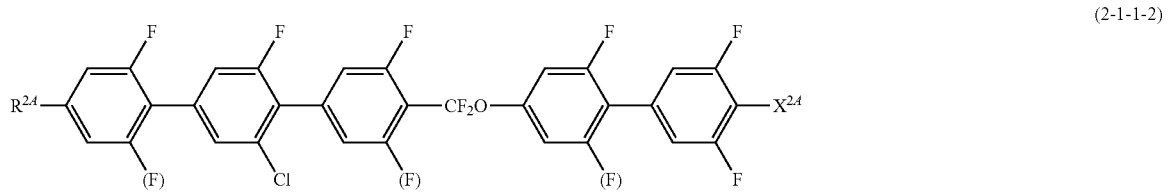

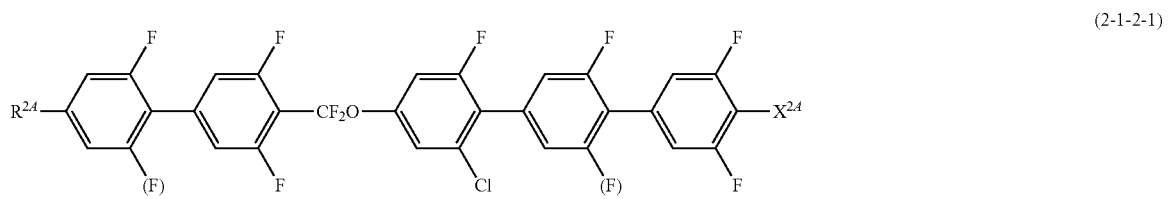

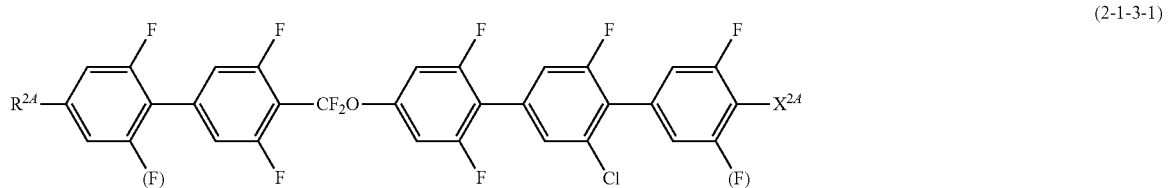

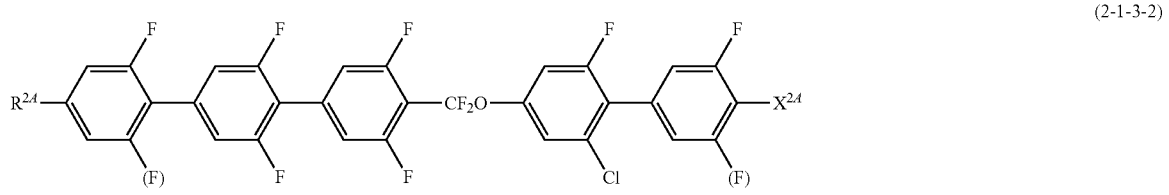

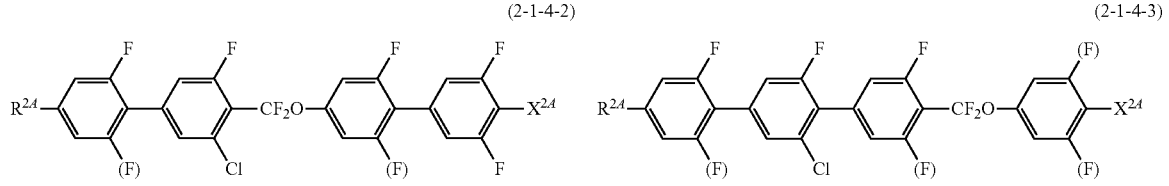

In the above formulae, each $R^{24}$ is independently alkyl having 1 to 12 carbons, alkenyl having 2 to 12 carbons or alkoxy having 1 to 11 carbons, each (F) is independently hydrogen or fluorine, and $X^{24}$ is fluorine, chlorine, —CF$_3$ or —OCF$_3$.

Item 11 is the liquid crystal composition of any one of items 1 to 10 in which the chiral agent includes at least one selected from the group consisting of compounds (K1) to (K7) represented by formulae (K1) to (K7).

(K1)
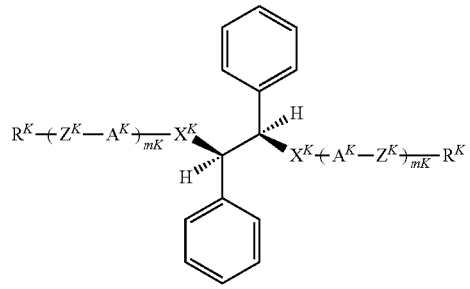

(K2)
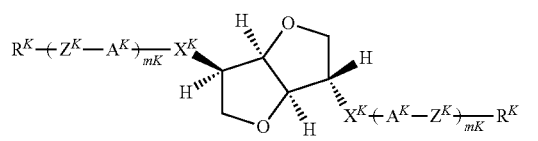

(K3)
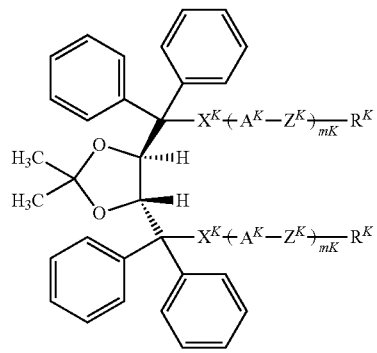

(K4)
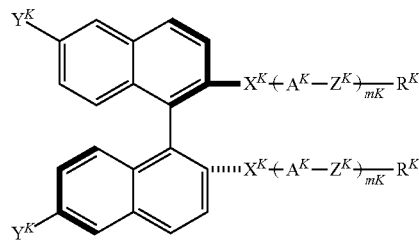

(K5)
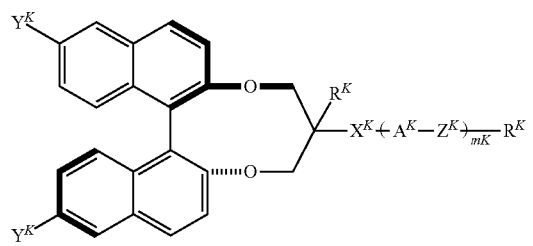

(K6)
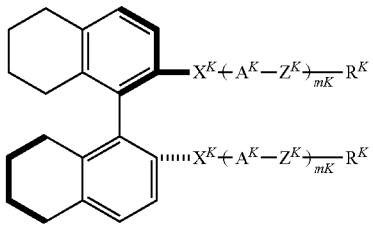

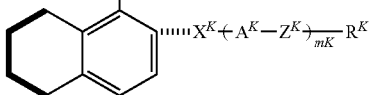

(K7)
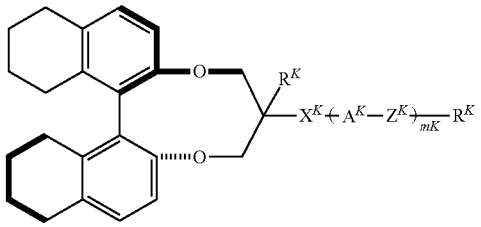

In formulae (K1) to (K7), each $R^K$ is independently hydrogen, halogen, —C≡N, —N═C═O, —N═C═S, or alkyl having 1 to 12 carbons, wherein at least one —CH$_2$— in $R^K$ may be replaced with —O—, —S—, —COO— or —OCO—, at least one —CH$_2$—CH$_2$— in $R^K$ may be replaced with —CH═CH—, —CF═CF— or and at least one hydrogen in $R^K$ may be replaced with fluorine or chlorine; each $A^K$ is independently an aromatic six- to eight-membered ring, a non-aromatic three- to eight-membered ring, or a fused ring having 9 or more carbons, wherein at least one hydrogen in these rings may be replaced with halogen, alkyl having 1 to 3 carbons or haloalkyl having 1 to 3 carbons, —CH$_2$— in these rings may be replaced with —O—, —S— or —NH—, and —CH═ in these rings may be replaced with —N═; each $Y^K$ is independently hydrogen, halogen, alkyl having 1 to 3 carbons, haloalkyl having 1 to 3 carbons, an aromatic six- to eight-membered ring, a non-aromatic three- to eight-membered ring, or a fused ring having 9 or more carbons, wherein at least one hydrogen in these rings may be replaced with halogen, alkyl having 1 to 3 carbons or haloalkyl having 1 to 3 carbons, —CH$_2$— in the alkyl may be replaced with —O—, —S— or —NH—, and —CH═ in these rings may be replaced with —N═; each $Z^K$ is independently a single bond, or alkylene having 1 to 8 carbons, wherein at least one in —$Z^K$— may be replaced with —O—, —S—, —COO—, —OCO—, —CSO—, —OCS—, —N═N—, —CH═N— or —N═CH—, at least one —CH$_2$—CH$_2$— in $Z^K$ may be replaced with —CH═CH—, —CF═CF— or and at least one hydrogen in $Z^K$ may be replaced with halogen; each $X^K$ is independently a single bond, —COO—, —OCO—, —CH$_2$O—, —OCH$_2$—, —CF$_2$O—, —OCF$_2$— or —CH$_2$CH$_2$—; and each mK is independently an integer of 1 to 3.

Item 12 is the liquid crystal composition of any one of items 1 to 11 which exhibits a chiral nematic phase at any temperature in the range of −20 to 70° C. and has a helical pitch of 700 nm or less within at least a part of the temperature range.

Item 13 is a mixture which includes the liquid crystal composition of any one of items 1 to 11 and a polymerizable monomer.

Item 14 is a polymer/liquid-crystal composite material obtained by polymerizing the mixture of item 13 and for use in a device driven in an optically isotropic liquid crystal phase.

Item 15 is an optical device which includes two substrates in which electrodes are disposed on one or both thereof, a liquid crystal medium disposed between the substrates, and an electric field-applying means for applying an electric field to the liquid crystal medium through the electrodes, wherein the liquid crystal medium is the liquid crystal composition of any one of items 1 to 12 or the polymer/liquid-crystal composite material of item 14.

Item 16 is use of the liquid crystal composition of any one of items 1 to 11 or the polymer/liquid-crystal composite material of item 14 for an optical device.

Item 17 is a compound represented by formula (1A):

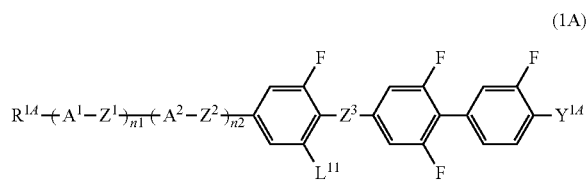

(1A)

where each $R^{14}$ is independently hydrogen, alkyl having 1 to 12 carbons, alkenyl having 2 to 12 carbons, alkynyl having 2 to 12 carbons, or alkoxy having 1 to 11 carbons; $A^1$ and $A^2$ are each independently 1,3-dioxane-2,5-diyl, tetrahydropyran-2,5-diyl, 1,4-phenylene, 3-fluoro-1,4-phenylene, 3,5-difluoro-1,4-phenylene, or 3-fluoro-5-chloro-1,4-phenylene; $Z^1$ and $Z^2$ are each independently a single bond, or alkylene having 1 to 4 carbons; $Z^3$ is —COO— or —CF$_2$O—; each $L^{11}$ is independently hydrogen, fluorine or chlorine; $Y^{14}$ is fluorine, chlorine, —CF$_3$ or —OCF$_3$; n1 and n2 are each independently 0 or 1, and n1+n2≥1.

Item 18 is a compound represented by any one of formulae (1-1-1) to (1-1-3), (1-3-1) to (1-3-3), (1-S-1) to (1-S-3) and (1-7-1) to (1-7-3):

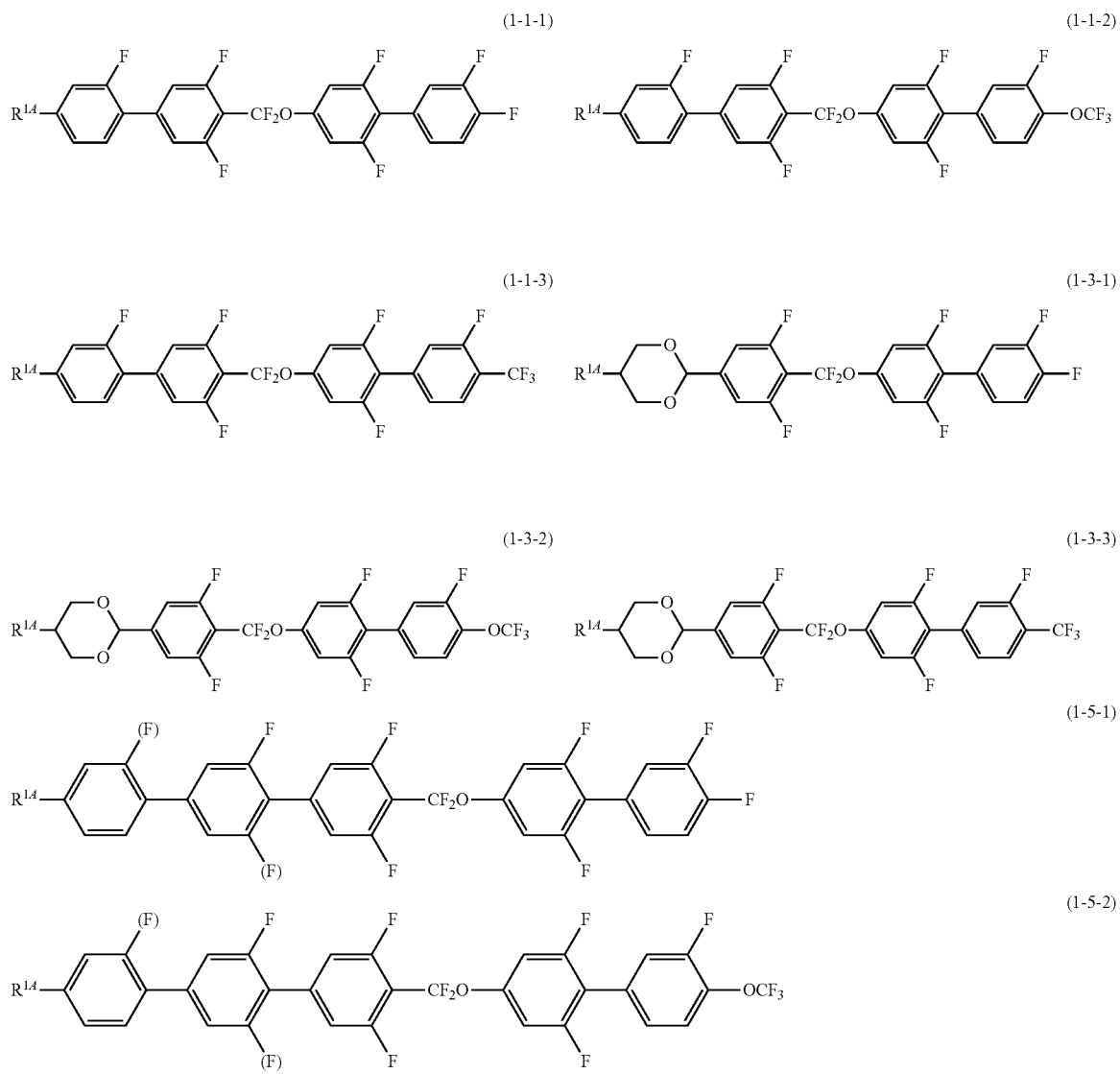

-continued

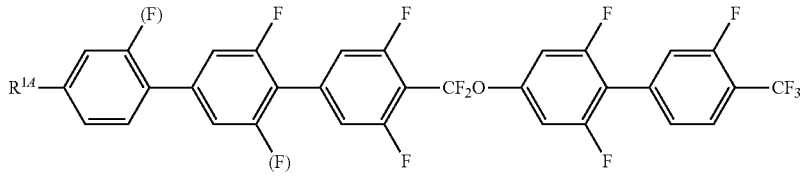
(1-5-3)

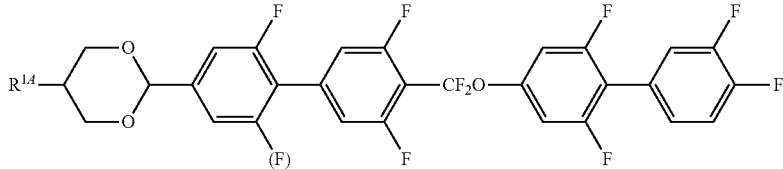
(1-7-1)

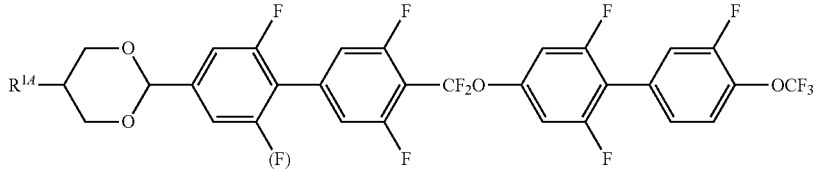
(1-7-2)

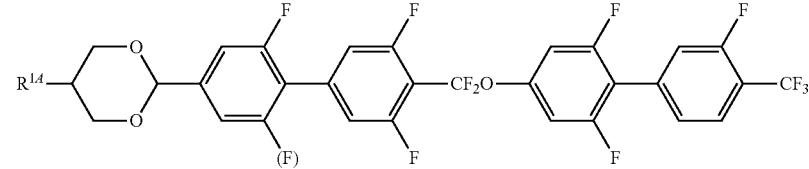
(1-7-3)

wherein $R^{14}$ is alkyl having 1 to 12 carbons and (F) is hydrogen or fluorine.

In this specification, "a liquid crystal compound" refers to a compound having a mesogen, and is not limited to a compound exhibiting a liquid crystal phase. Specifically, it is a generic term for a compound exhibiting a liquid crystal phase such as a nematic phase, a smectic phase or the like and a compound useful as a component of a liquid crystal composition though having no liquid crystal phase.

"Liquid crystal medium" is a generic term for a liquid crystal composition and a polymer/liquid-crystal composite.

"Achiral component" refers to an achiral mesogen compound, being a component including no optically active compound or compound having a polymerizable group. Accordingly, the "achiral component" does not include a chiral agent, a monomer, a polymerization initiator, an antioxidant, an ultraviolet absorber, a curing agent or a stabilizer, etc.

"A chiral agent" refers to an optically active compound, and is a component added in order to give a desired twisted molecular arrangement to the liquid crystal composition.

"Liquid crystal display device" ("LCD device") is a generic term for an LCD panel and an LCD module.

In addition, "optical device" refers to various devices that perform functions such as optical modulation and optical switching, etc. by utilizing an electro-optic effect, and examples thereof include optical modulators used in, e.g., display devices (LCD devices), optical communication systems, optical information processing or various sensor systems. For optical modulation utilizing a change of refractive index by applying a voltage to an optically isotropic liquid crystal medium, the Kerr effect is known. The Kerr effect means a phenomenon in which the electric birefringence value $\Delta n(E)$ is proportional to the square of the electric field E, and the equation $\Delta n(E)=K\lambda^2$ is satisfied in a material showing the Kerr effect (K: Kerr coefficient (Kerr constant), $\lambda$: wavelength). Herein, the electric birefringence value refers to a value of refractive index anisotropy induced when the electric field is applied to an isotropic medium.

"Liquid crystal compound," "liquid crystal composition," and "LCD device" are sometimes abbreviated as "compound," "composition," and "device," respectively.

In addition, for example, the upper-limit temperature of a liquid crystal phase is a phase transition temperature between the liquid crystal phase and an isotropic phase, and is sometimes abbreviated simply as "clearing point" or "upper-limit temperature." A lower-limit temperature of the liquid crystal phase is sometimes abbreviated simply as "lower-limit temperature." In the compounds (2) to (5), symbols $A^1$, $B^1$, $C^1$ and so on surrounded by a hexagon correspond to ring $A^1$, ring $B^1$, ring $C^1$ and so on, respectively. The amount of a compound expressed in terms of percentage is expressed in terms of weight percentage (wt %) based on the total weight of the composition. A plurality of identical symbols such as ring $A^1$, $Y^1$, $B^1$ or the like are described in the same or different formulae, and may mean the same or different groups therein.

In this specification, the "alkyl" may be linear or branched, and specific examples include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, and —$C_{12}H_{25}$.

In this specification, the "alkenyl" may be linear or branched, and specific examples include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$, and —$(CH_2)_3$—CH=$CH_2$.

In addition, the preferred configuration of —CH═CH— depends on the position of the double bond. The trans configuration is preferred for alkenyl groups having the double bond in an odd-numbered position, such as —CH═CHCH₃, —CH═CHC₂Hs, —CH═CHC₃H7, —CH═CHC₄H9, —C₂H4CH═CHCH₃ and —C₂H4CH═CHC₂Hs. The cis configuration is preferred for alkenyl groups having the double bond in an even-numbered position, such as —CH₂CH═CHCH₃, —CH₂CH═CHC₂H5 and —CH₂CH═CHC₃H7. An alkenyl compound having a preferred configuration has a high upper-limit temperature or a wide temperature range of liquid crystal phase. A detailed explanation is given in *Mol. Cryst. Liq. Cryst.*, 1985, 131, 109 and *Mol. Cryst. Liq. Cryst.*, 1985, 131, 327. In addition, the double bond is preferably at a position where it is not conjugated with a benzene ring.

In this specification, the "alkynyl" may be linear or branched, and specific examples thereof include —C≡CH, —C≡CCH₃, —CH₂C≡CH, —C≡CC₂H₅, —CH₂C≡CCH₃, —(CH₂)₂—C≡CH, —C≡CC₃H7, —CH₂C≡CC₂H₅, —(CH₂)₂—C≡CCH₃ and —C≡C(CH₂)₅.

In this specification, the "alkoxy" may be linear or branched, and specific examples thereof include —OCH₃, —OC₂H₅, —OC₃H₇, —OC₄H₉, —OC₅H₁₁, —OC₆H₁₃ and —OC₇H₅, —OC₈H₁₇, —OC₉H₁₉, —OC₁₀H₂₁ and —OC₁₁H₂₃.

In this specification, the "alkoxyalkyl" may be linear or branched, and specific examples thereof include —CH₂OCH₃, —CH₂OC₂H5s, —CH₂OC₃H₇, —(CH₂)₂—OCH₃, —(CH₂)₂—OC₂H5, —(CH₂)₂—OC₃H₇, —(CH₂)₃—OCH₃, —(CH₂)₄—OCH₃ and —(CH₂)₅—OCH₃.

In this specification, the "alkenyloxy" may be linear or branched, and specific examples thereof include —OCH₂CH═CH₂, —OCH₂CH═CHCH₃ and —OCH₂CH═CHC₂H₅.

In this specification, specific examples of the "halogen" include fluorine, chlorine, bromine and iodine.

A preferred compound of the invention shows liquid crystal properties and has a relatively high clearing point, a wide nematic phase temperature range, and a relatively large dielectric anisotropy. In addition, a polymer/liquid-crystal composite material or the like using an optically isotropic liquid crystal composition containing the compound of the invention has a low driving voltage but a small permittivity.

A preferred liquid crystal composition and a preferred polymer/liquid-crystal composite material or the like of the invention show stability to heat, light and so on, and a high upper-limit temperature and a low lower-limit temperature of an optically isotropic liquid crystal phase, and has a low driving voltage but a small permittivity.

Furthermore, an optical device driven in an optically isotropic liquid crystal phase according to a preferred aspect of the invention can be used in a wide temperature range and can be driven at a low voltage. Moreover, the optical device has a driving voltage having a small temperature dependence in a temperature range around the operating temperature, can achieve a high-speed electro-optical response, and has a large contrast ratio.

The compound (1) of this application is characterized by having a fluorobiphenyl group in a terminal group, and the polymer/liquid-crystal composite material produced by using an optically isotropic liquid crystal composition containing the compound (1) of this application is characterized by a low driving voltage and a low permittivity. There is no description of such effect in Patent Literatures 14-18 and so on, and the effect is first discovered by this invention.

DESCRIPTION OF THE EMBODIMENTS

Figure 1:
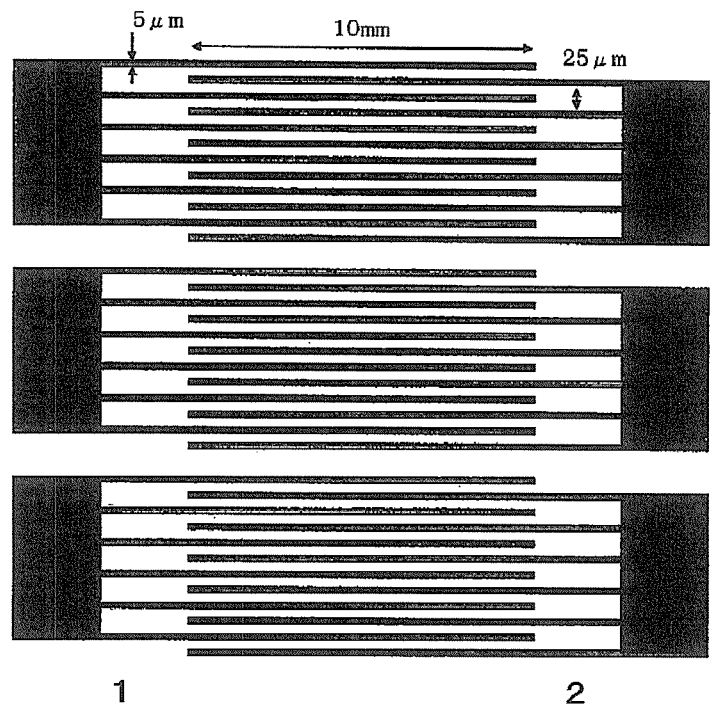
FIG. 1 shows a comb-shaped electrode substrate used in the Examples.

A liquid crystal composition having an optically isotropic liquid crystal phase of the invention contains an achiral component T and a chiral agent, wherein the achiral component T includes a compound (1) as a first component. A first aspect of the liquid crystal composition of the invention is a composition containing the first component and any other component whose component name is not particularly shown in this specification. First of all, the compound (1) is explained. In addition, the liquid crystal composition of the invention may further contain, in addition to the above components, a solvent, a monomer, a polymerization initiator, a curing agent, a stabilizer (antioxidant, ultraviolet absorber or the like) and so forth.

1-1. Compound (1)

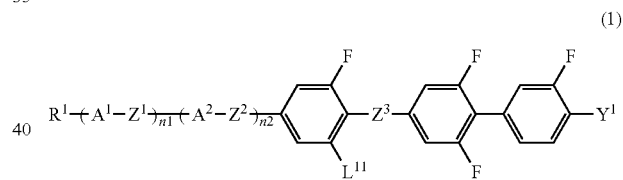

(1)

In the compound (1), $R^1$ is hydrogen, alkyl having 1 to 12 carbons, alkenyl having 2 to 12 carbons, alkynyl having 2 to 12 carbons, or alkoxy having 1 to 11 carbons.

It is preferred that $R^1$ has a structure represented by formulae (CHN-1) to (CHN-4). It is more preferred that $R^1$ has a structure represented by formula (CHN-1) or (CHN-2).

(CHN-1)

(CHN-2)

(CHN-3)

(CHN-4)

In the above formulae, $R^{1a}$ is hydrogen, or alkyl having 1 to 12 carbons.

$A^1$ and $A^2$ are each independently 1,4-cyclohexylene, 1,3-dioxane-2,5-diyl, tetrahydropyran-2,5-diyl, 1,4-phenylene, 3-fluoro-1,4-phenylene, 3,5-difluoro-1,4-phenylene, 3-fluoro-5-chloro-1,4-phenylene, pyrimidine-2,5-diyl, or pyridine-2,5-diyl.

$Z^1$ and $Z^2$ are each independently a single bond, or alkylene having 1 to 4 carbons, and are preferably a single bond or ethylene.

$Z^3$ is —COO— or —CF$_2$O—.

$Y^1$ is fluorine, chlorine, —CF$_3$ or —OCF$_3$, and preferably fluorine, —OCF$_3$, or —CF$_3$.

$L^{11}$ is hydrogen, fluorine or chlorine.

n1 and n2 are each independently 0 or 1, and n1+n2≥1.

Regarding the compound (1), it is preferred to use compounds (1-1) to (1-12).

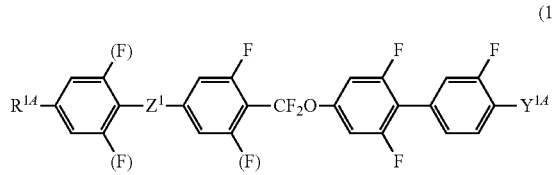 (1-1)

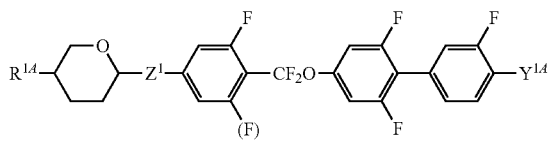 (1-2)

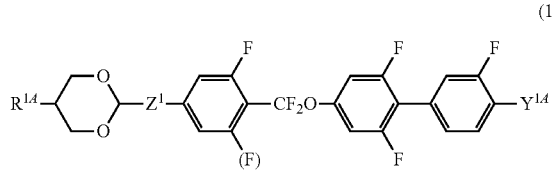 (1-3)

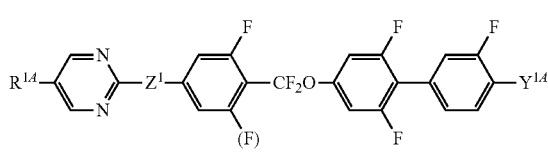 (1-4)

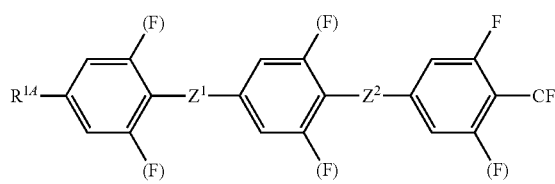 (1-5)

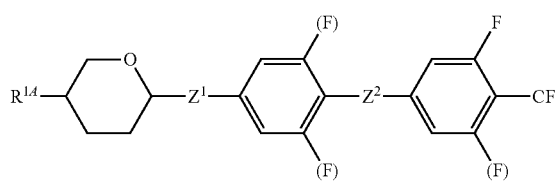 (1-6)

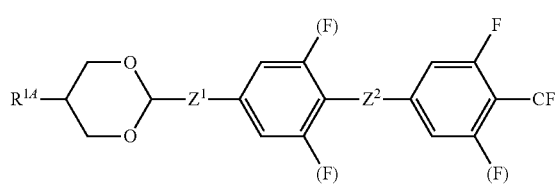 (1-7)

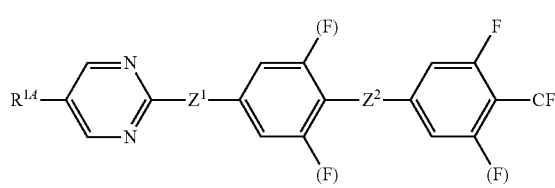 (1-8)

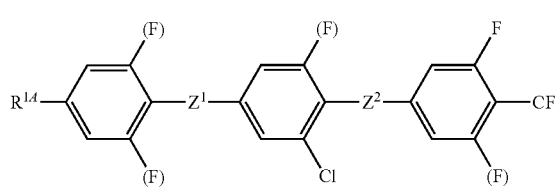 (1-9)

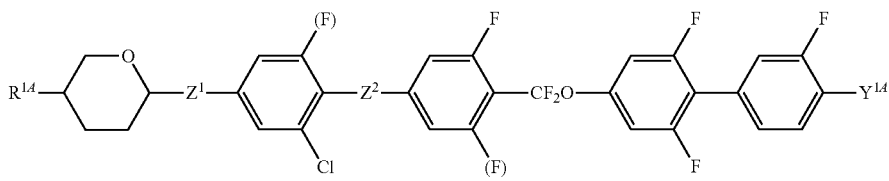

(1-10)

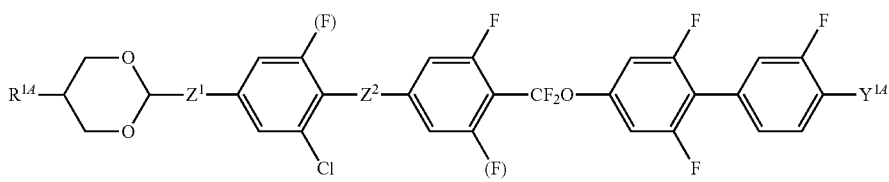

(1-11)

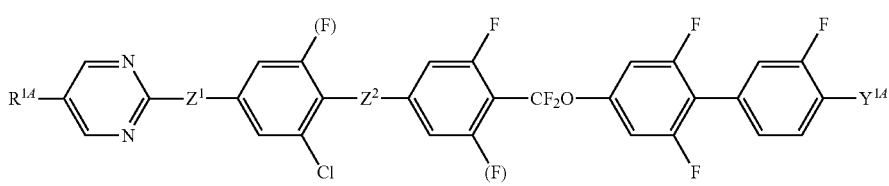

(1-12)

In the above formulae, $R^{1A}$ is alkylene having 1 to 12 carbons or alkenyl having 2 to 12 carbons, $Z^1$ and $Z^2$ are each independently a single bond or alkylene having 1 to 4 carbons, $Y^{1A}$ is fluorine, —$OCF_3$ or —$CF_3$, and (F) is fluorine or hydrogen.

1-2. Properties of Compound (1)

The compound (1) is extremely physically and chemically stable under conditions in which the device is normally used, and has relatively large dielectric anisotropy, relatively large refractive index anisotropy, a high clearing point, and relatively good compatibility with other compounds. A composition containing this compound is stable under conditions in which the device is normally used.

The compound (1) in which $A^1$ and $A^2$ are 3-fluoro-1,4-phenylene or 3,5-difluoro-1,4-phenylene has large dielectric anisotropy and large refractive index anisotropy. The compound (1) in which $A^1$ and $A^2$ are 1,4-phenylene or 3-fluoro-5-chloro-1,4-phenylene has a low melting point and good compatibility with other compounds. The compound (1) in which $A^1$ and $A^2$ are 1,4-cyclohexylene or tetrahydropyran-2,5-diyl has a wide liquid crystal phase and relatively good compatibility with other compounds. The compound (1) in which $A^1$ and $A^2$ are 1,3-dioxane-2,5-diyl has extremely large dielectric anisotropy. The compound (1) in which $A^1$ and $A^2$ are pyrimidine-2,5-diyl or pyridine-2,5-diyl has extremely large dielectric anisotropy and large refractive index anisotropy.

When $Z^1$ and $Z^2$ are single bonds, the compound (1) has large dielectric anisotropy and large refractive index anisotropy. In addition, the compound (1) in which $Z^1$ and $Z^2$ are alkylene having 1 to 4 carbons has a low melting point and good compatibility with other compounds.

The compound (1) in which $Z^3$ is —COO— has a high melting point, a wide liquid crystal phase and large dielectric anisotropy. In addition, the compound (1) in which $Z^3$ is —$CF_2O$— has a low melting point, large dielectric anisotropy, and good compatibility with other compounds.

The compound (1) in which $L^{11}$ is hydrogen has a high clearing point and good compatibility at a low temperature. The compound (1) in which $L^{11}$ is fluorine has a low melting point and extremely large dielectric anisotropy. In addition, the compound (1) in which $L^{11}$ is chlorine has a low melting point, large dielectric anisotropy, and good compatibility with other compounds.

$Y^1$ is fluorine, chlorine, —$CF_3$ or —$OCF_3$. The compound (1) in which $Y^1$ is fluorine or —$OCF_3$ has large dielectric anisotropy, and good compatibility with other compounds. The compound (1) in which $Y^1$ is —$CF_3$ has extremely large dielectric anisotropy. The compound (1) in which $Y^1$ is chlorine has large refractive index anisotropy.

The compound (1) in which n1 is 0 has a relatively high clearing point, large dielectric anisotropy and large refractive index anisotropy. The compound (1) in which n is 1 has a very high clearing point, large dielectric anisotropy and extremely large refractive index anisotropy.

Accordingly, regarding the liquid crystal composition, e.g., if the compound (1) in which $A^1$ and $A^2$ are any of 1,4-phenylene, 3-fluoro-1,4-phenylene and 3,5-difluoro-1,4-phenylene, $L^{11}$ is fluorine, and $Y^1$ is fluorine or —$OCF_3$ is used, a temperature range of the liquid crystal phase can be extended, a driving voltage is low, and the liquid crystal composition can be used as a display device in a wide temperature range.

In addition, regarding the liquid crystal composition, if the compound (1) in which $A^1$ is 1,3-dioxane-2,5-diyl, $A^2$ is 3,5-difluoro-1,4-phenylene, $L^{11}$ is fluorine, and $Y^1$ is fluorine or —$CF_3$ is used, the driving voltage is very low, and the liquid crystal composition can be used as a display device in a wide temperature range.

The compound (1) has an excellent advantage of reducing the driving voltage and reducing permittivity even when it is used in only a small amount as a component of the liquid crystal composition.

Examples of most suitable compounds include compounds (1-1-1) to (1-1-3), (1-3-1) to (1-3-3), (1-5-1) to (1-5-3) and (1-7-1) to (1-7-3).

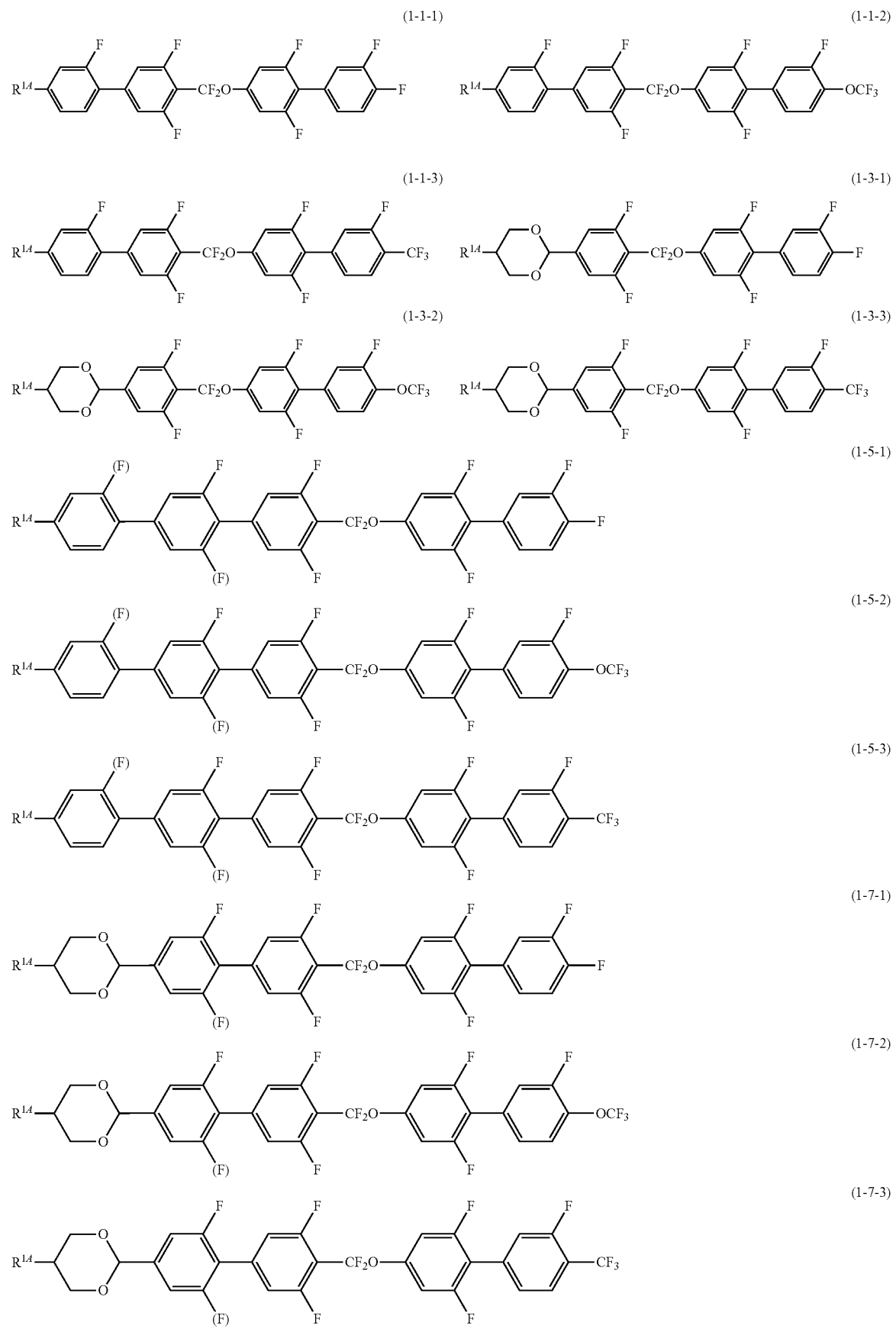

In the above formulae, $R^{14}$ is alkyl having 1 to 12 carbons, and (F) is hydrogen or fluorine.

The compounds represented by formulae (1-1-1) to (1-1-3) have a relatively high clearing point and large dielectric anisotropy. The compounds represented by formulae (1-3-1) to (1-3-3) have extremely large dielectric anisotropy and relatively good compatibility at a low temperature.

The compounds represented by formulae (1-5-1) to (1-5-3) have an extremely high clearing point, large dielectric anisotropy and large refractive index anisotropy. The compounds represented by formulae (1-7-1) to (1-7-3) have an extremely high clearing point and extremely large dielectric anisotropy.

A polymer/liquid-crystal composite material using a liquid crystal composition that contains these compounds has a wide liquid crystal phase temperature range, and a low driving voltage but small permittivity. Therefore, these compounds are useful as a component of the liquid crystal composition.

1-3. Synthesis of Compound (1)

The compound (1) can be synthesized by suitably combining well-known methods in organic synthetic chemistry. There are plural methods for synthesizing the compound (1), and the compound (1) can be appropriately synthesized from a commercially available reagent.

In addition, methods for introducing objective terminal groups, rings and bonding groups into starting materials during synthesis of the compound (1) are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Maruzen Co., Ltd.).

Since synthesis of a compound among the compound (1) in which $Z^3$ is —COO— is easy, regarding the compound (1), an example of a scheme for synthesizing a compound in which $Z^3$ is —CF$_2$O— is shown below. Moreover, synthesis of the compound (1) is not limited to this scheme.

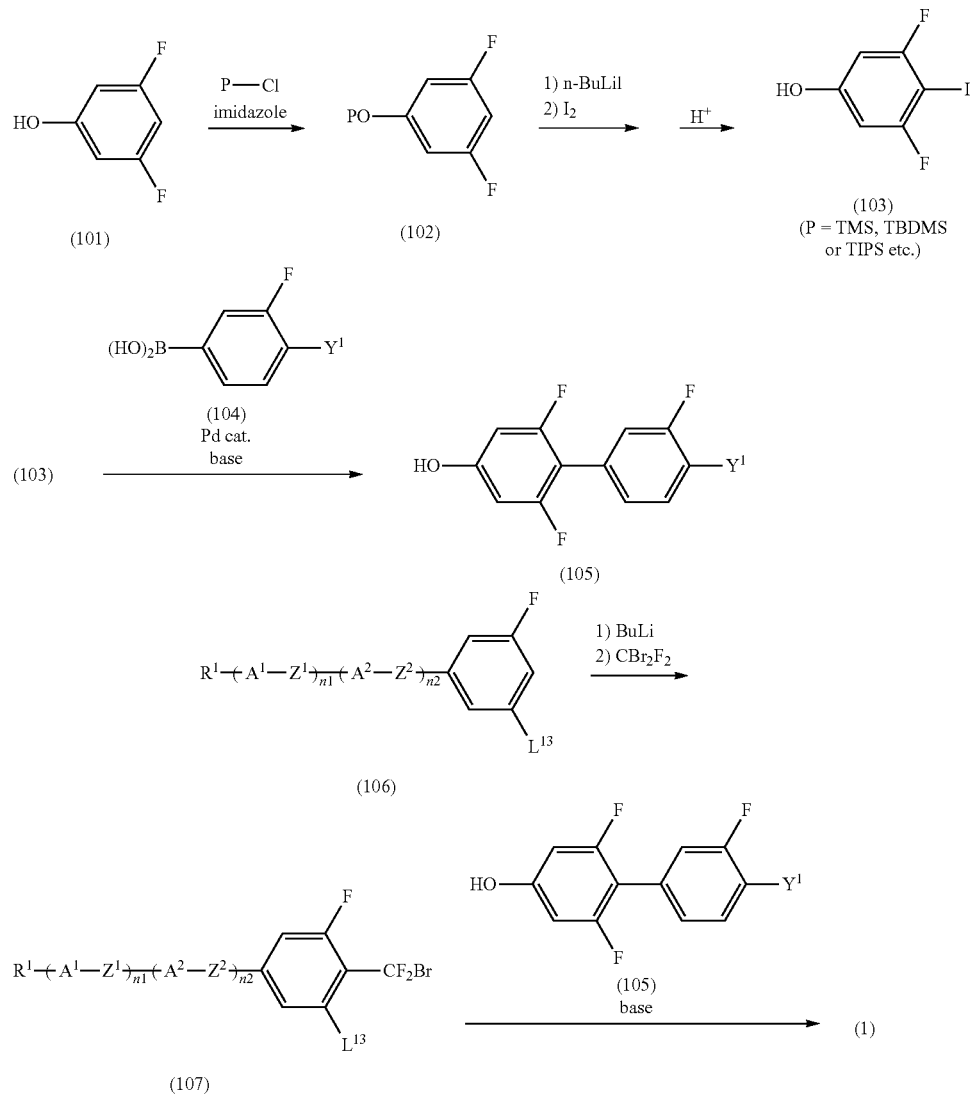

In the scheme, $R^1$, $A^1$, $Z^2$, $L^{13}$, n1, n2 and $Y^1$ are defined as in the case of the compound (1).

Compounds (101), (104) and (106) are commercially available or can be prepared by a general organic chemistry synthesis method. The hydroxyl group of 3,5-difluorophenol (101) is protected using silyl chloride in the presence of a base such as imidazole to obtain a compound (102). A lithium reagent is prepared by using butyl lithium or the like on the compound (102) and then reacted with iodine, and the obtained product is stirred under an acid condition to remove the protecting group and thereby obtain an iodine derivative (103).

A metal catalyst such as palladium is caused to act on a mixture of halogen compounds (103) and (104) in the presence of a base to perform a coupling reaction and thereby obtain a phenol derivative (105).

A lithium reagent is prepared by using butyl lithium or the like on the compound (106) and then reacted with dibromodifluoromethane to obtain a compound (107).

The obtained compound (107) and the phenol derivative (105) are subjected to etherification in the presence of a base to obtain a compound among the compounds (1) which has $Z^3$ being —CF$_2$O—.

2-1. Liquid Crystal Composition

The liquid crystal composition of the invention is a composition containing the compound (1) and exhibiting an optically isotropic liquid crystal phase. In addition, the optically isotropic liquid crystal composition may include, in addition to the achiral component T including the compound (1), a chiral agent, and may further include, an antioxidant, an ultraviolet absorber, a stabilizer and so forth.

The achiral component T includes a composition including one kind of the compound (1), and a liquid crystal composition including two or more kinds of the compound (1). The achiral component T of the invention may further include at least one compound selected from the later-described compounds (2) to (7) if necessary.

The compound (1) has a relatively high clearing point, relatively large dielectric anisotropy, and good compatibility at a low temperature. The achiral component T using the compound (1) shows a wide liquid crystal phase temperature range, and has a low driving voltage but small permittivity. Hence, the optically isotropic liquid crystal composition using the achiral component T is also useful as a composition used for an optical device.

The compound (1) is preferably contained in a total amount of 1 to 60 wt %, more preferably 5 to 40 wt % and particularly preferably 10 to 30 wt % with respect to a total weight of the achiral component T.

2-2. Compound (2)

The achiral component T of the invention may further include, in addition to the compound (1), at least one compound (2). In addition, the liquid crystal composition of the invention may include, in addition to the compound (1), at least one compound selected from the compounds (3) to (7).

are not adjacent to each other and —CO— and —CH═CH— are not adjacent to each other.

$R^2$ is preferably alkyl having 1 to 12 carbons, alkenyl having 2 to 12 carbons, or alkoxy having 1 to 11 carbons.

$A^2$ to $A^{24}$ are each independently 1,4-cyclohexylene, 1,3-dioxane-2,5-diyl, 1,4-phenylene, 1,4-phenylene in which one or two hydrogens are replaced with fluorine, 1,4-phenylene in which two hydrogens are replaced with fluorine and chlorine respectively, pyridine-2,5-diyl, or pyrimidine-2,5-diyl.

$A^{21}$ to $A^{24}$ are preferably 1,4-phenylene, or 1,4-phenylene in which one or two hydrogens are replaced with fluorine, and have great stability or large dielectric anisotropy of the compound.

$Z^{21}$ to $Z^{26}$ are each independently a single bond, or alkylene having 1 to 4 carbons, wherein at least one —CH$_2$— in the alkylene may be replaced with —O—, —COO— or —CF$_2$O—.

It is preferred that all of $Z^{21}$ to $Z^{26}$ are single bonds, or at least one of $Z^{21}$ to $Z^{26}$ is —CF$_2$O—, and $Z^{21}$ to $Z^{26}$ have good compatibility with other liquid crystal compounds. It is particularly preferred that n24=1 and $Z^{25}$ is —CF$_2$O—.

$L^{21}$, $L^{22}$ and $L^{23}$ are each independently hydrogen or fluorine. However, when $Z^{26}$ is a single bond and $L^{21}$ is fluorine, both $L^{22}$ and $L^{23}$ are fluorine. $L^{22}$ and $L^{23}$ are preferably both fluorine and have large dielectric anisotropy.

$X^2$ is fluorine, chlorine, —CF$_3$ or —OCF$_3$, and preferably fluorine or —CF$_3$.

n21, n22, n23 and n24 are each independently 0 or 1, and 1<n21+n22+n23+n24<2.

A compound in which n21+n22+n23+n24=2 has a high clearing point, and a compound in which n21+n22+n23+n24=1 has a low melting point.

The compound (2) has a chlorophenylene ring. The compound (2) is extremely physically and chemically stable under conditions in which the device is normally used, and has good compatibility with other liquid crystal compounds. Furthermore, the compound (2) is unlikely to exhibit a smectic phase. A composition containing this compound is stable under conditions in which the device is normally used.

A compound having objective physical properties can be obtained by suitably selecting types of ring structures, terminal groups, bonding groups and so forth of the compound (2).

Regarding the compound (2), when the bonding groups $Z^{21}$ to $Z^{26}$ are single bonds or —CF$_2$O—, the compound (2) is relatively chemically stable and is relatively unlikely to cause deterioration. Furthermore, when the bonding groups are single bonds, the compound (2) has low viscosity. In (2)

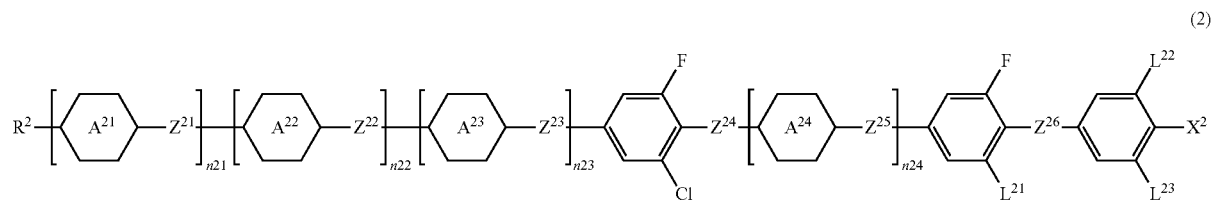

In the compound (2), $R^2$ is hydrogen, or alkyl having 1 to 12 carbons, wherein at least one —CH$_2$— in $R^2$ may be replaced with —O—, —S—, —COO—, —OCO—, —CH═CH—, —CF═CF— or —C≡C—, at least one hydrogen in $R^2$ may be replaced with halogen, or alkyl having 1 to 3 carbons, and in $R^2$, —O— and —CH═CH— addition, when the bonding groups are —CF$_2$O—, the compound (2) has large dielectric anisotropy. When $X^2$ is fluorine, chlorine, or —OCF$_3$, the compound (2) has excellent low-temperature compatibility with other liquid crystal compounds; when $X^2$ is —CF$_3$, the compound (2) has large dielectric anisotropy.

Regarding the compound (2), it is preferred to use a compound represented by formula (2-1).

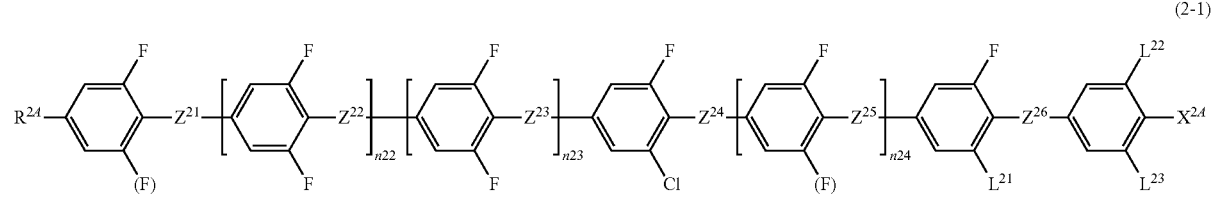

(2-1)

In the formula, $R^{2A}$ is alkyl having 1 to 12 carbons, alkenyl having 2 to 12 carbons, or alkoxy having 1 to 11 carbons; $Z^{21}$, $Z^{22}$, $Z^{23}$, $Z^{24}$, $Z^{25}$ and $Z^{26}$ are each independently a single bond or —CF$_2$O—; $L^{21}$, $L^{22}$ and $L^{23}$ are each independently hydrogen or fluorine; n22, n23 and n24 are each independently 0 or 1, and n22+n23+n24 is an integer of 0 or 1; $X^{2A}$ is fluorine, chlorine, —CF$_3$ or —OCF$_3$; each (F) is independently hydrogen or fluorine.

However, when $Z^{26}$ is a single bond and $L^{21}$ is fluorine, both $L^{22}$ and $L^{23}$ are fluorine.

Regarding the compound (2), it is preferred to use compounds (2-1-1) to (2-1-5).

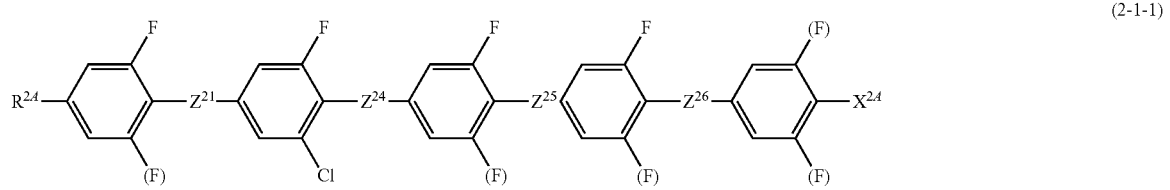

(2-1-1)

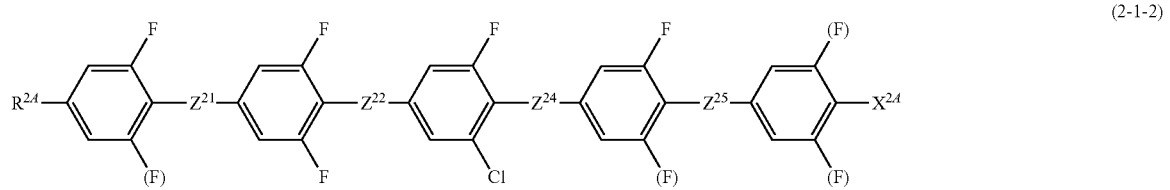

(2-1-2)

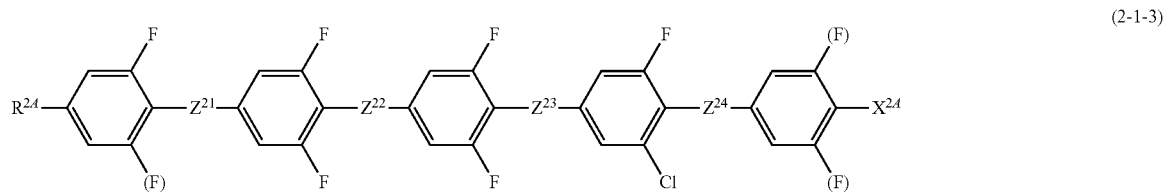

(2-1-3)

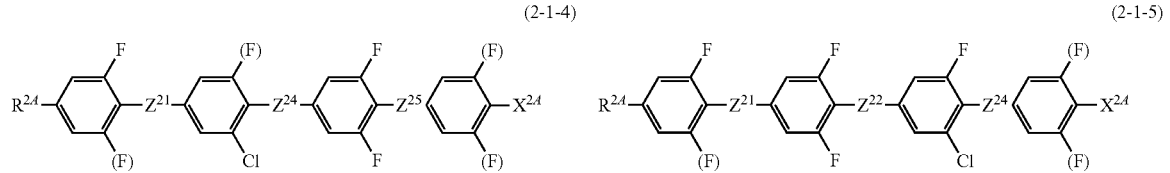

(2-1-4)  (2-1-5)

In the formulae, $R^{2A}$, $X^{2A}$ and (F) have the same meanings as in the compound (2-1).
Regarding the compound (2), it is preferred to use compounds (2-1-1-1) to (2-1-1-3), (2-1-2-1) to (2-1-2-3), (2-1-3-1) to (2-1-3-3), (2-1-4-1) to (2-1-4-3), or (2-1-5-1) to (2-1-5-3), and it is more preferred to use the compounds (2-1-1-1), (2-1-1-2), (2-1-2-1), (2-1-2-2), (2-1-3-1), (2-1-3-2), (2-1-4-2), (2-1-4-3), or (2-1-5-3).
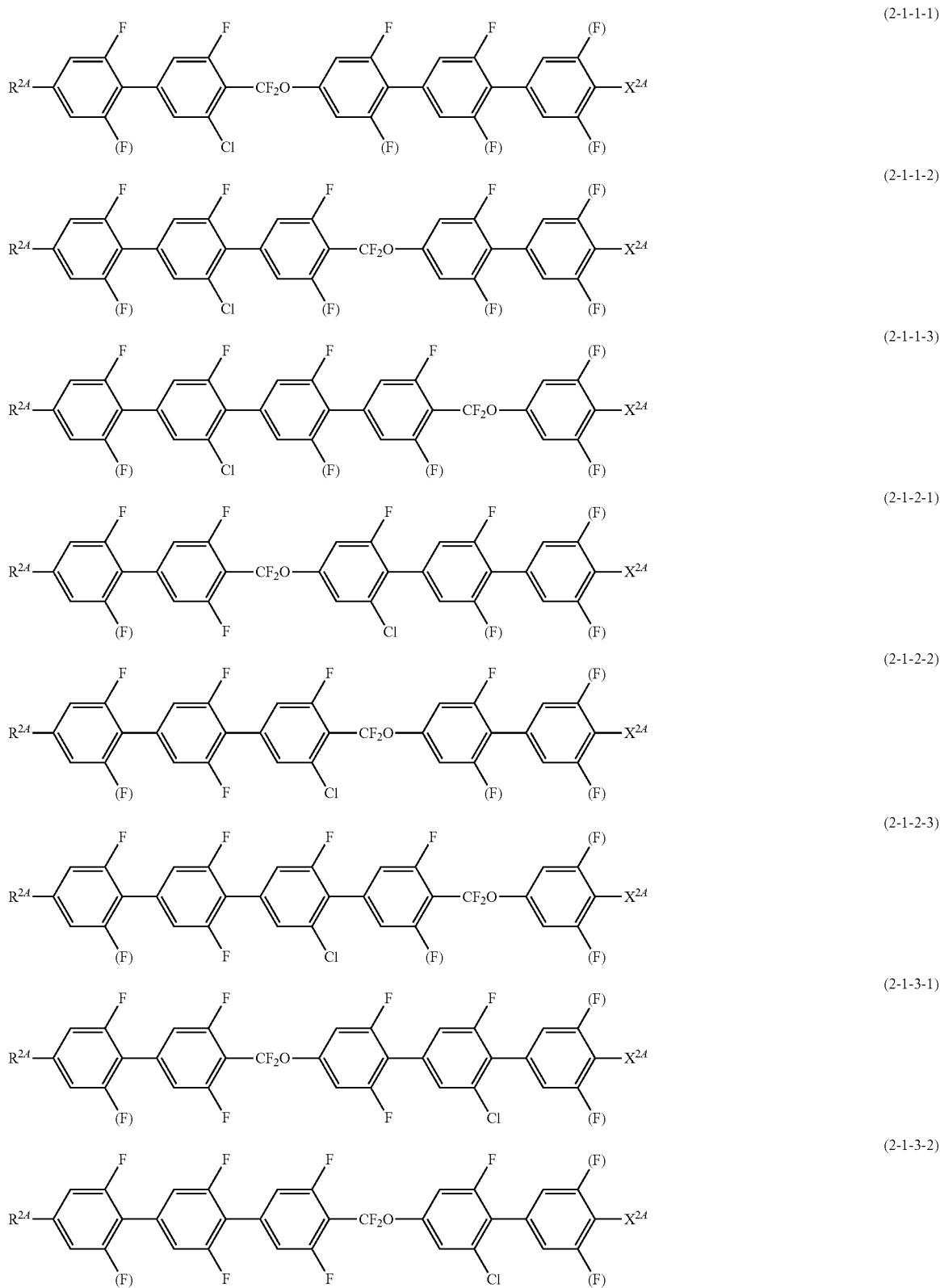

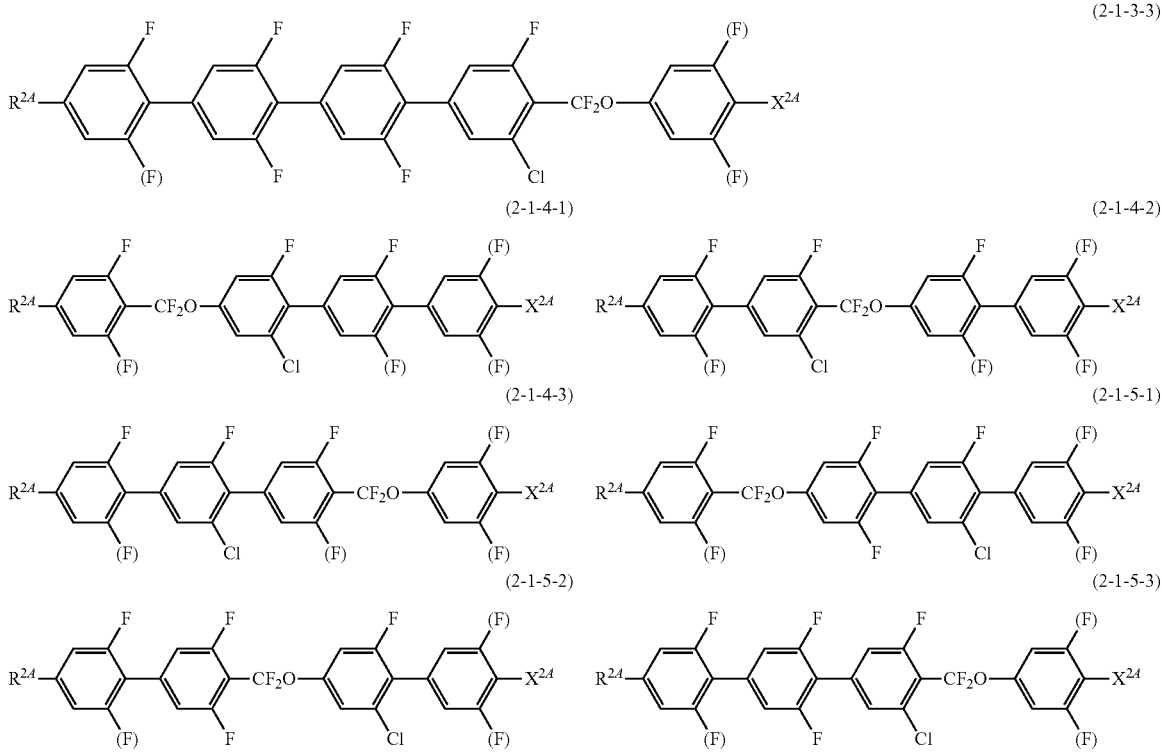

In the above formulae, $R^{2A}$, (F) and $X^{2A}$ have the same meanings as in the compound (2-1).

The compound (2) has good compatibility, large dielectric anisotropy and large refractive index anisotropy. The compound (2) is preferably contained in a total amount of 0.5 to 70 wt %, more preferably 5 to 60 wt % and particularly preferably 10 to 50 wt % with respect to the total weight of the achiral component T.

2-3. Compound (3)

The achiral component T of the invention may further include, in addition to the compound (1), at least one compound (3). In addition, the liquid crystal composition of the invention may include, in addition to the compounds (1) and (3), at least one of the compounds (2), (4) to (7).

$R^3$ is preferably alkyl having 1 to 12 carbons, alkenyl having 2 to 12 carbons, or alkoxy having 1 to 11 carbons.

$Z^{31}$, $Z^{32}$, $Z^{33}$ and $Z^{34}$ are each independently a single bond, or alkylene having 1 to 4 carbons, wherein at least one —$CH_2$— in the alkylene may be replaced with —O—, —COO— or —$CF_2O$—

It is preferred that $Z^{31}$, $Z^{32}$, $Z^{33}$ and $Z^{34}$ are single bonds, —COO— or —$CF_2O$—; it is more preferred that all of $Z^{31}$, $Z^{32}$, $Z^{33}$ and $Z^{34}$ are single bonds, or any one thereof is —$CF_2O$—. Particularly, when n31+n32=2, it is preferred that at least one of $Z^{31}$, $Z^{32}$, $Z^{33}$ and $Z^{34}$ is —$CF_2O$—.

$L^{31}$, $L^{32}$, $L^{33}$, $L^{34}$, $L^{35}$ and $L^{36}$ are hydrogen or fluorine. However, when n32 is 1 and $Z^{34}$ is —COO— or —$CF_2O$—, it is preferred that $L^{32}$ and $L^{35}$ are fluorine; when $Z^{33}$ is

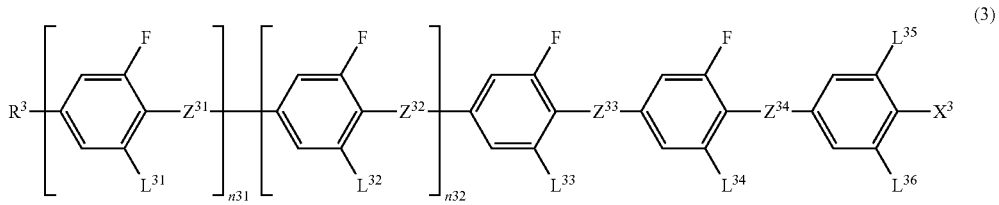

(3)

In the compound (3), $R^3$ is hydrogen, or alkyl having 1 to 12 carbons, wherein at least one —$CH_2$— in $R^3$ may be replaced with —O—, —S—, —COO— or —OCO—, at least one —$CH_2$—$CH_2$— in $R^3$ may be replaced with —CH=CH—, —CF=CF— or —C≡C—, and at least one hydrogen in $R^3$ may be replaced with fluorine or chlorine; however, in $R^3$, —O— and —CH=CH— are not adjacent to each other, and —CO— and —CH=CH— are not adjacent to each other.

—COO— or —$CF_2O$—, it is preferred that $L^{33}$ and $L^{35}$ are fluorine.

$X^3$ is hydrogen, halogen, —$SF_5$, or alkyl having 1 to 10 carbons, wherein at least one —$CH_2$— in $X^3$ may be replaced with —O—, —S—, —COO— or —OCO—, at least one —$CH_2$—$CH_2$— in $X^3$ may be replaced with —CH=CH—, —CF=CF— or —C≡C—, and at least one hydrogen in $X^3$ may be replaced with fluorine or chlorine;

however, in $X^3$, —O— and —CH=CH— are not adjacent to each other, and —CO— and —CH=CH— are not adjacent to each other.

Specific examples of alkyl for $X^3$ in which at least one hydrogen is replaced with halogen include —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, and —$(CF_2)_5$—F.

Specific examples of alkoxy in which at least one hydrogen is replaced with halogen include —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —$O(CH_2)_4$—F, —O—$(CF_2)_4$—F, —O—$(CH_2)_5$—F, and —O—$(CF_2)_5$—F.

Specific examples of alkenyl in which at least one hydrogen is replaced with halogen include —CH=CHF, —CH=$CF_2$, —CF=CHF, —CH=$CHCH_2F$, —CH=$CHCF_3$, —$(CH_2)_2$—CH=$CF_2$, —$CH_2CH$=$CHCF_3$, —CH=$CHCF_3$, and —CH=$CHCF_2CF_3$.

$X^3$ is preferably fluorine, chlorine, —$CF_3$, —$CHF_2$, —$OCF_3$ or —$OCHF_2$, and more preferably fluorine, chlorine, —$CF_3$ or —$OCF_3$.

n31 and n32 are each independently 0 or 1.

However, when $Z^{33}$ is —$CF_2O$— or —COO—, $Z^{34}$ is a single bond and $L^{34}$ is fluorine, both $L^{35}$ and $L^{36}$ are fluorine.

The compound (3) is extremely physically and chemically stable under conditions in which the device is normally used, and has good compatibility with other liquid crystal compounds. A composition containing this compound is stable under conditions in which the device is normally used. The compound (3) has a relatively high clearing point, large dielectric anisotropy and large refractive index anisotropy.

Regarding the compound (3), it is preferred to use compounds (3-1) to (3-3), and it is more preferred to use the compounds (3-2) and (3-3).

(3-1)

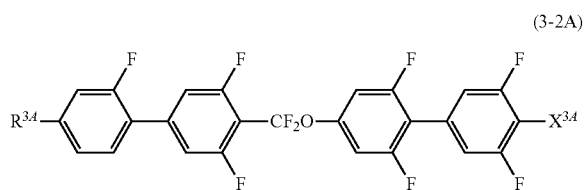

(3-2)

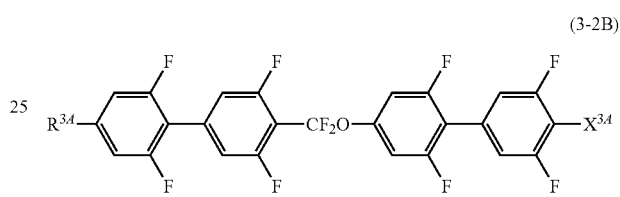

(3-3)

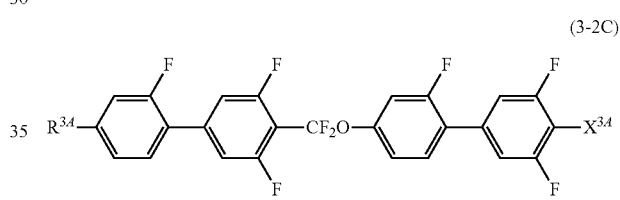

In the formulae, each $R^{34}$ is independently alkyl having 1 to 12 carbons, alkenyl having 2 to 12 carbons, or alkoxy having 1 to 11 carbons; $L^{31}$, $L^{33}$, $L^{34}$ and $L^{36}$ are each independently hydrogen or fluorine; $X^{34}$ is fluorine, chlorine, —$CF_3$ or —$OCF_3$.

Regarding the compound (3-1), it is more preferred to use compounds (3-1A) to (3-2B), and it is particularly preferred to use the compound (3-1A). Regarding the compound (3-2), it is more preferred to use compounds (3-2A) to (3-2F), and it is particularly preferred to use the compound (3-2C).

Regarding the compound (3-3), it is more preferred to use compounds (3-3A) to (3-3D), it is particularly preferred to use the compounds (3-3A) and (3-3C), and it is most preferred to use the compound (3-3A).

(3-2A)

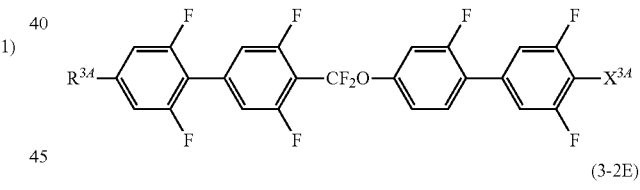

(3-2B)

(3-2C)

(3-2D)

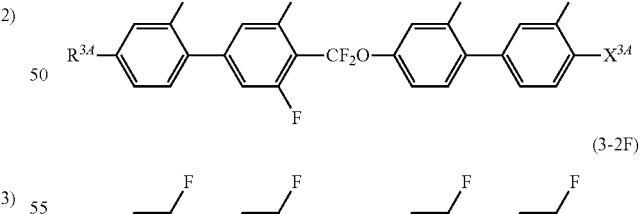

(3-2E)

(3-2F)

(3-3A)

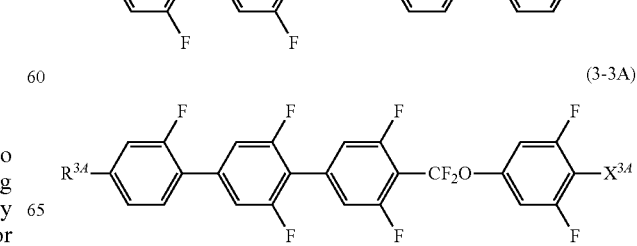

-continued

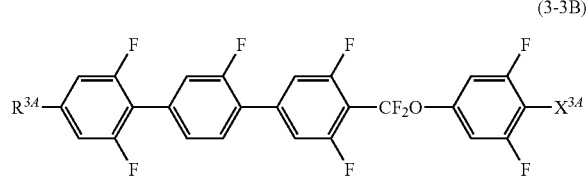

(3-3B)

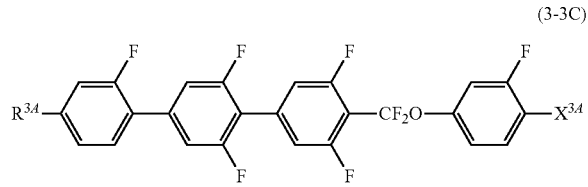

(3-3C)

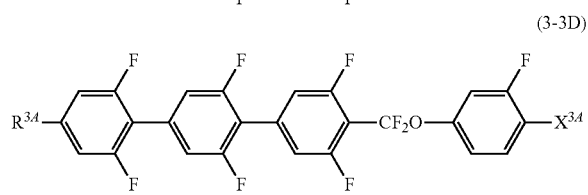

(3-3D)

In the above formulae, $R^{3A}$ is independently alkyl having 1 to 12 carbons, alkenyl having 2 to 12 carbons, or alkoxy having 1 to 11 carbons; $X^{3A}$ is fluorine, chlorine, —$CF_3$ or —$OCF_3$.

The compound (3) is preferably contained in a total amount of 0.5 to 70 wt %, more preferably 5 to 60 wt % and particularly preferably 10 to 50 wt % with respect to the total weight of the achiral component T.

Regarding the compound (3), physical properties such as clearing point, refractive index anisotropy, dielectric anisotropy and so forth can be arbitrarily adjusted by suitably selecting $R^3$, the groups ($L^{31}$ to $L^{36}$ and $X^3$) on the phenylene ring, or $Z^{31}$ to $Z^{34}$.

When there is a large number of fluorine atoms in $L^{31}$ to $L^{36}$, the compound (3) has large dielectric anisotropy. When $L^{31}$ is hydrogen, the compound (3) has excellent compatibility with other liquid crystals. When both $L^{35}$ and $L^{36}$ are fluorine, the compound (3) has particularly large dielectric anisotropy.

When $Z^{31}$ to $Z^{34}$ are single bonds or —$CF_2O$—, the compound (3) has low viscosity and is chemically stable. When any one of $Z^{31}$ to $Z^{34}$ is —$CF_2O$—, the compound (3) has large dielectric anisotropy.

When $X^3$ is fluorine, chlorine, —$SF_5$, —$CF_3$, —$CHF_2$, —$CH_2F$, —$OCF_3$, —$OCHF_2$ or —$OCH_2F$, the compound (3) has large dielectric anisotropy. When $X^3$ is fluorine, —$OCF_3$ or —$CF_3$, the compound (3) is particularly chemically stable.

When n31+n32=0, the compound (3) has a low clearing point, low viscosity and good compatibility with other liquid crystal compounds. When n31+n32=1, the compound (3) has a relatively high clearing point, large dielectric anisotropy and large refractive index anisotropy. In addition, when n31+n32=1, the compound (3) has a very high clearing point, large dielectric anisotropy and extremely large refractive index anisotropy.

2-4. Compound (4)

The achiral component T of the invention may further include, in addition to the compound (1), at least one compound (4). In addition, the liquid crystal composition of the invention may include, in addition to the compounds (1) and (4), at least one of the compounds (2), (3), and (5) to (7).

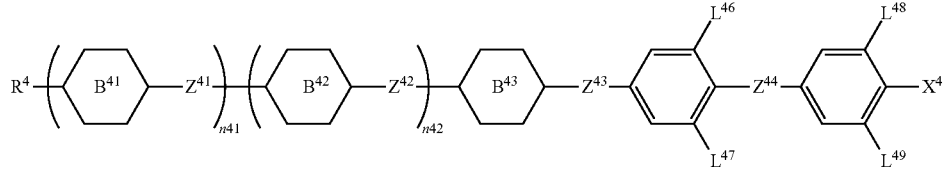

(4)

In the compound (4), $R^4$ is alkyl having 1 to 12 carbons, alkenyl having 2 to 12 carbons, or alkoxy having 1 to 11 carbons.

$B^{41}$, $B^{42}$ and $B^{43}$ are each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2,5-diyl. However, a situation where all of $B^{41}$, $B^{42}$ and $B^{43}$ are fluorine-substituted 1,4-phenylene does not exist.

In order to increase optical anisotropy, $B^{41}$, $B^{42}$ and $B^{43}$ are preferably 1,4-phenylene, 3-fluoro-1,4-phenylene or 3,5-difluoro-1,4-phenylene; in order to reduce viscosity, $B^{41}$, $B^{42}$ and $B^{43}$ are preferably 1,4-cyclohexylene.

$Z^{41}$, $Z^{42}$, $Z^{43}$ and $Z^{44}$ are each independently a single bond, ethylene, —COO—, —OCO—, —$CF_2O$— or —$OCF_2$—. In order to increase dielectric anisotropy and to improve compatibility, it is preferred that any one of $Z^{41}$, $Z^{42}$, $Z^{43}$ and $Z^{44}$ is —$CF_2O$—. When $Z^{41}$, $Z^{42}$, $Z^{43}$ and $Z^{44}$ are single bonds, the compound (4) has low viscosity.

$L^{46}$, $L^{47}$, $L^{48}$ and $L^{49}$ are each independently hydrogen or fluorine. When $Z^{43}$ is —$CF_2O$— or —COO—, $Z^{44}$ is a single bond and both $L^{46}$ and $L^{47}$ are fluorine, both $L^{48}$ and $L^{49}$ are fluorine. When both $L^{48}$ and $L^{49}$ are fluorine, the compound (4) has large dielectric anisotropy. When both $L^{47}$ and $L^{49}$ are hydrogen, the compound (4) has a high clearing point.

$X^4$ is fluorine, chlorine, —$CF_3$ or —$OCF_3$. When $X^4$ is fluorine or —$CF_3$, the compound (4) has large dielectric anisotropy. When $X^4$ is fluorine or —$OCF_3$, the compound (4) has good compatibility with compounds. When $X^4$ is chlorine, the compound (4) has large refractive index anisotropy.

n41 and n42 are each independently 0 or 1. When n41+n42=1 and $Z^{43}$ is —$CF_2O$—, it is preferred that both $L^{48}$ and $L^{49}$ are fluorine. When n41+n42 is 1 or 2, it is particularly preferred that any one of $Z^{41}$, $Z^{42}$, $Z^{43}$ and $Z^{44}$ is —$CF^2O$—.

Regarding the compound (4), it is preferred to use compounds (4-1) to (4-10).

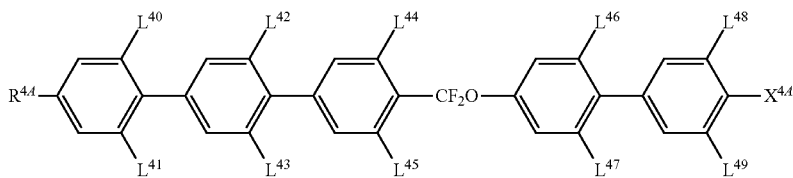

(4-1)

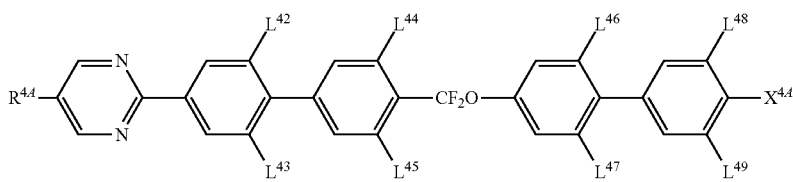

(4-2)

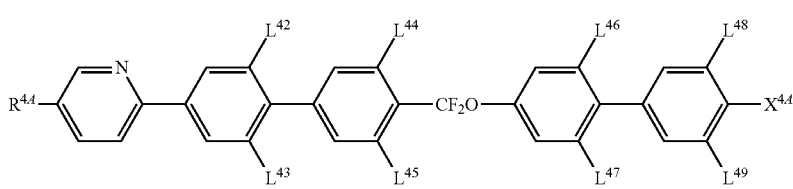

(4-3)

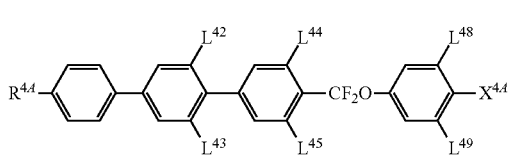

(4-4)

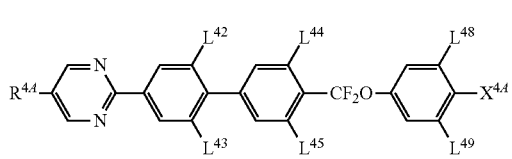

(4-5)

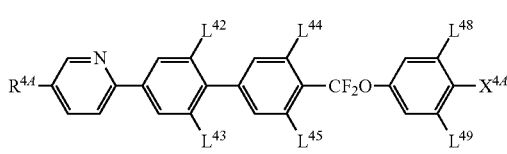

(4-6)

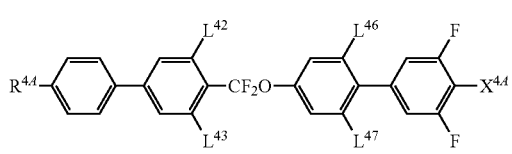

(4-7)

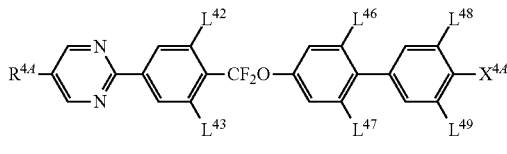

(4-8)

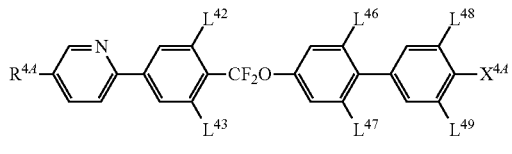

(4-9)

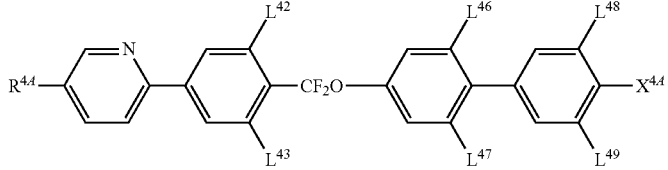

(4-10)

In formulae (4-1) to (4-10), each $R^{4.4}$ is independently alkyl having 1 to 12 carbons, alkenyl having 2 to 12 carbons, or alkoxy having 1 to 11 carbons; $X^{4.4}$ is fluorine, chlorine, —$CF_3$ or —$OCF_3$; $L^{40}$ to $L^{49}$ are each independently hydrogen or fluorine, wherein when both $L^{46}$ and $L^{47}$ are fluorine, both $L^{48}$ and $L^{49}$ are fluorine.

The compounds (4-1) to (4-3) have a high clearing point, and excellent compatibility as a pentacyclic compound. The compounds (4-4) to (4-6) have a high clearing point and large refractive index anisotropy; the compounds (4-7) to (4-10) have excellent compatibility. Moreover, in $L^{40}$ to $L^{49}$, the larger the number of fluorine atoms, the larger the dielectric anisotropy.

The compound (4) is suitable for preparation of a composition having large dielectric anisotropy or good compatibility at a low temperature. The compound (4) is preferably contained in a total amount of 5 to 40 wt %, more preferably 5 to 30 wt % and particularly preferably 5 to 20 wt % with respect to the total weight of the achiral component T.

2-5. Compound (5)

The achiral component T of the invention may further include, in addition to the compound (1), at least one compound (5). In addition, the liquid crystal composition of the invention may include, in addition to the compounds (1) and (5), at least one compound selected from the compounds (2) to (4), (6) and (7).

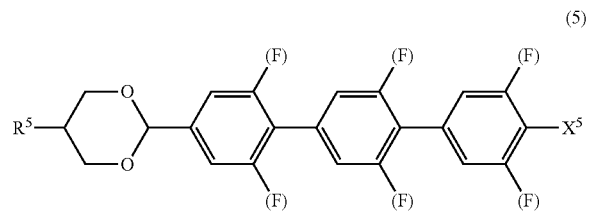

(5)

In the compound (5), $R^5$ is hydrogen, or alkyl having 1 to 12 carbons, wherein at least one —$CH_2$— in $R^5$ may be replaced with —O—, —S—, —COO— or —OCO—, at least one —$CH_2$—$CH_2$— in $R^5$ may be replaced with —CH=CH—, —CF=CF— or —C≡C—, and at least one hydrogen in $R^5$ may be replaced with fluorine or chlorine; however, in $R^5$, —O— and —CH=CH— are not adjacent to each other, and —CO— and —CH=CH— are not adjacent to each other.

$X^5$ is hydrogen, halogen, —$SF_5$, or alkyl having 1 to 10 carbons, wherein at least one —$CH_2$— in $X^5$ may be replaced with —O—, —S—, —COO— or —OCO—, at least one —$CH_2$—$CH_2$— in $X^5$ may be replaced with —CH=CH—, —CF=CF— or —C≡C—, and at least one hydrogen in $X^5$ may be replaced with fluorine or chlorine; however, in $X^5$, —O— and —CH=CH— are not adjacent to each other, and —CO— and —CH=CH— are not adjacent to each other.

Specific examples of $X^5$ include fluorine, chlorine, —$CF_3$, —$CHF_2$, —$OCF_3$ and —$OCHF_2$, wherein fluorine, chlorine, —$CF_3$ and —$OCF_3$ are preferred. When $X^5$ is chlorine or fluorine, the compound (5) has a relatively low melting point and particularly excellent compatibility with other liquid crystal compounds. When $X^5$ is —$CF_3$, —$CHF_2$, —$OCF_3$ or —$OCHF_2$, the compound (5) shows relatively large dielectric anisotropy.

When $X^5$ is fluorine, chlorine, —$SF_5$, —$CF_3$, —$OCF_3$ or —CH=CH—$CF_3$, the compound (5) has relatively large dielectric anisotropy; when $X^5$ is fluorine, —$CF_3$ or —$OCF_3$, the compound (5) is particularly chemically stable.

Each (F) is independently hydrogen or fluorine.

Regarding $R^5$ or $X^5$, specific examples of alkyl in which at least one hydrogen is replaced with fluorine include —$CHF_2$, —$CF_3$, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, and —$CHFCF_2CF_3$.

Regarding $R^5$ and $X^5$, specific examples of alkoxy in which at least one hydrogen is replaced with fluorine include —$OCHF_2$, —$OCF_3$, —$OCF_2CH_2F$, —$OCF_2CHF_2$, —$OCH_2CF_3$, —O—$(CF_2)_3$—F, —$OCF_2CHFCF_3$, and —$OCHFCF_2CF_3$.

Regarding $R^5$ and $X^5$, specific examples of alkenyl in which at least one hydrogen is replaced with fluorine include —CH=$CF_2$, —CF=CHF, —CH=$CHCH_2$F, —CH=$CHCF_3$, —$(CH_2)_2$—CH=$CF_2$, —$CH_2$CH=$CHCF_3$, and —CH=$CHCF_2CF_3$.

The compound (5) has a dioxane ring and three phenylene rings. The compound (5) is extremely physically and chemically stable under conditions in which the device is normally used, and has relatively good compatibility with other liquid crystal compounds in spite of a high clearing point. A composition containing the compound (5) is stable under conditions in which the device is normally used. Accordingly, in the case of the composition containing the compound (5), a temperature range of the optically isotropic liquid crystal phase can be extended, and the composition can be used as a display device in a wide temperature range. In addition, the compound (5) is useful as a component for reducing a driving voltage of a composition driven in the optically isotropic liquid crystal phase. If a blue phase is exhibited in a composition according to a preferred aspect including a chiral agent and the compound (5), a uniform blue phase without coexistence with a N*phase or an isotropic phase is formed. In this way, the composition according to a preferred aspect including the compound (5) easily exhibits the uniform blue phase. In addition, if the compound (5) is used, the clearing point of the liquid crystal composition tends to rise.

Regarding the compound (5), it is preferred to use compounds (5-1) to (5-4), and it is more preferred to use the compounds (5-1) to (5-3). Among these compounds, it is particularly preferred to use compounds (5-1-1), (5-1-2), (5-2-1) to (5-2-4), (5-3-1), or (5-3-2), and it is most preferred to use the compound (5-2-1), (5-2-2), or (5-3-2).

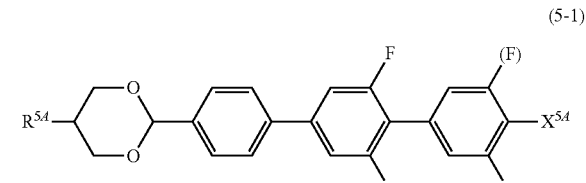

(5-1)

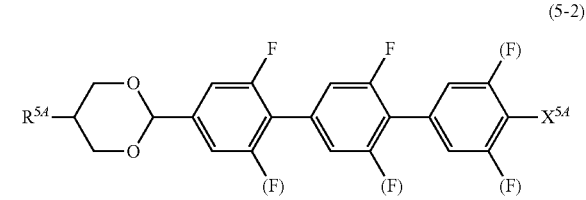

(5-2)

(5-3)
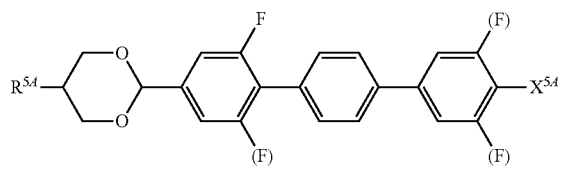

(5-4)
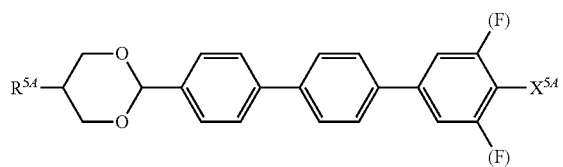

(5-1-1)
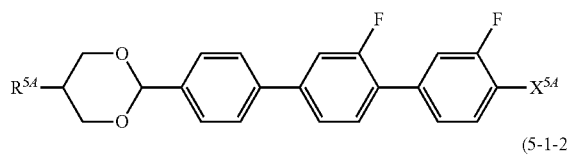

(5-1-2)
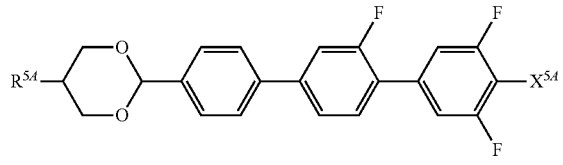

(5-2-1)
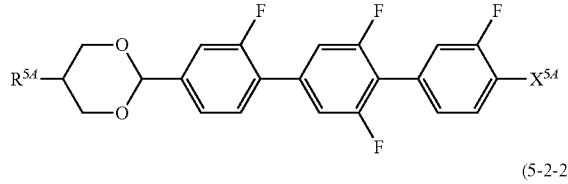

(5-2-2)
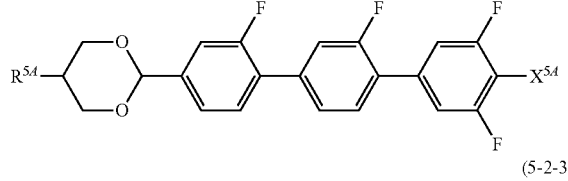

(5-2-3)
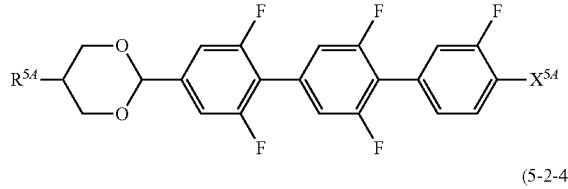

(5-2-4)
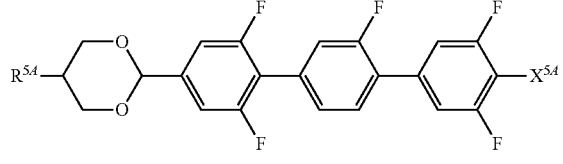

(5-3-1)
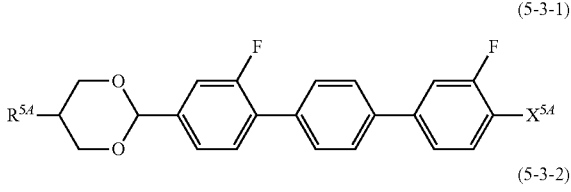

(5-3-2)
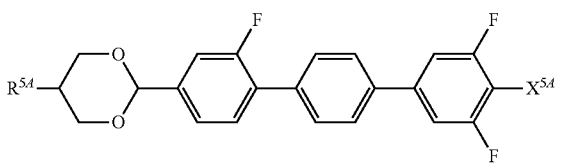

In the formulae, $R^{5A}$ is alkyl having 1 to 12 carbons, alkenyl having 2 to 12 carbons, or alkoxy having 1 to 11 carbons; each (F) is independently hydrogen or fluorine; $X^{5A}$ is fluorine, chlorine, —$CF_3$ or —$OCF_3$.

The compound (5) is suitable for preparation of a composition having large dielectric anisotropy. In order to raise the clearing point, the compound (5) is preferably contained in a total amount of approximately 1.0 wt % or more with respect to the total weight of the achiral component T. In addition, in order to lower the lower-limit temperature of the liquid crystal phase, the compound (5) is preferably contained in a total amount of 1 to 50 wt % with respect to the total weight of the achiral component T. Furthermore, the compound (5) is preferably contained in a total amount of 1 to 25 wt %, and more preferably 1 to 15 wt % with respect to the total weight of the achiral component T.

2-6. Compound (6)

The achiral component T of the invention may further include, in addition to the compound (1), one or more compounds (6). In addition, the liquid crystal composition of the invention may include, in addition to the compounds (1) and (6), one or more of the compounds (2) to (5) and (7).

(6)
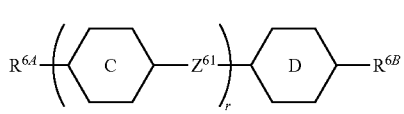

In the compound (6), r is 1, 2 or 3.

Regarding the compound (6), a compound in which r is 1 mainly has an effect of adjusting viscosity or refractive index anisotropy; a compound in which r is 2 or 3 has an effect of extending a temperature range of the optically isotropic liquid crystal phase such as raising the clearing point or the like, or an effect of adjusting refractive index anisotropy.

If the content of the compound (6) is increased, a driving voltage of the liquid crystal composition is increased and viscosity is reduced. Therefore, the content is desirably as small as possible from a viewpoint of the driving voltage, as long as a required value of viscosity of the liquid crystal composition is satisfied. The compound (6) is preferably contained in an amount of 0 to 40 wt %, more preferably 1 to 40 wt % and particularly preferably 1 to 20 wt % with respect to the total weight of the achiral component T.

$R^{6A}$ and $R^{6B}$ are each independently alkyl having 1 to 12 carbons, alkenyl having 2 to 12 carbons, alkoxy having 1 to 12 carbons, or alkenyl having 2 to 12 carbons in which at least one hydrogen is replaced with fluorine. In order to reduce viscosity of the compound (6), $R^{6A}$ and $R^{6B}$ in the compound (6) are preferably alkenyl having 2 to 12 carbons. In order to increase stability with respect to ultraviolet light or heat, $R^{6A}$ and $R^{6B}$ are preferably alkyl having 1 to 12 carbons.

In order to reduce viscosity, the alkyl in $R^{6A}$ and $R^{6B}$ is preferably ethyl, propyl, butyl, pentyl or heptyl.

In order to reduce viscosity, the alkoxy in $R^{6A}$ and $R^{6B}$ is preferably methoxy or ethoxy.

Regarding $R^{6A}$ and $R^{6B}$, the alkenyl in which at least one hydrogen is replaced with fluorine is preferably 2,2-difluorovinyl, 3,3-difluoro-2-propenyl, 4,4-difluoro-3-butenyl, 5,5-difluoro-4-pentenyl, or 6,6-difluoro-5-hexenyl.

In order to reduce viscosity of a composition including the compound (6), $R^{6A}$ and $R^{6B}$ are preferably 2,2-difluorovinyl or 4,4-difluoro-3-butenyl.

Rings C and D are each independently 1,4-cyclohexylene, 1,4-phenylene, 2-fluoro-1,4-phenylene, 3-fluoro-1,4-phenylene, or 2,5-difluoro-1,4-phenylene. When r is 2 or greater, at least two rings C may be the same or different. In order to increase optical anisotropy of the compound (6), ring C and ring D are preferably 1,4-phenylene or 3-fluoro-1,4-phenylene. In order to reduce viscosity of the compound (6), ring C and ring D are 1,4-cyclohexylene.

Each $Z^{61}$ in the compound (6) is independently a single bond, ethylene, —COO— or —OCO—. When r is 2 or greater, at least two $Z^{61}$ may be the same or different. In order to reduce viscosity, $Z^{61}$ is preferably a single bond.

The compound (6) has a small absolute value of dielectric anisotropy, and is a nearly neutral compound.

Regarding the compound (6), it is preferred to use compounds represented by formulae (6-1) to (6-13).

(6-1)

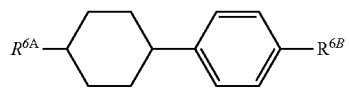
(6-2)

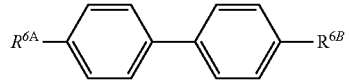
(6-3)

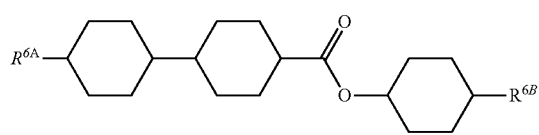
(6-4)

(6-5)

(6-6)

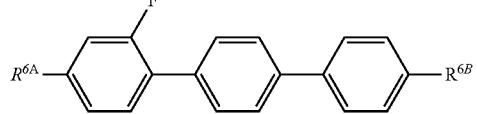
(6-7)

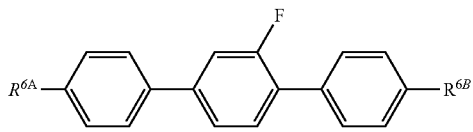
(6-8)

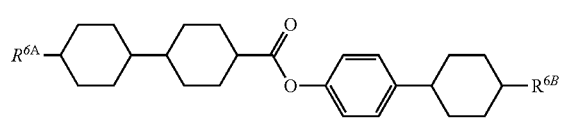
(6-9)

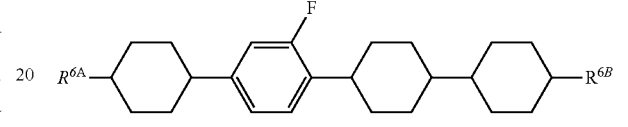
(6-10)

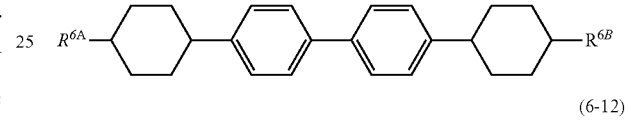
(6-11)

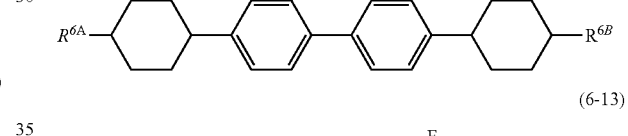
(6-12)

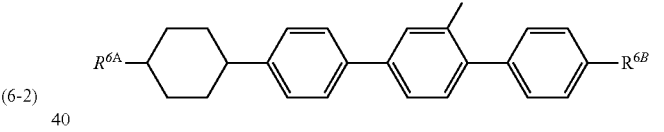
(6-13)

In the formulae, $R^{6A}$ and $R^{6B}$ are each independently alkyl having 1 to 12 carbons, alkenyl having 2 to 12 carbons, alkoxy having 1 to 11 carbons, or alkenyl having 2 to 12 carbons in which at least one hydrogen is replaced with fluorine.

Among these compounds, the compounds (6-1) to (6-3) have relatively low viscosity, the compounds (6-4) to (6-8) have a relatively high clearing point, and the compounds (6-9) to (6-13) have a relatively high clearing point.

The compound (6) is used for reducing viscosity or for raising the clearing point, if necessary. However, since the compound (6) causes a driving voltage to rise, if the driving voltage is considered important, it is preferred to not use the compound (6) or to use a small amount thereof. The compound (6) is preferably contained in a total amount of 0 to 30 wt %, more preferably 0 to 20 wt % and particularly preferably 0 to 10 wt %.

2-7-1. Compound (7)

The achiral component (T) of the invention may further include, in addition to the compound (1), at least one compound (7). In addition, the liquid crystal composition of the invention may include, in addition to the compounds (1) and (7), at least one compound selected from the compounds (2) to (6).

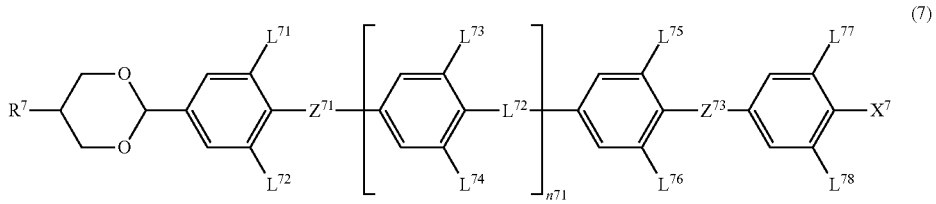
(7)

In the compound (7), R$^7$ is hydrogen, or alkyl having 1 to 12 carbons, wherein at least one —CH$_2$— in R$^7$ may be replaced with —O—, —S—, —COO— or —OCO—, at least one —CH$_2$—CH$_2$— in R$^7$ may be replaced with —CH═CH—, —CF═CF— or —C≡C—, and at least one hydrogen in R$^7$ may be replaced with fluorine or chlorine; however, in R$^7$, —O— and —CH═CH— are not adjacent to each other, and —CO— and —CH═CH— are not adjacent to each other. R$^7$ is preferably alkyl having 1 to 12 carbons.

L$^{71}$ to L$^{78}$ are each independently hydrogen or fluorine.

However, when n71=1, Z$^{72}$ is —CF$_2$O— or —COO—, Z$^{73}$ is a single bond, and both L$^{75}$ and L$^{76}$ are fluorine, both L$^{77}$ and L$^{78}$ are fluorine. In addition, when n71=0, Z$^{71}$ is —CF$_2$O— or —COO—, Z$^{73}$ is a single bond, and both L$^{75}$ and L$^{76}$ are fluorine, both L$^{77}$ and L$^{78}$ are fluorine.

The compound (7) in which L$^{72}$ is hydrogen has good compatibility with compounds. The compound (7) in which both L$^{77}$ and L$^{78}$ are fluorine has large dielectric anisotropy, which is preferred.

Z$^{71}$, Z$^{72}$ and Z$^{73}$ are each independently a single bond, —COO— or —CF$_2$O—. The compound (7) in which any of Z$^{71}$, Z$^{72}$ and Z$^{73}$ is —CF$_2$O— has large dielectric anisotropy and good compatibility with other compounds, which is preferred.

X$^7$ is hydrogen, halogen, —SF$_5$, or alkyl having 1 to 10 carbons, wherein at least one —CH$_2$— in X$^7$ may be replaced with —O—, —S—, —COO— or —OCO—, at least one —CH$_2$—CH$_2$— in X$^7$ may be replaced with —CH═CH—, —CF═CF— or —C≡C—, and at least one hydrogen in X$^7$ may be replaced with fluorine or chlorine; however, in X$^7$, —O— and —CH═CH— are not adjacent to each other, and —CO— and —CH═CH— are not adjacent to each other.

Regarding X$^7$, specific examples of alkyl in which at least one hydrogen is replaced with fluorine include —CHF$_2$, —CF$_3$, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, and —CHFCF$_2$CF$_3$.

Regarding X$^7$, specific examples of alkoxy in which at least one hydrogen is replaced with fluorine include —OCHF$_2$, —OCF$_3$, —OCF$_2$CH$_2$F, —OCF$_2$CHF$_2$, —OCH$_2$CF$_3$, —O—(CF$_2$)$_3$—F, —OCF$_2$CHFCF$_3$, and —OCHFCF$_2$CF$_3$.

Regarding X$^7$, specific examples of alkenyl in which at least one hydrogen is replaced with fluorine include —CH═CF$_2$, —CF═CHF, —CH═CHCH$_2$F, —CH═CHCF$_3$, —(CH$_2$)$_2$—CH═CF$_2$, —CH$_2$CH═CHCF$_3$, and —CH═CHCF$_2$CF$_3$.

Preferred specific examples of X$^7$ include fluorine, chlorine, —CF$_3$, —CHF$_2$, —OCF$_3$ and —OCHF$_2$, wherein fluorine, chlorine, —CF$_3$ and —OCF$_3$ are more preferred. When X$^7$ is chlorine or fluorine, the compound (7) has a relatively low melting point, and has particularly excellent compatibility with other liquid crystal compounds. When X$^7$ is —CF$_3$, —SF$_5$, —CHF$_2$, —OCF$_3$ or —OCHF$_2$, the compound (7) shows relatively large dielectric anisotropy.

When X$^7$ is fluorine, —CF$_3$, or —OCF$_3$, the compound (7) is chemically stable.

n71 is 0 or 1. The compound (7) in which n71=1 has large dielectric anisotropy and a high clearing point. The compound (7) in which n71=0 has large dielectric anisotropy, and good compatibility with other compounds.

The compound (7) has a dioxane ring, two to four phenylene rings and at least one —CF$_2$O— or —COO— linking group. The compound (7) is extremely physically and chemically stable under conditions in which the device is normally used, and has relatively good compatibility with other liquid crystal compounds in spite of a high clearing point. A composition containing the compound (7) is relatively stable under conditions in which the device is normally used. Accordingly, in the case of the composition containing the compound (7), a temperature range of the optically isotropic liquid crystal phase can be extended, and the composition can be used as a display device in a wide temperature range.

Furthermore, the compound (7) is useful as a component for reducing a driving voltage of a composition driven in the optically isotropic liquid crystal phase. In addition, if a blue phase is exhibited in a composition including the compound (7) and a chiral agent, a uniform blue phase without coexistence with a N*phase or an isotropic phase is easily formed. That is, the compound (7) is a compound easily exhibiting a uniform blue phase. In addition, the compound (7) exhibits extremely large dielectric anisotropy.

Regarding the compound (7), it is preferred to use compounds (7-1) to (7-8), it is more preferred to use compounds (7-1-1), (7-1-2), (7-2-1) to (7-2-7), (7-3-1) to (7-3-4), (7-4-1), (7-5-1), or (7-5-2), it is even more preferred to use the compounds (7-2-1) to (7-2-7), and it is particularly preferred to use compounds (7-2-2-E), (7-2-5-E), (7-2-7-E), (7-2-2-F), (7-2-5-F), (7-2-6-F), or (7-2-7-F).

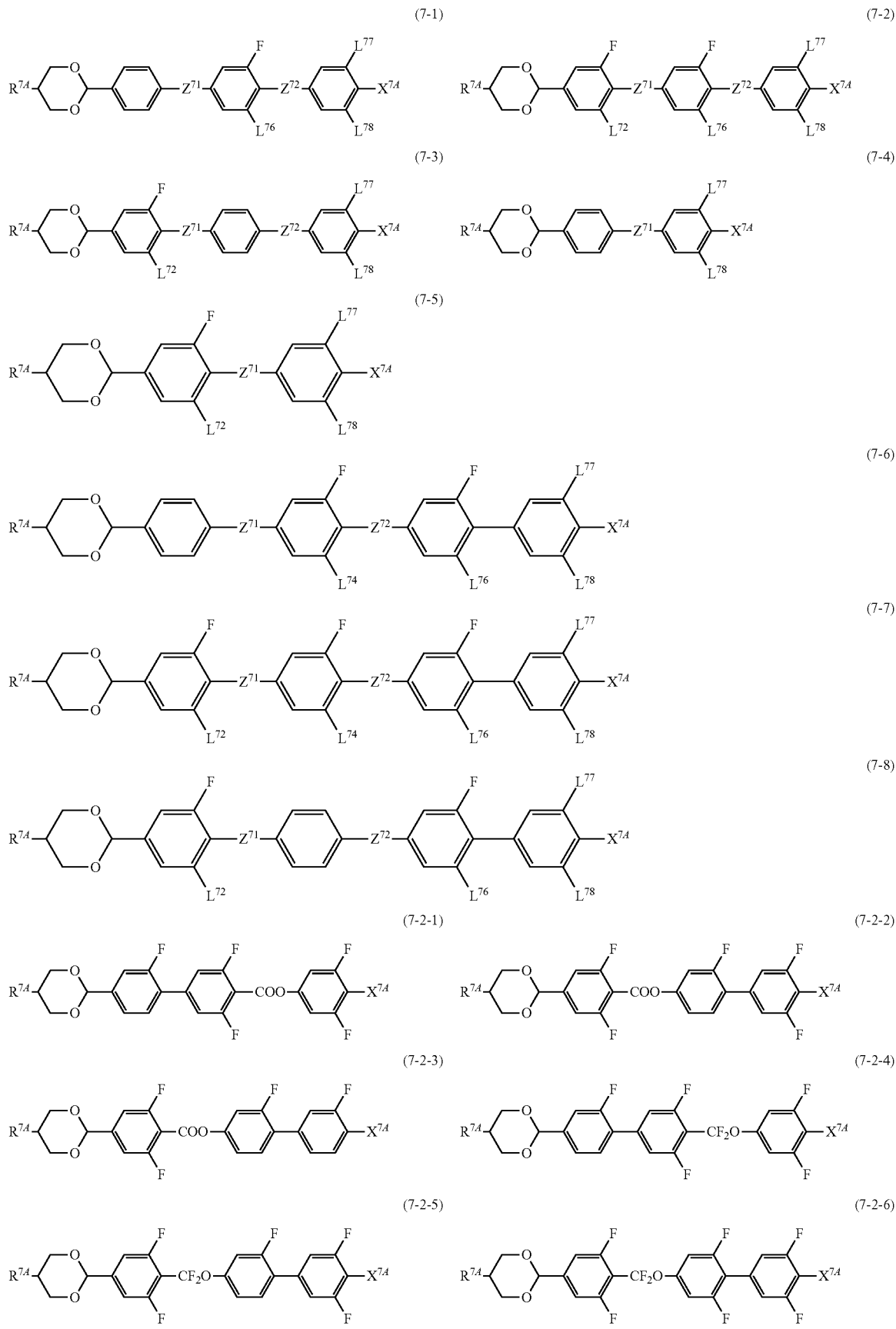

(7-2-7) 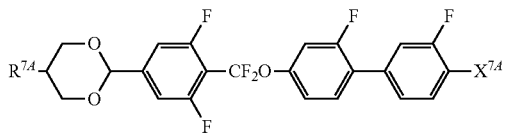

(7-2-2-E) 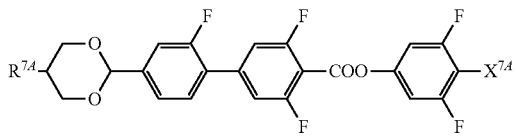

(7-2-5-E) 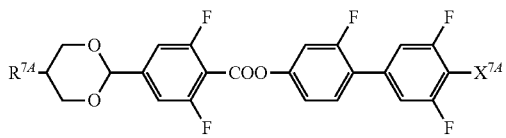

(7-2-7-E) 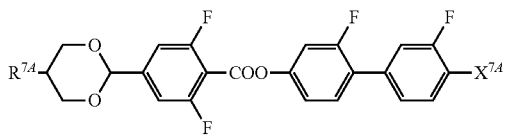

(7-2-2-F) 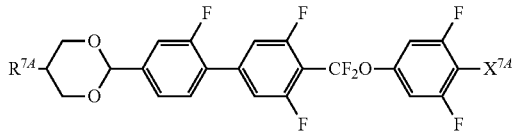

(7-2-5-F) 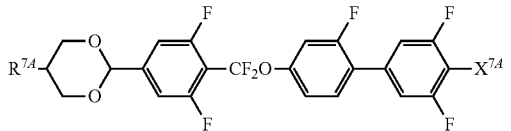

(7-2-6-F) 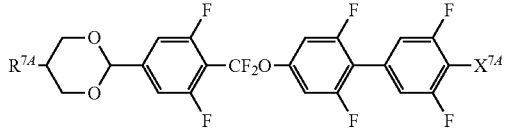

(7-2-7-F) 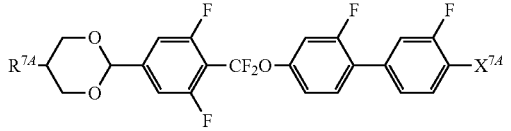

(7-4-1) 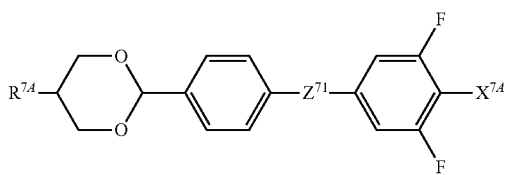

(7-5-1) 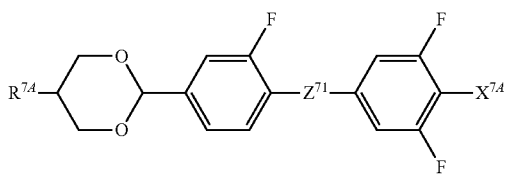

(7-5-2) 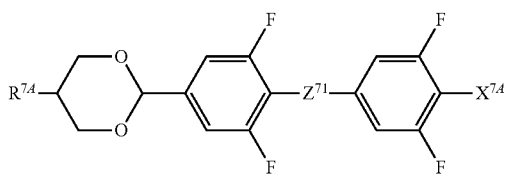

In the formulae, $R^{74}$ is alkyl having 1 to 12 carbons, alkenyl having 2 to 12 carbons, alkoxy having 1 to 11 carbons, or alkenyl having 2 to 12 carbons in which at least one hydrogen is replaced with fluorine; $X^{74}$ is fluorine, chlorine, —$CF_3$ or —$OCF_3$; $Z^{71}$ and $Z^{72}$ are each independently a single bond, —COO— or —$CF_2$O—, wherein at least one of $Z^{71}$ and $Z^{72}$ is —COO— or —$CF_2$O—; however, when $L^{76}$ is fluorine, both $L^{77}$ and $L^{78}$ are fluorine.

The compound (7) is suitable for preparation of a composition having large dielectric anisotropy, and is capable of reducing a driving voltage in a device of the invention. The compound (7) is preferably contained in a total amount of 5 to 80 wt %, more preferably 20 to 75 wt % and particularly preferably 30 to 70 wt % with respect to the total weight of the achiral component T.

3. Composition Exhibiting Optically Isotropic Liquid Crystal Phase

The liquid crystal composition of the invention includes an aspect of a composition (hereinafter sometimes referred to as the optically isotropic liquid crystal composition) including the achiral component T and a chiral agent and exhibiting an optically isotropic liquid crystal phase.

3-1. Achiral Component T

The achiral component T included in the optically isotropic liquid crystal composition of the invention includes the compound (1), and also includes one or more of the compounds (2) to (7) if necessary. That is, the achiral component T preferably includes at least one compound selected from the compounds (2), (3), (5) and (7), and particularly preferably includes the compound (3) or (7), in addition to the compound (1). In addition, according to desired properties, the achiral component T may include the compound (4) or (6). The compounds (1) to (7) are liquid crystal compounds.

In order to exhibit large dielectric anisotropy, it is preferred to further add the compound (3) or (7). These compositions exhibit very large dielectric anisotropy, and thus are compositions extremely effective for reducing a voltage of an optical device.

3-2. Chiral Agent

The chiral agent contained in the optically isotropic liquid crystal composition of the invention is an optically active compound, and preferably includes a compound selected from compounds having no radically polymerizable group.

The chiral agent used in the liquid crystal composition of the invention is preferably a compound having large helical twisting power (HTP). A necessary amount of the compound having large HTP for obtaining a desired pitch can be small; therefore, an increase in a driving voltage is suppressed, and such a compound is practically useful. Specifically, compounds (K1) to (K7) are preferred. Moreover, in the compounds (K4) to (K7), a binaphthyl group and an octahydronaphthyl group are optically active sites, and chirality of the chiral agent does not matter.

(K1)

(K2)

(K3)

(K4)

(K5)

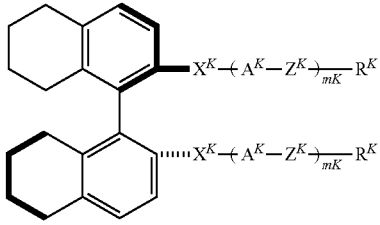
(K6)

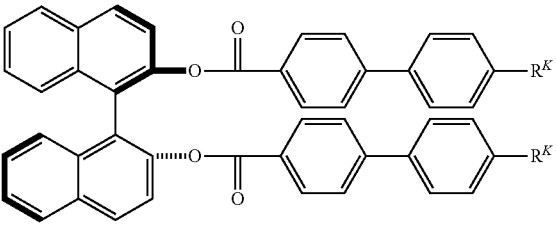
(K7)

In the formulae, each $R^K$ is independently alkyl having 3 to 10 carbons or alkoxy having 3 to 10 carbons, wherein at least one —$CH_2$—$CH_2$— in the alkyl or the alkoxy may be replaced with —CH=CH—.

In these compounds, as the chiral agent to be added to the liquid crystal composition, compounds (K4-1) to (K4-6), (K5-1) to (K5-3), (K6-1) to (K6-6), and (K7-1) to (K7-2) are preferred, and the compounds (K4-5), (K5-1) to (K5-3), (K6-5) to (K6-6), and (K7-1) to (K7-2) are more preferred.

(K4-1)

(K4-2)

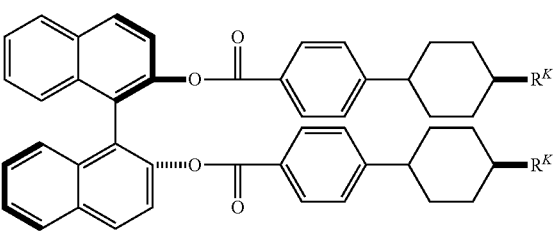
(K4-3)

-continued (K4-4)
(K4-5)
(K4-6)
(K5-1)
(K5-2)
(K5-3)

(K6-1)
(K6-2)
(K6-3)
(K6-4)
(K6-5)
(K6-6)
(K7-1)

(K7-2)

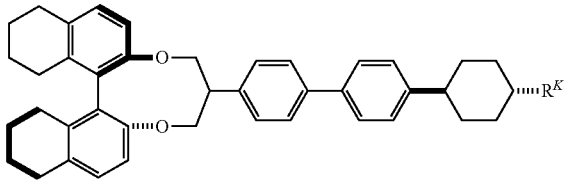

In the formulae, $R^K$ has the same meaning as in formulae (K1) to (K7).

As the chiral agent contained in the liquid crystal composition, one compound or a plurality of compounds may be used.

In order to facilitate exhibition of the optically isotropic liquid crystal phase, the chiral agent is preferably contained in an amount of 1 to 40 wt %, more preferably 3 to 25 wt % and particularly preferably 3 to 15 wt % with respect to a total weight of the liquid crystal composition of the invention.

3-3. Optically Isotropic Liquid Crystal Phase

In this specification, an expression "liquid crystal composition has optical isotropy" means that the liquid crystal composition shows the optical isotropy macroscopically because alignment of liquid-crystal molecules is isotropic, in which liquid-crystal order is present microscopically. "Pitch based on the liquid-crystal order that the liquid crystal composition microscopically has (hereinafter sometimes referred to simply as pitch)" is preferably 700 nm or less, more preferably 500 nm or less, and most preferably 350 nm or less.

In this specification, "a non-liquid-crystal isotropic phase" means a generally defined isotropic phase, i.e., a disordered phase, or even an isotropic phase in which a region with a non-zero local order parameter is caused by fluctuation. For example, the isotropic phase exhibited on a high-temperature side of the nematic phase corresponds to the non-liquid crystal isotropic phase in this specification. A similar definition applies to chiral liquid crystals in this specification.

In this specification, "an optically isotropic-liquid crystal phase" refers to a phase that exhibits an optically isotropic liquid crystal phase not caused by fluctuation. One example includes a phase that exhibits a platelet texture (blue phase in a narrow sense).

In this specification, a nematic phase refers to one in a narrow sense that excludes a chiral nematic phase, unless specifically indicated.

The optically isotropic liquid crystal composition of the invention has the optically isotropic liquid crystal phase. However, the typical platelet texture in the blue phase is sometimes not observed under observation by means of a polarizing microscope. Therefore, in this specification, the phase exhibiting the platelet texture is referred to as the blue phase, and the optically isotropic liquid crystal phase including the blue phase is referred to as the optically isotropic liquid crystal phase. That is, the blue phase is included in the optically isotropic liquid crystal phase.

In general, the blue phases are classified into three kinds, blue phase I, blue phase II and blue phase III, and all of these three kinds of blue phases are optically active, and isotropic.

In blue phase I or blue phase II, two or more kinds of diffracted light resulting from Bragg reflection from different lattice planes are observed. The blue phase is generally observed between the non-liquid crystal isotropic phase and the chiral nematic phase.

"State in which the optically isotropic liquid crystal phase shows no diffracted light having two or more colors" means that the platelet texture to be observed in blue phase I and blue phase II is not observed, and the phase exhibits substantially a single color in the entire plane. In the optically isotropic liquid crystal phase that shows no diffracted light having two or more colors, uniformity in color brightness in the plane is unnecessary.

The optically isotropic liquid crystal phase that shows no diffracted light having two or more colors has advantages that intensity of reflected light by Bragg reflection is suppressed, or reflection is shifted to a low wavelength side.

In addition, in a liquid crystal medium that reflects visible light, color may become a problem when the liquid crystal medium is utilized as a display device. However, in the liquid crystals that show no diffracted light having two or more colors, a reflection wavelength is shifted to the low wavelength side. Therefore, reflection of visible light can be caused to disappear by a pitch longer than that in the blue phase in the narrow sense (phase that exhibits the platelet texture).

In the liquid crystal composition of the invention that includes the achiral component T and the chiral agent, the chiral agent is preferably added in a concentration so that the pitch becomes 700 nm or less. Moreover, the composition exhibiting the nematic phase includes the compound (1), and if necessary, any other component.

In addition, the optically isotropic liquid crystal composition of the invention can also be obtained by adding the chiral agent to a composition having the chiral nematic phase but no optically isotropic liquid crystal phase. The composition having the chiral nematic phase but no optically isotropic liquid crystal phase includes the compound (1), the optically active compound, and if necessary, any other component. On this occasion, the chiral agent is preferably added in a concentration so that the pitch becomes 700 nm or more in order to not exhibit the optically isotropic liquid crystal phase. Here, the chiral agent to be added may be the aforementioned compounds (K1) to (K7) that have large HTP, and more preferably the compounds (K4-1) to (K4-6), (K5-1) to (K5-3), (K6-1) to (K6-6), or (K7-1) to (K7-2).

A temperature range in which the liquid crystal composition exhibits the optically isotropic liquid crystal phase according to a preferred aspect of the invention can be extended by adding the chiral agent to the liquid crystal composition having a wide temperature range in which the nematic phase or the chiral nematic phase coexists with the isotropic phase, and exhibiting the optically isotropic liquid crystal phase. For example, the composition exhibiting the optically isotropic liquid crystal phase in a wide temperature range can be prepared as follows. A liquid crystal compound having a high clearing point is mixed with a liquid crystal compound having a low clearing point to prepare a liquid crystal composition having a wide temperature range in which the nematic phase and the isotropic phase coexist, and the chiral agent is added thereto.

As the liquid crystal composition having the wide temperature range in which the nematic phase or the chiral nematic phase coexists with the isotropic phase, a liquid crystal composition having a difference of 3 to 150° C. between an upper-limit temperature and a lower-limit temperature of coexistence of the chiral nematic phase and the non-liquid crystal isotropic phase is preferred, and a liquid crystal composition having a difference of 5 to 150° C. is more preferred. In addition, a liquid crystal composition having a difference of 3 to 150° C. between an upper-limit temperature and a lower-limit temperature of coexistence of the nematic phase and the non-liquid crystal isotropic phase is preferred.

If an electric field is applied to the liquid crystal medium of the invention in the optically isotropic liquid crystal phase, electric birefringence occurs but the Kerr effect does not necessarily occur.

The electric birefringence in the optically isotropic liquid crystal phase becomes larger as the pitch becomes longer. Therefore, the electric birefringence can be increased by setting a long pitch by adjusting the type and content of the chiral agent, as long as requirements of other optical characteristics (transmittance, diffraction wavelength or the like) are satisfied.

3-4. Other Components

The liquid crystal composition of the invention may further include the following components within a range not significantly affecting characteristics of the composition: a solvent, a monomer, a polymer material, a polymerization initiator, an antioxidant, an ultraviolet absorber, a curing agent, a stabilizer, a dichroic dye, a photochromic compound and so forth.

In addition, examples of the dichroic dye used for the liquid crystal composition of the invention include merocyanine dyes, styryl dyes, azo dyes, azomethine dyes, azoxy dyes, quinophthalone dyes, anthraquinone dyes, tetrazine dyes and so forth.

4. Optically Isotropic Polymer/Liquid-Crystal Composite Material 4-1. Polymer/Liquid-Crystal Composite Material The polymer/liquid-crystal composite material of the invention is a composite material including a liquid crystal composition and a polymer and shows optical isotropy, and can be used for the optical device driven in the optically isotropic liquid crystal phase. The liquid crystal composition included in the polymer/liquid-crystal composite material of the invention is the liquid crystal composition of the invention.

In this specification, "polymer/liquid-crystal composite material" is not particularly limited as long as the composite material includes both the liquid crystal composition and a polymeric compound, but may be in a state in which the polymer is phase-separated from the liquid crystal composition in a state in which the polymer is partially or entirely not dissolved in the liquid crystal composition or a solvent or the like.

An optically isotropic polymer/liquid-crystal composite material according to a preferred aspect of the invention can exhibit the optically isotropic liquid crystal phase in a wide temperature range. In addition, the polymer/liquid-crystal composite material according to a preferred aspect of the invention has an extremely fast response rate. In addition, based on these effects, the polymer/liquid-crystal composite material according to a preferred aspect of the invention can be suitably used for an optical device such as a display device and so forth.

4-2. Polymeric Compound

The composite material of the invention can be produced by mixing the optically isotropic liquid crystal composition with a pre-polymerized polymer, but is preferably produced by mixing a low molecular weight monomer, macromonomer, oligomer or the like (hereinafter collectively referred to as "monomer or the like") as a material of the polymer with the liquid crystal composition, and then performing a polymerization reaction in the mixture. In this specification, the mixture including the monomer or the like and the liquid crystal composition is referred to as "polymerizable monomer/liquid-crystal mixture." The "polymerizable monomer/liquid-crystal mixture" may also include, if necessary, a polymerization initiator, a curing agent, a catalyst, a stabilizer, a dichroic dye or a photochromic compound as described later in a range not impairing the effects of the invention. For example, the polymerizable monomer/liquid-crystal mixture of the invention may also contain, if necessary, 0.1 to 20 weight parts of the polymerization initiator with respect to 100 weight parts of the polymerizable monomer. The "polymerizable monomer/liquid-crystal mixture" has to be a liquid crystal medium when polymerized in the blue phase, but is not necessarily a liquid crystal medium when polymerized in the isotropic phase.

A polymerization temperature is preferably a temperature at which the polymer/liquid-crystal composite material shows high transparency and isotropy. The polymerization temperature is more preferably a temperature at which the mixture of the monomer and the liquid-crystal material exhibits the isotropic phase or the blue phase, and polymerization is terminated in the isotropic phase or the optically isotropic liquid crystal phase. That is, the polymerization temperature is preferably a temperature at which, after polymerization, the polymer/liquid-crystal composite material does not substantially scatter light on a side of a wavelength longer than a wavelength of visible light, and exhibits an optically isotropic state.

For example, a low molecular weight monomer, macromonomer or oligomer can be used as a raw material of the polymer constituting the composite material of the invention. In this specification, a raw material monomer of the polymer covers low molecular weight monomers, macromonomers, oligomers or the like. In addition, the resultant polymer preferably has a three-dimensional crosslinking structure, and therefore, a polyfunctional monomer having two or more polymerizable functional groups is preferably used as the raw material monomer of the polymer. The polymerizable functional group is not particularly limited, and examples thereof include an acrylic group, a methacrylic group, a glycidyl group, an epoxy group, an oxetanyl group, a vinyl group and so forth. From a viewpoint of polymerization rate, an acrylic group and a methacrylic group are preferred. Among the raw material monomers of the polymer, it is preferred that a monomer having two or more polymerizable functional groups is contained in an amount of 10 wt % or more in the monomer since high transparency and isotropy are easily exhibited in the composite material of the invention.

In addition, in order to obtain a suitable composite material, the polymer preferably has a mesogen moiety, and a raw material monomer having the mesogen moiety can be partially or wholly used as the raw material monomer of the polymer.

4-2-1. Monofunctional, Bifunctional and Trifunctional Monomer Having Mesogen Moiety A mono- or bifunctional monomer having a mesogen moiety is not particularly limited structurally, and examples thereof include a compound represented by the following formula (M1) or formula (M2).

$$R^{MA}-Y^M-(A^M-Z^M)_{m1}-A^M-Y^M-R^{MB} \quad (M1)$$

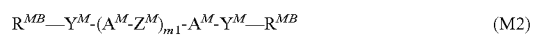

$$R^{MB}-Y^M-(A^M-Z^M)_{m1}-A^M-Y^M-R^{MB} \quad (M2)$$

In the compound (M1), $R^{MA}$ is hydrogen, halogen, —C≡N, —N=C=O, —N=C=S, or alkyl having 1 to 20 carbons, wherein at least one —CH$_2$— in the alkyl may be replaced with —O—, —S—, —CO—, —COO—, or —OCO—, and at least one —CH₂—CH₂— in the alkyl may be replaced with —CH=CH—, —CF=CF—, or —C≡C—, wherein in the alkyl having at least one —CH₂— replaced with —O—, —S—, —COO— or —OCO—, or in the alkyl having at least one —CH₂—CH₂— replaced with —CH=CH— or —C≡C—, at least one hydrogen may be replaced with halogen or —C—N. Each $R^{MB}$ is independently a polymerizable group represented by formulae (M3-1) to (M3-7).

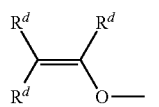
(M3-1)

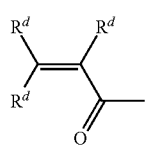
(M3-2)

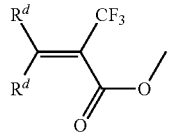
(M3-3)

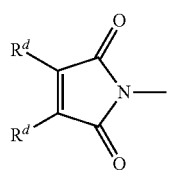
(M3-4)

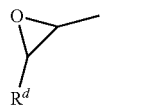
(M3-5)

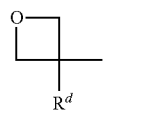
(M3-6)

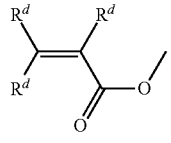
(M3-7)

$R^{MA}$ is preferably hydrogen, halogen, —C≡N, —CF₃, —CF₂H, —CFH₂, —OCF₃, —OCF₂H, alkyl having 1 to 20 carbons, alkoxy having 1 to 19 carbons, alkenyl having 2 to 21 carbons, or alkynyl having 2 to 21 carbons. $R^{MA}$ is particularly preferably —C≡N, alkyl having 1 to 20 carbons, or alkoxy having 1 to 19 carbons.

In the compounds (M1) and (M2), each $R^{MB}$ is independently a polymerizable group represented by formulae (M3-1) to (M3-7).

Here, in the formulae (M3-1) to (M3-7), each $R^d$ is independently hydrogen, halogen, or alkyl having 1 to 5 carbons, wherein at least one hydrogen in the alkyl may be replaced with halogen. $R^d$ is preferably hydrogen, halogen or methyl. $R^d$ is particularly preferably hydrogen, fluorine and methyl.

In addition, the compounds (M3-2) to (M3-4) and (M3-7) are suitably polymerized by radical polymerization. The compounds (M3-1), (M3-5) and (M3-6) are suitably polymerized by cationic polymerization. All of the above polymerizations are initiated when a small amount of radicals or cationic active species are generated in a reaction system. To accelerate generation of the active species, a polymerization initiator can be used. The active species can be generated with, e.g., light or heat.

In the compounds (M1) and (M2), each $A^M$ is independently an aromatic or non-aromatic five-membered ring or six-membered ring, or a fused ring having 9 or more carbons, wherein —CH₂— in the ring may be replaced with —O—, —S—, —NH— or —NCH₃—, —CH= in the ring may be replaced with —N=, and a hydrogen atom on the ring may be replaced with halogen, and alkyl or alkyl halide each having 1 to 5 carbons. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octane-1,4-diyl, wherein at least one —CH₂— in the rings may be replaced with —O—, at least one —CH= may be replaced with —N=, and at least one hydrogen in the rings may be replaced with halogen, alkyl having 1 to 5 carbons or alkyl halide having 1 to 5 carbons.

In consideration of stability of the compound, —CH₂—O—CH₂—O— in which oxygen and oxygen are not adjacent is preferred to —CH₂—O—O—CH₂— in which oxygen and oxygen are adjacent. The same rule also applies to the case of sulfur.

Among these, particularly preferred $A^M$ includes 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl and pyrimidine-2,5-diyl. Moreover, a configuration of the 1,4-cyclohexylene and 1,3-dioxane-2,5-diyl is preferably a trans configuration rather than a cis configuration.

2-fluoro-1,4-phenylene is structurally the same as 3-fluoro-1,4-phenylene, and thus examples are not shown for the latter. This also applies to a relationship between 2,5-difluoro-1,4-phenylene and 3,6-difluoro-1,4-phenylene, or the like.

Each $Y^M$ is independently a single bond, or alkylene having 1 to 20 carbons, wherein at least one —CH₂— in the alkylene may be replaced with —O— or —S—, and at least one —CH₂—CH₂— in the alkylene may be replaced with —CH=CH—, —C≡C—, —COO—, or —OCO—. $Y^M$ is preferably a single bond, —(CH₂)$_{m2}$—, —O(CH₂)$_{m2}$—, or —(CH₂)$_{m2}$O— (wherein m2 is an integer of 1 to 20). $Y^M$ is particularly preferably a single bond, —(CH₂)$_{m2}$—, —O(CH₂)$_{m2}$—, or —(CH₂)$_{m2}$O— (wherein m2 is an integer of 1 to 10). In consideration of stability of the compound, —$Y^M$—$R^{MA}$ and —$Y^M$—$R^{MB}$ preferably have no —O—O—, —O—S—, —S—O—, or —S—S— in the groups.

Each $Z^M$ is independently a single bond, —(CH₂)$_{m3}$—, —O(CH₂)$_{m3}$—, —(CH₂)$_{m3}$O—, —O(CH₂)$_{m3}$O—, —CH=CH—, —C≡C—, —COO—, —OCO—, —(CF₂)₂—, —(CH₂)₂—COO—, —OCO—(CH₂)₂—, —CH=CH—COO—, —OCO—CH=CH—, —C≡C—COO—, —OCO—C≡C—, —CH=CH—(CH₂)₂—, —(CH₂)₂—CH=CH—, —CF=CF—, —C≡C—

CH=CH—, —CH=CH—C≡C—, —OCF$_2$—(CH$_2$)$_2$—, —(CH$_2$)$_2$—CF$_2$O—, —OCF$_2$— or —CF$_2$O— (wherein m3 is an integer of 1 to 20).

$Z^M$ is preferably a single bond, —(CH$_2$)$_{m3}$—, —O(CH$_2$)$_{m3}$—, —(CH$_2$)$_{m3}$O—, —CH=CH—, —C≡C—, —COO—, —OCO—, —(CH$_2$)$_2$—COO—, —OCO—(CH$_2$)$_2$—, —CH=CH—COO—, —OCO—CH=CH—, —OCF$_2$—, or —CF$_2$O—.

m1 is an integer of 1 to 6. m1 is preferably an integer of 1 to 3. When m1 is 1, the compounds are bicyclic compounds having two rings such as two six-membered rings. When m1 is 2 or 3, the compounds are respectively tricyclic or tetracyclic compounds. For example, when m1 is 1, two of $A^M$ may be the same or different. For example, when m1 is 2, three of $A^M$ (or two of $Z^M$) may be the same or different. When m1 is 3 to 6, the same rules applies. The same rules also applies to $R^{MA}$, $R^{MB}$, $R^d$, $Z^M$, $A^M$, and $Y^M$.

Even if the compounds (M1) and (M2) include an isotope such as $^2$H (deuterium), $^{13}$C or the like in an amount more than the natural abundance, they still have the same characteristics and thus are favorably used.

More preferred examples of the compounds (M1) and (M2) include compounds (M1-1) to (M1-41) and (M2-1) to (M2-27). In these compounds, $R^{MA}$, $R^{MB}$, $R^d$, $Z^M$, $A^M$, $Y^M$ and p are defined as in the case of formulae (M1) and (M2) described above.

The following substructures in the compounds (M1-1) to (M1-41) and (M2-1) to (M2-27) are explained. The substructure (a1) represents 1,4-phenylene in which at least one hydrogen is replaced with fluorine. The substructure (a2) represents 1,4-phenylene in which at least one hydrogen may be replaced with fluorine. The substructure (a3) represents 1,4-phenylene in which at least one hydrogen may be replaced with either fluorine or methyl. The substructure (a4) represents fluorene in which the hydrogen at position 9 may be replaced with methyl.

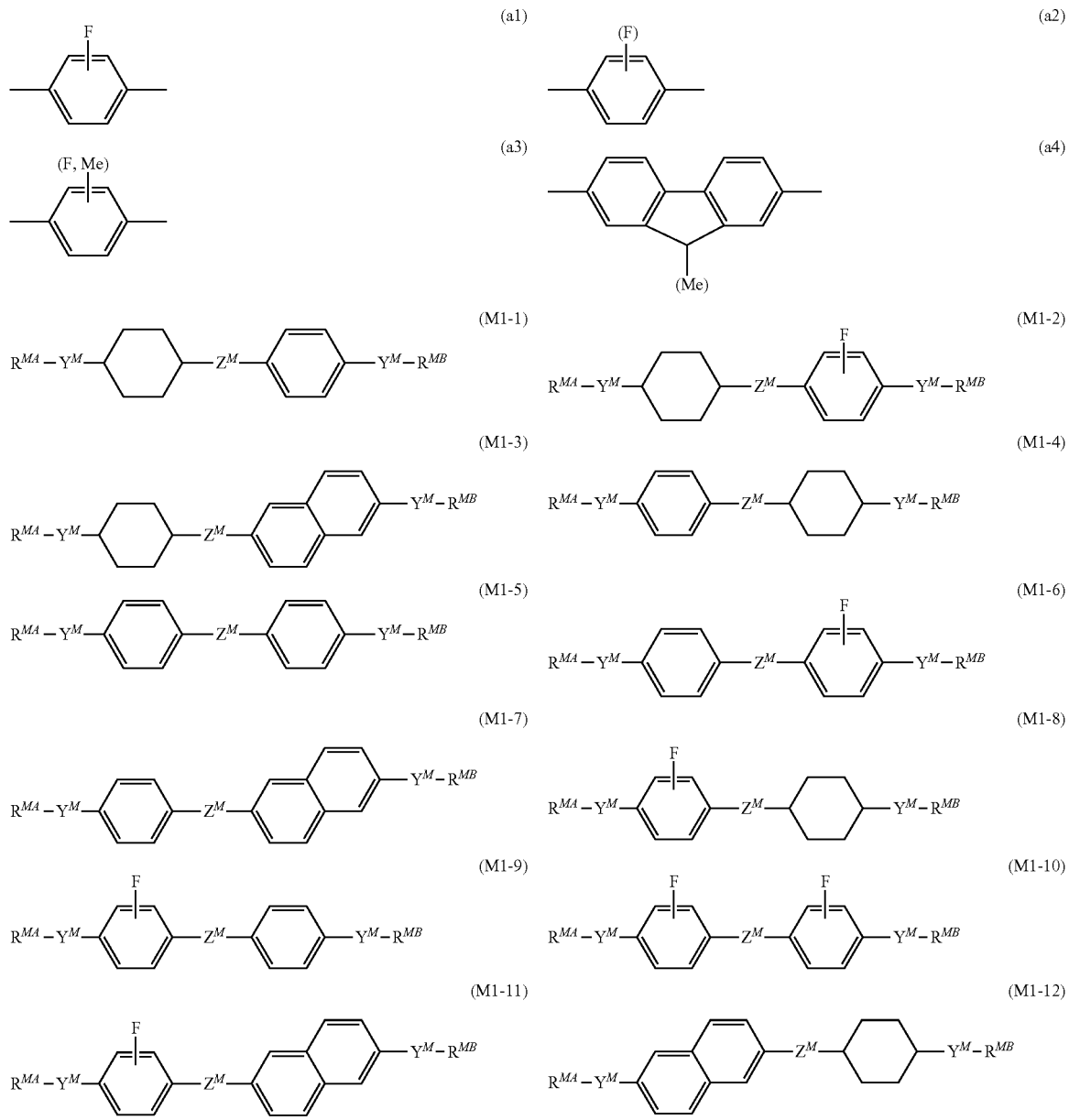

-continued
(M1-13)
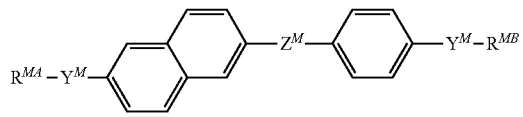
(M1-14)
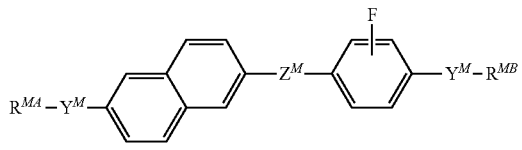
(M1-15)
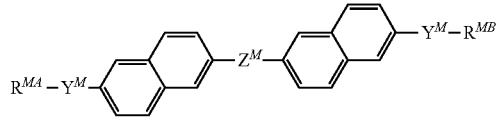
(M1-16)
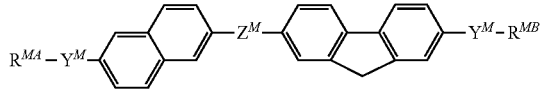
(M1-17)
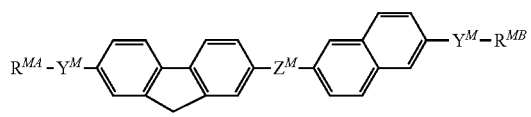
(M1-18)
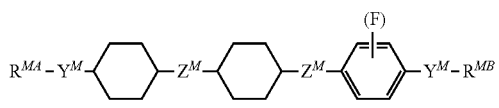
(M1-19)
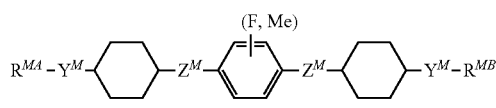
(M1-20)
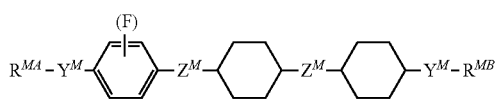
(M1-21)
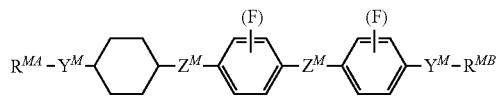
(M1-22)
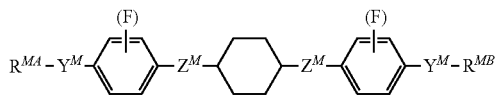
(M1-23)
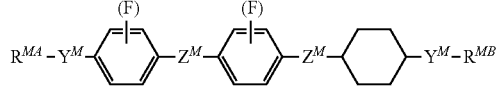
(M1-24)
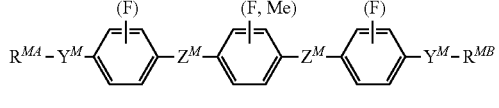
(M1-25)
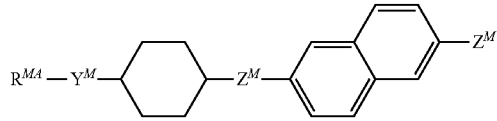
(M1-26)
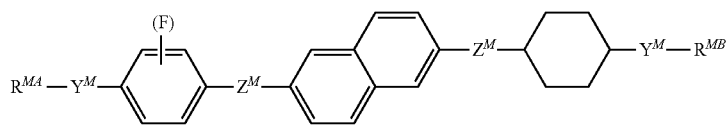
(M1-27)
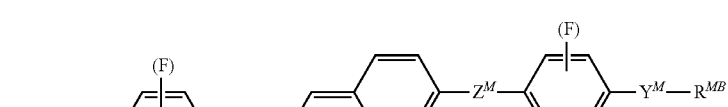
(M1-28)
(M1-29)
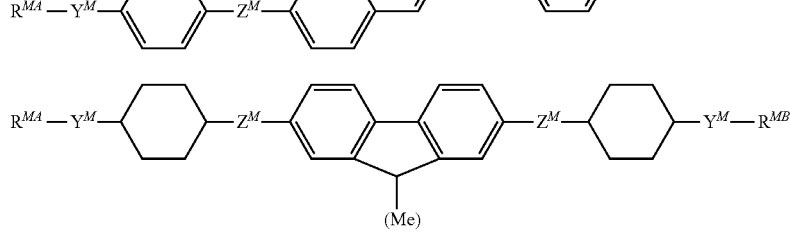

-continued
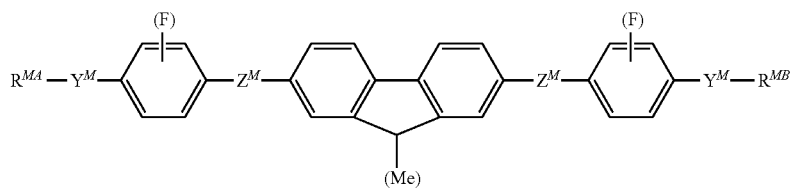 (M1-30)
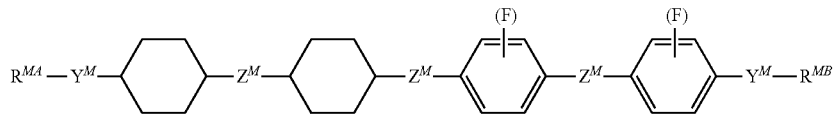 (M1-31)
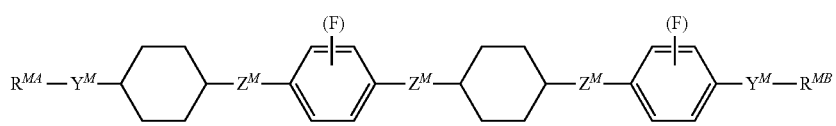 (M1-32)
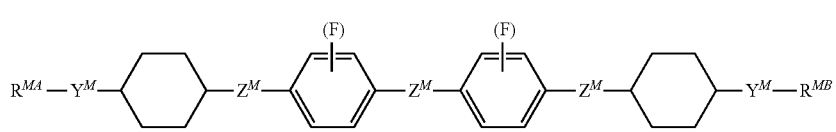 (M1-33)
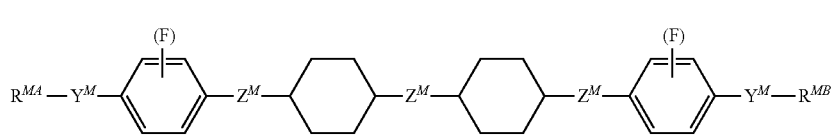 (M1-34)
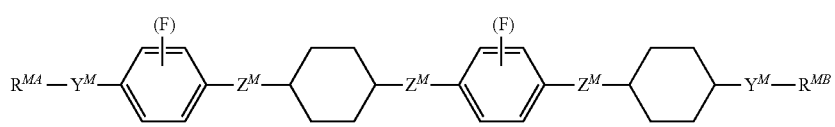 (M1-35)
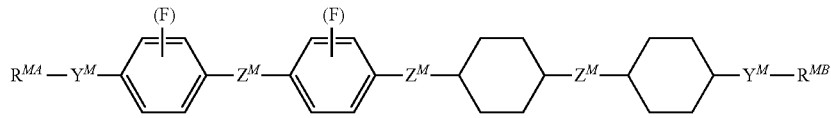 (M1-36)
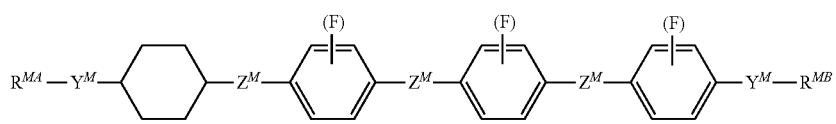 (M1-37)
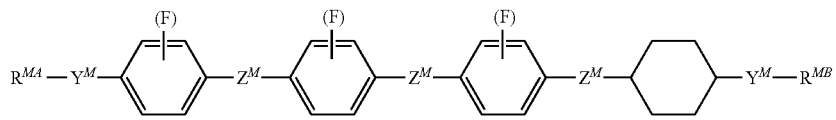 (M1-38)
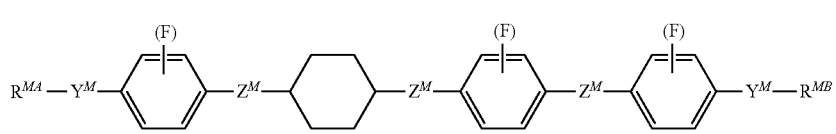 (M1-39)
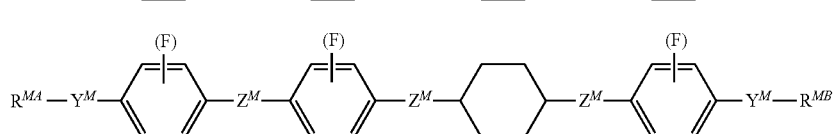 (M1-40)
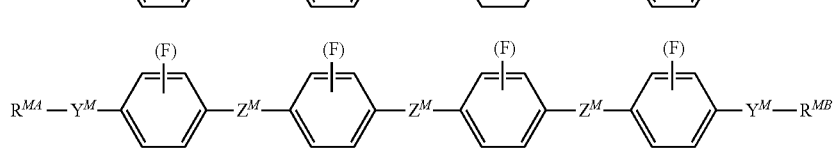 (M1-41)

-continued
(M2-1)
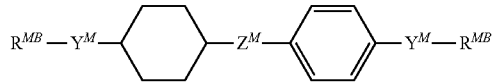
(M2-2)
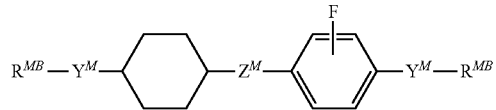
(M2-3)
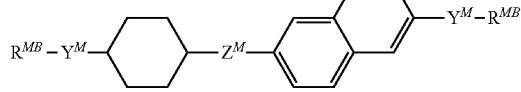
(M2-4)
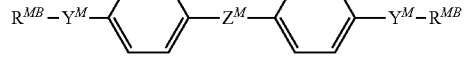
(M2-5)
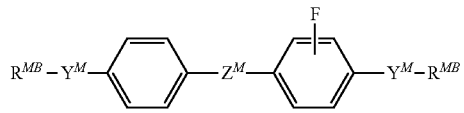
(M2-6)
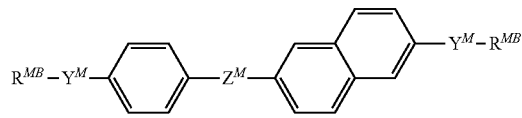
(M2-7)
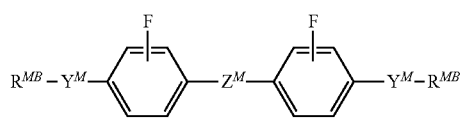
(M2-8)
(M2-9)
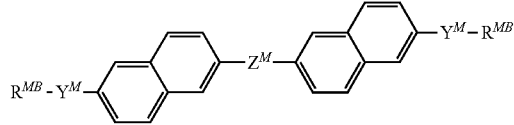
(M2-10)
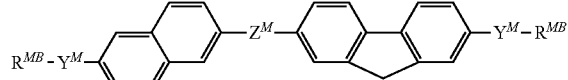
(M2-11)
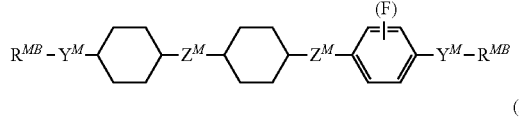
(M2-12)
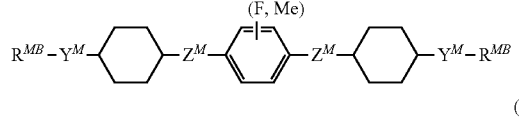
(M2-13)
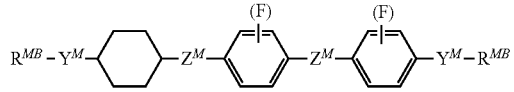
(M2-14)
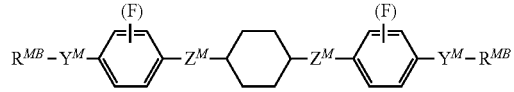
(M2-15)
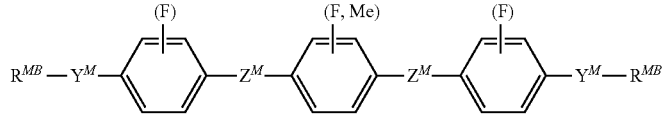
(M2-16)
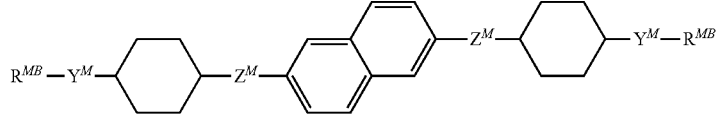
(M2-17)
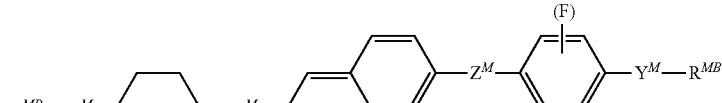
(M2-18)
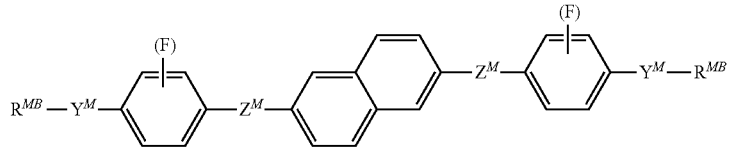

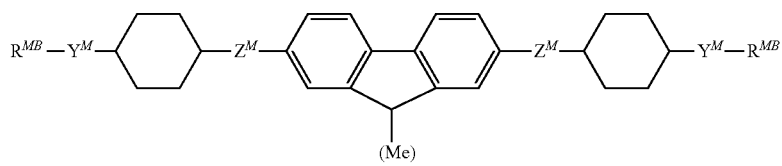

(M2-19)

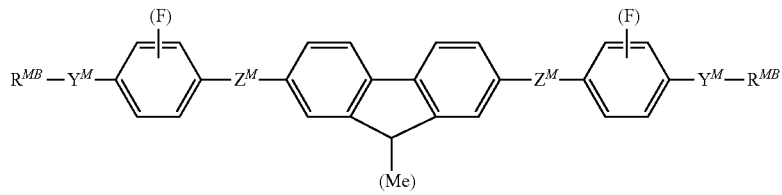

(M2-20)

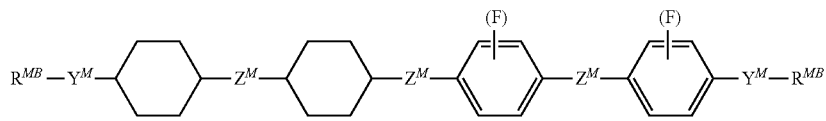

(M2-21)

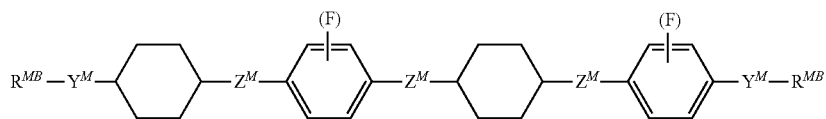

(M2-22)

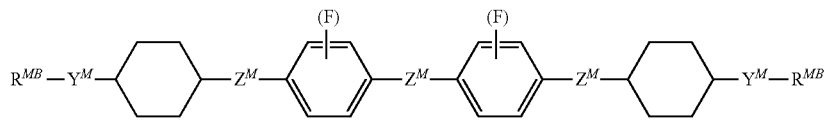

(M2-23)

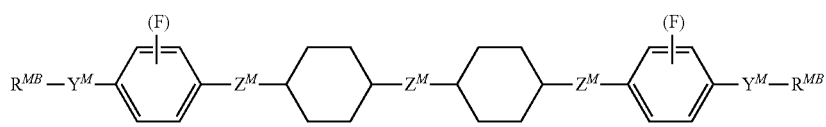

(M2-24)

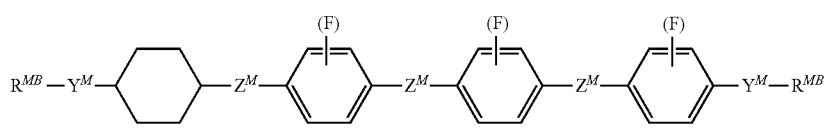

(M2-25)

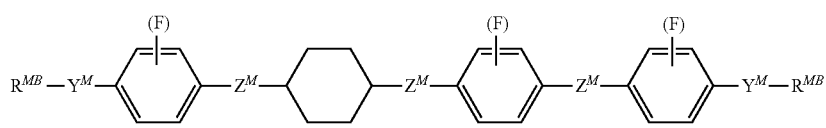

(M2-26)

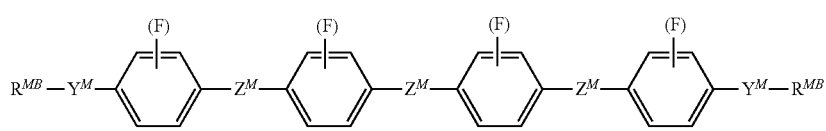

(M2-27)

A monomer having no aforementioned mesogen moiety, and a polymerizable compound having a mesogen moiety other than the monomers (M1) and (M2) can be used as a raw material monomer of the polymer if necessary.

In order to optimize the optical isotropy of the polymer/liquid-crystal composite material of the invention, a monomer having a mesogen moiety and three or more polymerizable functional groups can also be used. As the monomer having a mesogen moiety and three or more polymerizable functional groups, a well-known compound can be suitably used. For example, compounds (M4-1) to (M4-3), and more specifically, compounds described in Japanese Patent Publication Nos. 2000-327632, 2004-182949 and 2004-59772, can be used. In (M4-1) to (M4-3), $R^{MB}$, $Z^M$, $Y^M$ and (F) are defined as above.

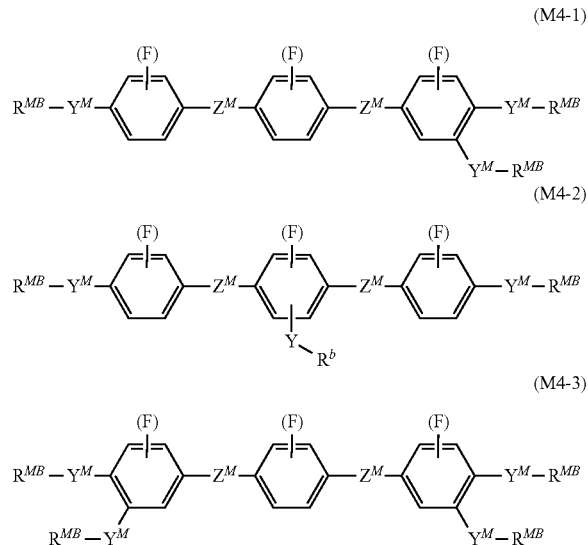

4-2-2. Monomer Having Polymerizable Functional Group and No Mesogen Moiety Examples of the monomer having a polymerizable group and no mesogen moiety include linear or branched acrylate having 1 to 30 carbons, linear or branched diacrylate having 1 to 30 carbons, and, as a monomer having three or more polymerizable groups, glycerol propoxylate (1PO/OH) triacrylate, pentaerythritol propoxylate triacrylate, pentaerythritol triacrylate, trimethylolpropane ethoxylate triacrylate, trimethylolpropane propoxylate triacrylate, trimethylolpropane triacrylate, di(trimethylolpropane)tetraacrylate, pentaerythritol tetraacrylate, di(pentaerythritol)pentaacrylate, di(pentaerythritol) hexaacrylate, trimethylolpropane triacrylate and so forth. However, the invention is not limited thereto.

4-2-3. Polymerization Initiator

The polymerization reaction for producing the polymer constituting the composite material of the invention is not particularly limited, and may be performed by, e.g., photo-radical polymerization, thermal radical polymerization, photo-cationic polymerization and so forth.

Examples of a photoradical polymerization initiator useful for photoradical polymerization include DAROCUR™ 1173 and 4265 (both are trade names, made by BASF Japan Ltd.) and IRGACURE™ 184, 369, 500, 651, 784, 819, 907, 1300, 1700, 1800, 1850 and 2959 (all are trade names, made by BASF Japan Ltd.).

Examples of a preferred thermal radical polymerization initiator useful for thermal radical polymerization include benzoyl peroxide, diisopropyl peroxydicarbonate, t-butyl peroxy-2-ethylhexanoate, t-butyl peroxypivalate, t-butyl peroxydiisobutyrate, lauroyl peroxide, dimethyl-2,2'-azobisisobutyrate (MAIB), di-t-butyl peroxide (DTBPO), azobisisobutyronitrile (AIBN) and azobiscyclohexanecarbonitrile (ACN).

Examples of a photo-cationic polymerization initiator useful for photo-cationic polymerization include diaryliodonium salt (hereinafter referred to as "DAS") and triarylsulfonium salt (hereinafter referred to as "TAS").

Examples of the DAS include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium-p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethanesulfonate, 4-methoxyphenylphenyliodonium trifluoroacetate, and 4-methoxyphenylphenyliodonium-p-toluenesulfonate.

Sensitivity of the DAS can be improved by addition of a photosensitizer such as thioxanthone, phenothiazine, chlorothioxanthone, xanthone, anthracene, diphenylanthracene, rubrene and so forth.

Examples of the TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium-p-toluenesulfonate, triphenylsulfonium tetra(pentafluorophenyl)borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethanesulfonate, 4-methoxyphenyldiphenylsulfonium trifluoroacetate, and 4-methoxyphenyldiphenylsulfonium-p-toluenesulfonate.

Specific examples of trade names of the photo-cationic polymerization initiator include Cyracure™ UVI-6990, UVI-6974 and UVI-6992 (all are trade names, made by UCC Corporation), ADEKA OPTOMER™ SP-150, SP-152, SP-170 and SP-172 (all are trade names, made by ADEKA Corporation), Rhodorsil Photoinitiator™2074 (trade name, made by Rhodia Japan Corporation), IRGACURE™ 250 (trade name, made by BASF Japan Ltd.) and UV-9380C (trade name, made by GE/Toshiba Silicone Co. Ltd.).

4-2-4. Curing Agents or the Like

In production of the polymer constituting the composite material of the invention, in addition to the monomer or the like and the polymerization initiator, other suitable components, e.g., a curing agent, a catalyst, a stabilizer and so forth, may also be added.

Generally, the curing agent can be a conventional well-known latent curing agent used as a curing agent for epoxy resin. Examples of the latent curing agent for epoxy resin include amine-based curing agents, novolac resin-based curing agents, imidazole-based curing agents, anhydride-based curing agents and so forth. Examples of the amine-based curing agents include: aliphatic polyamines, such as diethylenetriamine, triethylenetetramine, tetraethylenepentamine, m-xylenediamine, trimethylhexamethylenediamine, 2-methylpentamethylenediamine, diethylaminopropylamine and so forth; alicyclic polyamines, such as isophoronediamine, 1,3-bisaminomethylcyclohexane, bis(4-aminocyclohexyl)methane, norbornenediamine, 1,2-diaminocyclohexane, laromine and so forth; and aromatic polyamines, such as diaminodiphenylmethane, diaminodiphenylethane, metaphenylenediamine and so forth.

Examples of the novolac resin-based curing agents include phenol novolac resin and bisphenol novolac resin. Examples of the imidazole-based curing agents include 2-methylimidazole, 2-ethylhexylimidazole, 2-phenylimidazole, and 1-cyanoethyl-2-phenylimidazolium trimellitate.

Examples of the anhydride-based curing agents include tetrahydrophthalic anhydride, hexahydrophthalic anhydride, methyltetrahydrophthalic anhydride, methylhexahydrophthalic anhydride, methylcyclohexene tetracarboxylic dianhydride, phthalic anhydride, trimellitic anhydride, pyromellitic anhydride, and benzophenonetetracarboxylic dianhydride.

In addition, a curing accelerator for accelerating a curing reaction between a polymerizable compound having a glycidyl group, an epoxy group and an oxetanyl group and the curing agent may be further used. Examples of the curing accelerator include: tertiary amines, such as benzyldimethyl amine, tris(dimethylaminomethyl)phenol, dimethylcyclohexylamine and so forth; imidazoles, such as 1-cyanoethyl-2-ethyl-4-methylimidazole,2-ethyl-4-methylimidazole and so forth; organophosphorus compounds, such as triphenylphosphine and so forth; quaternary phosphonium salts, such as tetraphenylphosphonium bromide and so forth; diazabicycloalkenes, such as 1,8-diazabicyclo[5.4.0]undecene-7 and an organic acid salt thereof and so forth; quaternary ammonium salts, such as tetraethylammonium bromide, tetrabutylammonium bromide and so forth; and boron compounds, such as boron trifluoride, triphenyl borate and so forth. These curing accelerators can be used alone or in a mixture of two or more.

In addition, in order to prevent unwanted polymerization during storage, for example, a stabilizer is preferably added. As the stabilizer, all the compounds known by persons skilled in the art can be used. Representative examples of the stabilizer include 4-ethoxyphenol, hydroquinone, butylated hydroxytoluene (BHT) and so forth.

4-3. Composition of Polymer/Liquid-Crystal Composite Material

The content of the liquid crystal composition in the polymer/liquid-crystal composite material of the invention is preferably as high as possible, as long as the composite material can exhibit the optically isotropic liquid crystal phase. A reason is that the electric birefringence value of the composite material of the invention increases as the content of the liquid crystal composition is higher.

In the polymer/liquid-crystal composite material of the invention, the content of the liquid crystal composition is preferably 60 to 99 wt %, more preferably 60 to 98 wt %, and particularly preferably 80 to 97 wt %, with respect to the composite material. In addition, the content of the polymer is preferably 1 to 40 wt %, more preferably 2 to 40 wt %, and particularly preferably 3 to 20 wt %, with respect to the composite material.

5. Optical Device

The optical device of the invention is an optical device including the liquid crystal composition or the polymer/liquid-crystal composite material (hereinafter, the liquid crystal composition and the polymer/liquid-crystal composite material according to the invention are sometimes referred to generically as the liquid crystal medium) and driven in the optically isotropic liquid crystal phase.

The liquid crystal medium is optically isotropic when no electric field is applied; when an electric field is applied, the liquid crystal medium shows optical anisotropy so that optical modulation can be achieved by the electric field.

Examples of structures of the liquid-crystal display device include, as shown in FIG. 1, a structure in which an electrode 1 extending from a left side and an electrode 2 extending from a right side are alternately arranged in electrodes of a comb-shaped electrode substrate. When there is a potential difference between the electrode 1 and the electrode 2, a state can be provided in which electric fields of two directions, namely, an upward direction and a downward direction in the drawing, exist on the comb-shaped electrode substrate as shown in FIG. 1, if attention is paid to one electrode.

The liquid crystal composition of the invention can be used for the optical device. The liquid crystal composition of the invention shows a low driving voltage and a short response time. Therefore, the optical device according to a preferred aspect of the invention can be driven at a low voltage and can make a response at high speed.

EXAMPLES

In the following, the invention is described in further detail according to examples.

However, the invention is not limited by these examples. Moreover, unless otherwise noted, "%" means "wt %."

In addition, a resultant compound was identified on the basis of a nuclear magnetic resonance spectrum obtained by means of $^1$H-NMR analysis, a gas chromatogram obtained by means of gas chromatography (GC) analysis and so forth. The analysis methods were as follows.

1) Analysis Methods 1-1) $^1$H-NMR Analysis

As a measuring apparatus, DRX-500 (trade name, made by Bruker BioSpin K.K.) was used. In the measurement, a sample prepared in the examples and so forth was dissolved in a deuterated solvent such as $CDCl_3$ or the like in which the sample was soluble, and was measured under conditions of room temperature, 500 MHz and 24 times of accumulation. In the explanation of the resultant nuclear magnetic resonance spectrum, "s" denotes singlet, "d" denotes doublet, "t" denotes triplet, "q" denotes quartet and "m" denotes multiplet. Tetramethylsilane (TMS) was used as a reference material for a zero point of a chemical shift (δ value).

1-2) GC Analysis

As a measuring apparatus, GC-14B Gas Chromatograph made by Shimadzu Corporation was used. As a column, a capillary column CBP1-M25-025 (length: 25 m, inner diameter: 0.22 mm, film thickness: 0.25 μm; dimethylpolysiloxane as a stationary liquid phase; nonpolar) made by Shimadzu Corporation was used. Helium was used as a carrier gas, and a flow rate was adjusted to 1 ml/min. A temperature in a sample vaporizing chamber was set to 300° C., and a temperature of a detector (FID) part was set to 300° C.

A sample was dissolved in toluene to prepare a 1 wt % solution, and 1 μl of the resultant solution was injected into the sample vaporizing chamber.

As a recorder, C-R6A Chromatopac made by Shimadzu Corporation or an equivalent thereof was used. The resultant gas chromatogram shows a peak retention time and a peak area value corresponding to component compounds.

As a diluent solvent for the sample, chloroform or hexane, for example, may also be used. In addition, as the column, capillary column DB-1 (length: 30 m, inner diameter: 0.32 mm, film thickness: 0.25 μm) made by Agilent Technologies Inc., HP-1 (length: 30 m, inner diameter: 0.32 mm, film thickness: 0.25 μm) made by Agilent Technologies Inc., Rtx-1 (length: 30 m, inner diameter: 0.32 mm, film thickness: 0.25 μm) made by Restek Corporation, BP-1 (length: 30 in, inner diameter: 0.32 mm, film thickness: 0.25 μm) made by SGE International Pty. Ltd. and so forth may be used.

A peak area ratio in the gas chromatogram corresponds to a ratio of the component compounds. In general, weight percentage of each component compound in the analyzed sample is not completely the same as an area percentage of each peak in the analyzed sample. However, when the aforementioned column is used in the invention, since a correction coefficient is substantially 1, the weight percentage of each component compound in the analyzed sample substantially corresponds to the area percentage of each peak in the analyzed sample. This is because there is no significant difference among the correction coefficients of the liquid crystal compounds as components. In order to more accurately obtain a composition ratio of the liquid crystal compounds in the liquid crystal composition by the gas chromatogram, an internal standard method by the gas chromatogram is used. Each liquid crystal compound component (test component) and a liquid crystal compound as a reference (reference material) weighed accurately in a fixed amount are simultaneously measured by means of gas chromatography, and relative intensity of the area ratio between an obtained peak of the test component and an obtained peak of the reference material is calculated in advance. When correction is performed using the relative intensity of the peak area of each component to the reference material, the composition ratio of the liquid crystal compounds in the liquid crystal composition can be more accurately obtained from the GC analysis.

1-3) Sample for measuring physical property values of liquid crystal compounds or the like A sample for measuring physical property values of a liquid crystal compound is used in two types of cases: a case where the compound per se is used as the sample, and a case where the compound is mixed with a mother liquid crystal to be used as the sample.

In the latter case where the sample prepared by mixing the compound with a mother liquid crystal is used, measurement is carried out by the following method. First, a sample is prepared by mixing 15 wt % of the resultant liquid crystal compound with 85 wt % of the mother liquid crystal. Then, from measured values of the resultant sample, an extrapolated value is calculated in accordance with an extrapolation method based on the following equation. The extrapolated value is used as a physical property value of the compound.

<Extrapolated value>=(100×<measured value of sample>−<wt % of mother liquid crystal>×<measured value of mother liquid crystal>)/<wt % of liquid crystal compound>

In a case where a smectic phase or crystals precipitated at 25° C. while the ratio of the liquid crystal compound to the mother liquid crystal is at the above ratio (15 wt %:85 wt %), the ratio of the liquid crystal compound to the mother liquid crystal was changed to 10 wt %:90 wt %, 5 wt %:95 wt %, and 1 wt %:99 wt % in order. The characteristic values of the sample were measured for a composition in which a smectic phase or crystals do not precipitate at 25° C., and extrapolated values were obtained with the above equation and used as characteristic values of the liquid crystal compound.

There are various kinds of mother liquid crystals that can be used for the measurement. For example, a composition (wt %) of a mother liquid crystal A is as follows.

(Mother Liquid Crystal A)

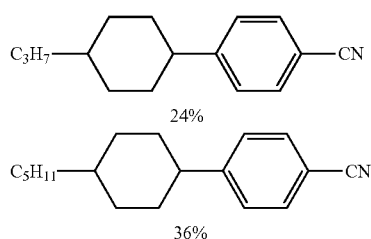

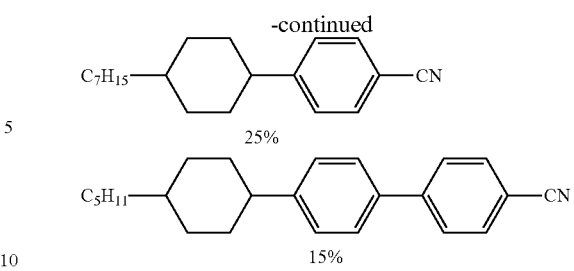

1-4) Method for measuring physical property values of liquid crystal compound or the like The measurement of the physical property values of the liquid crystal compound was performed by a method described later. Most of the measurement methods are described in EIAJ-ED-2521A of the Standard of Electronic Industries Association of Japan, or modified thereon. In addition, no TFT was attached to a TN device used for measurement.

Among measured values, when the liquid crystal compound per se was used as the sample, values obtained were described as experimental data. When a mixture of the liquid crystal compound and the mother liquid crystals was used as the sample, values obtained by the extrapolation method were described as experimental data.

1-4-1) Phase structure and phase transition temperature (° C.)

The measurement was carried out by the following method (1) and method (2).

(1) A compound was placed on a hot plate (FP52 Hot Stage made by Mettler Toledo International Inc.) of a melting point apparatus equipped with a polarizing microscope, and a phase state and a change thereof were observed with the polarizing microscope while the compound was heated at a rate of 3° C./min, and a kind of the liquid crystal phase was specified.

(2) A sample was heated and then cooled at a rate of 3° C./min or 5° C./min using a scanning calorimeter, DSC-7 System or Diamond DSC System, made by PerkinElmer, Inc. A starting point (onset) of an endothennic peak or an exothermnnic peak caused by a phase change of the sample was obtained by extrapolation, and a phase transition temperature was determined. In the following, crystal is expressed as C; when distinction is made between the crystals, the crystals are expressed as $C_1$ or $C_2$. In addition, the smectic phase is expressed as Sm, the nematic phase as N, and the chiral nematic phase as N*. A liquid (isotropic) is expressed as I. In the smectic phase, when distinction is made between smectic B phase and smectic A phase, the phases are expressed as SmB or SmA, respectively. BP represents the blue phase or the optically isotropic liquid crystal phase. A biphase coexistence is sometimes expressed as (N*+I) or (N*+BP). Specifically, (N*+I) represents a phase in which a non-liquid crystal isotropic phase and a chiral nematic phase coexist, and (N*+BP) represents a phase in which a BP phase or an optically isotropic liquid crystal phase and a chiral nematic phase coexist. Un represents a non-optically isotropic unidentified phase. For the notation of the phase transition temperature, e.g., "C 50.0 N 100.01" means that the phase transition temperature (CN) from the crystal to the nematic phase is 50.0° C., and the phase transition temperature (NI) from the nematic phase to the liquid is 100.0° C. The same applies to other notations.

1-4-2) Upper-limit temperature ($T_{NI}$; ° C.) of nematic phase

A sample (a mixture of the liquid crystal compound and the mother liquid crystal) was placed on a hot plate (FP52 Hot Stage made by Mettler Toledo International Inc.) of a melting point apparatus equipped with a polarizing microscope, and the sample was observed with the polarizing microscope while heated at a rate of 1° C./min. A temperature at which a portion of the sample changed from the nematic phase to an isotropic liquid was described as an upper-limit temperature of the nematic phase. In the following, the upper-limit temperature of the nematic phase is sometimes abbreviated simply as "upper-limit temperature."

1-4-3) Low-Temperature Compatibility

Samples were prepared by mixing the mother liquid crystal with the liquid crystal compound so that the content of the liquid crystal compound was 20 wt %, 15 wt %, 10 wt %, 5 wt %, 3 wt %, and 1 wt %, respectively, and then placed into glass bottles. The glass bottles were kept in a freezer at −10° C. or −20° C. for a fixed period, and whether or not a crystal or a smectic phase is precipitated was observed.

1-4-4) Viscosity (bulk viscosity; η; measured at 20° C.; mPa·s)

The mixture of the liquid crystal compound and the mother liquid crystal was measured using an E-type viscometer.

1-4-5) Refractive Index Anisotropy (Δn) The measurement was carried out at 25° C. using light having a wavelength of 589 nm by means of an Abbe refractometer having a polarizing plate mounted on an ocular lens. After a surface of a main prism was rubbed in a direction, the sample (the mixture of the liquid crystal compound and the mother liquid crystal) was dripped onto the main prism. A refractive index ($n_\parallel$) was measured when a polarization direction was parallel to the rubbing direction. A refractive index ($n_\parallel$) was measured when the polarization direction was perpendicular to the rubbing direction. A value of the refractive index anisotropy (Δn) was calculated according to an equation $\Delta n = n_\parallel - \perp$.

1-4-6) Dielectric Anisotropy (Δ∈; Measured at 25° C.)

The sample (the mixture of the liquid crystal compound and the mother liquid crystal) was put into a liquid-crystal cell having an interval (gap) of approximately 9 μm between two glass substrates and a twist angle of 80 degrees. A voltage of 20 V was applied to the liquid-crystal cell, and permittivity ($\in_\parallel$) in a major axis direction of a liquid-crystal molecule was measured. A voltage of 0.5 V was applied, and permittivity ($e_\perp$) in a minor axis direction of the liquid-crystal molecule was measured. A value of the dielectric anisotropy was calculated according to an equation $\Delta\in = \in_\parallel - \in_\perp$.

1-4-7) Pitch (P; Measured at 25° C.; Nm)

A pitch length was measured through selective reflection (Handbook of Liquid Crystal, p. 196, 2000, Maruzen). For a selective reflection wavelength), a relationship <n>p/λ=1 exists. Here, <n> represents an average refractive index, and is calculated according to the equation: $<n> = \{(n_\parallel^2 + n_\perp^2)/2\}^{1/2}$. The selective reflection wavelength was measured by a microspectrophotometer (trade name: MSV-350, made by Japan Electronics Co., Ltd.). The pitch was obtained by dividing the resultant reflection wavelength by the average refractive index. In a region of low concentration of the optically active compound, a pitch of a cholesteric liquid crystal having a reflection wavelength in a region of wavelength longer than that of visible light is proportional to a reciprocal of the concentration of the optically active compound. Therefore, several points were measured for the pitch length of the liquid crystal having a selective reflection wavelength in the visible light region, and the pitch was obtained by a linear extrapolation method. The "optically active compound" is equivalent to the chiral agent in the invention.

1-5) Method for Measuring Physical Property Values of Liquid Crystal Composition or the Like The measurement of characteristic values of the liquid crystal composition can be performed by the following method. Most of the measurement methods are described in EIAJ-ED-2521A of the Standard of Electronic Industries Association of Japan, or modified thereon. No TFT was attached to a TN device used for measurement.

1-5-1) Upper-limit temperature (NI; ° C.) of nematic phase

The sample was placed on the hot plate of the melting point apparatus equipped with the polarizing microscope and was heated at a rate of 1° C./min. The temperature at which a portion of the sample changed from the nematic phase to the isotropic liquid was measured. The upper-limit temperature of the nematic phase is sometimes abbreviated simply as "upper-limit temperature."

1-5-2) Lower-limit temperature ($T_C$; ° C.) of nematic phase A sample having the nematic phase was kept in a freezer at 0° C., −10° C., −20° C., −30° C., and −40° C. for 10 days, followed by observation of the liquid crystal phase. For example, in a case where the sample remained in the nematic phase at −20° C. and changed to a crystal (or the smectic phase) at −30° C., the $T_C$ is described as ≤20° C. The lower-limit temperature of the nematic phase is sometimes abbreviated as "lower-limit temperature."

1-5-3) Transition Temperature of Optically Isotropic Liquid Crystal Phase

The sample was placed on the hot plate in the melting point apparatus equipped with the polarizing microscope. In a crossed Nicols state, the sample was first heated to a temperature allowing the sample to change to the non-liquid crystal isotropic phase, and then cooled at a rate of 1° C./min to make the chiral nematic phase or the optically isotropic liquid crystal phase completely appear. The phase transition temperature during the cooling process was measured. Then, the temperature was raised at a rate of 1° C./min, and the phase transition temperature during the heating process was measured. In the invention, unless particularly indicated, the phase transition temperature in the heating process was described as the phase transition temperature. When it was difficult to determine the phase transition temperature of the optically isotropic liquid crystal phase in a dark field under crossed Nicols, the phase transition temperature was measured after the polarizing plate deviated from the crossed Nicols state by 1 to 10°.

1-5-4) Viscosity (Rotational Viscosity; γ1 (Measured at 25° C.); mPa·s)

(1) For a sample having positive dielectric anisotropy: the measurement was carried out according to a method described in M. Imai et al., Molecular Crystals and Liquid Crystals, Vol. 259, 37 (1995). The sample was put into a TN device having a twist angle of 00 and an interval (cell gap) of 5 m between two glass substrates. A voltage was applied to the TN device stepwise in a range of 16 to 19.5 V at increments of 0.5 V. After a period of 0.2 second with no voltage application, the application of the voltage was repeated under a condition of only one rectangular wave (rectangular pulse; 0.2 second) followed by no application (0.2 second). A peak current and a peak time of a transient current resulting from the application of the voltage were measured. A value of rotational viscosity was obtained according to these measured values and Equation (8) on page 40 of the paper of M. Imai et al. The dielectric anisotropy value required for this calculation was obtained by using the device used in the measurement of the rotational viscosity according to the following method for measuring dielectric anisotropy.

(2) For a sample having negative dielectric anisotropy: the measurement was carried out according to a method described in M. Imai et al., Molecular Crystals and Liquid Crystals, Vol. 259, 37 (1995). The sample was put into a VA device having an interval (cell gap) of 20 µm between two glass substrates. A voltage was stepwise applied to the device in a range of 30 to 50 V at increments of 1 V. After a period of 0.2 second with no voltage application, the application of the voltage was repeated under a condition of only one rectangular wave (rectangular pulse; 0.2 second) followed by no application (0.2 second). The peak current and the peak time of the transient current resulting from the application of the voltage were measured. The value of rotational viscosity was obtained according to these measured values and Equation (8) on page 40 of the paper of M. Imai et al. A value measured according to the dielectric anisotropy described below was used as the dielectric anisotropy value required for this calculation.

1-5-5) Refractive Index Anisotropy (an; Measured at 25° C.)

The measurement was carried out using light having a wavelength of 589 nm by means of the Abbe refractometer having the polarizing plate mounted on the ocular lens. After the surface of the main prism was rubbed in a direction, the sample was dripped onto the main prism. The refractive index ($n_\parallel$) was measured when the polarization direction was parallel to the rubbing direction. The refractive index ($n_\parallel$) was measured when the polarization direction was perpendicular to the rubbing direction. The value of the refractive index anisotropy was calculated according to the equation $\Delta n = n_\parallel - n_\perp$. When the sample is a composition, the refractive index anisotropy was measured by this method.

1-5-6) Dielectric Anisotropy ($\Delta\epsilon$; Measured at 25° C.)

(1) For a composition having positive dielectric anisotropy: the sample was put into the liquid-crystal cell having the interval (gap) of approximately 9 m between two glass substrates and the twist angle of 80 degrees. A voltage of 20 V was applied to the liquid-crystal cell, and permittivity ($\epsilon_\parallel$) in the major axis direction of the liquid-crystal molecule was measured. A voltage of 0.5 V was applied, and permittivity ($\epsilon_\perp$) in the minor axis direction of the liquid-crystal molecule was measured. The value of the dielectric anisotropy was calculated according to the equation $\Delta\epsilon = \epsilon_\parallel - \epsilon_\perp$.

(2) For a composition having negative dielectric anisotropy: the sample was put into a liquid-crystal cell processed into homeotropic alignment, a voltage of 0.5 V was applied and the permittivity ($\epsilon_\parallel$) was measured. The sample was put into a liquid-crystal cell processed into homogeneous alignment, a voltage of 0.5 V was applied and the permittivity ($\epsilon_\perp$) was measured. The value of the dielectric anisotropy was calculated according to the equation $\Delta\epsilon = \epsilon_\parallel - \epsilon_\perp$.

1-5-7) Threshold Voltage (Vth; Measured at 25° C.; V)

(1) For the composition having positive dielectric anisotropy: the sample was put into a liquid-crystal display device in a normally white mode having an interval (gap) of $(0.5/\Delta n)$ µm between two glass substrates and a twist angle of 80°. An is the value of the refractive index anisotropy measured by the above method. A rectangular wave having a frequency of 32 Hz was applied to the device. A voltage of the rectangular wave was increased, and a voltage value at which transmittance of light passing through the device reached 90% was measured.

(2) For the composition having negative dielectric anisotropy: the sample was put into a liquid-crystal display device in a normally black mode that was processed into homeotropic alignment and that has an interval (gap) of approximately 9 m between two glass substrates. A rectangular wave having a frequency of 32 Hz was applied to the device. A voltage of the rectangular wave was increased, and a voltage value at which transmittance of light passing through the device reached 10% was measured.

1-5-8) Voltage Holding Ratio (VHR; Measured at 25° C.; %) A TN device used for the measurement has a polyimide alignment film and an interval (cell gap) of 6 µm between two glass substrates. A sample was put into the device, which was then sealed with a UV-polymerizable adhesive. The TN device was charged by applying a pulse voltage (60 microseconds at 5 V) thereto. An attenuating voltage was measured for 16.7 milliseconds with a high-speed voltmeter, and an area A between a voltage curve and a horizontal axis in a unit cycle was obtained. An area B is an area where no attenuation occurs.

The voltage holding ratio is a percentage of the area A with respect to the area B.

Helical Pitch (P; Measured at 20 to 25° C.; Nm) The helical pitch was measured by a Grandjean-Cano wedge cell method. A sample was injected into a Grandjean-Cano wedge cell, and an interval (a; unit: m) between disclination lines observed from the cell was measured. The helical pitch (p) was calculated according to an equation $p = 2 \cdot a \cdot \tan\theta$. $\theta$ is an angle between two glass plates in the wedge cell.

Alternatively, the pitch length was measured through selective reflection (Handbook of Liquid Crystal, p. 196, 2000, Maruzen). For the selective reflection wavelength $\lambda$, the relationship $<n> p/\lambda = 1$ exists. Here, $<n>$ represents the average refractive index, and is calculated according to the equation: $<n> = \{(n_\parallel^2 + n_\perp^2)/2\}^{1/2}$. The selective reflection wavelength was measured by a microspectrophotometer (trade name: MSV-350, made by Japan Electronics Co., Ltd.). The pitch was obtained by dividing the resultant reflection wavelength by the average refractive index.

In a region of low concentration of the chiral agent, the pitch of the cholesteric liquid crystal having the reflection wavelength in the region of wavelength longer than that of visible light is proportional to a reciprocal of the concentration of the chiral agent. Therefore, several points were measured for the pitch length of the liquid crystal having the selective reflection wavelength in the visible light region, and the pitch was obtained by a linear extrapolation method.

1-6) Permittivity ($\epsilon'$ (PSBP), 25° C.) of Polymer/Liquid-Crystal Composite Material The permittivity was measured using an LCR meter (E4980A, Agilent) according to a four-terminal pair method. A parallel plate cell (electrode material: ITO, distance between electrodes: 4 µm, electrode area: 0.16 cm$^2$) was used as a measurement cell. The measurement conditions were as follows.

Measurement temperature: 25° C.
Application waveform: sine wave
Applied voltage: 2.0 V
Measurement frequency: 100 Hz In addition, a ratio (percentage) of a component or a liquid crystal compound is expressed in terms of weight percentage (wt %) based on the total weight of the liquid crystal compound. A composition is prepared by measuring weight of the components such as the liquid crystal compounds, and then mixing the components. Accordingly, calculation of wt % of the components is easy.
Example 1
A compound (1-1-1S) of this application was synthesized according to the following scheme.
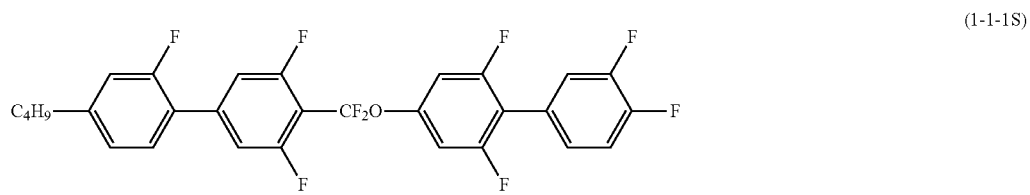
(Compound of formula (1-1-1) with $R^{14}$ being butyl)
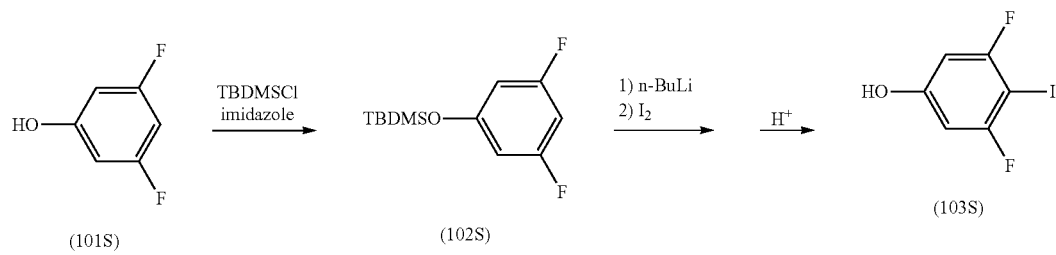
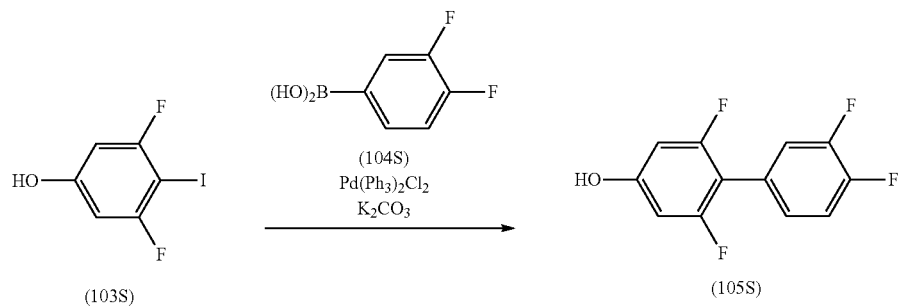
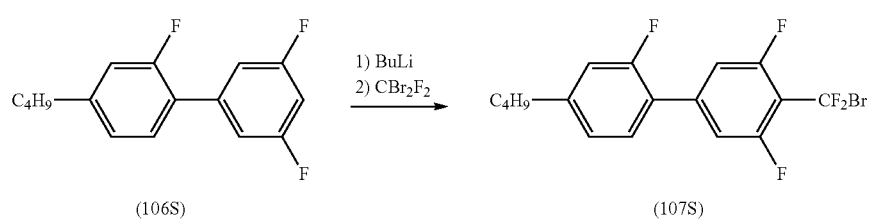

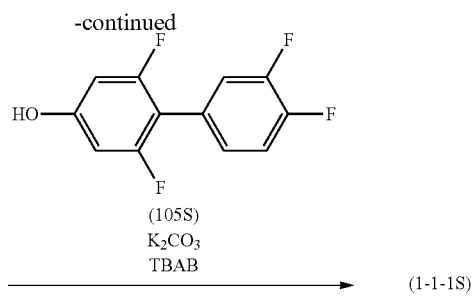

(105S)
K₂CO₃
TBAB (1-1-1S)

(Stage 1) Synthesis of Compound (102S)

Under a nitrogen gas stream, a solution of a compound (101S) (30.0 g, 0.230 mol) and imidazole (36.1 g, 0.531 mol) in dichloromethane (210 mL) was cooled to 0 to 10° C., t-butyldimethylchlorosilane (38.2 g, 0.254 mol) was slowly added, and the resultant was stirred for 3 hours while the temperature was maintained. The reaction solution was poured in water, and dichloromethane (200 mL) was added. An organic phase was concentrated under reduced pressure after being washed three times with water. The residue was purified by silica gel column chromatography (solvent: toluene/n-heptane=1/5) to obtain a compound (102S) (56.0 g, 0.228 mol).

(Stage 2) Synthesis of Compound (103S)

Under a nitrogen gas stream, an n-butyl lithium/n-hexane solution (1.60 mol/L) (157 mL, 0.252 mol) was slowly dripped in a solution of the compound (102S) (56.0 g, 0.229 mol) in THF (400 mL) at −40° C., and the resultant was stirred for 1 hour while the temperature was maintained. Next, a solution of iodine (69.7 g, 0.275 mol) in THF (150 mL) was slowly dripped in the system while the temperature was maintained, and the resultant was stirred for 30 minutes while the temperature was maintained. After that, the resultant was stirred for 1 hour while the temperature was gradually returned to room temperature. The reaction solution was poured into water, and extracted twice with toluene (500 mL). The organic phase was concentrated under a reduced pressure after being washed twice with a sodium thiosulfate aqueous solution and three times with water to obtain a crude product (83.0 g, 0.227 mol). A THF solution (1.0 M) (400 mL, 0.400 mol) of tetrabutylammonium fluoride was added to the resultant crude product (83.0 g, 0.227 mol), and the resultant was stirred at 30° C. for 3 hours. The reaction solution was poured into water, and extracted twice with toluene (500 mL). The organic phase was concentrated under reduced pressure after being washed three times with water. The residue was purified by silica gel column chromatography (solvent: toluene/ethyl acetate=1/10) to obtain a compound (103S) (56.8 g, 0.222 mol).

(Stage 3) Synthesis of Compound (105S)

Under a nitrogen gas stream, a mixed solution of the compound (103S) (56.8 g, 0.222 mol), a compound (104S) (36.8 g, 0.233 mol), potassium carbonate (64.3 g, 0.466 mol), palladium/carbon (NX-Type) (1.70 g), tetrabutylammonium bromide (7.14 g, 0.0222 mol), toluene (200 mL) and isopropanol (200 mL) was heated and stirred at 80° C. for 5 hours. The reaction solution was poured in water, and diethyl ether (500 mL) was added. The organic phase was concentrated under reduced pressure after being washed three times with water. The residue was purified by silica gel column chromatography (solvent: toluene/ethyl acetate=1/10), and then by recrystallization-filtration (solvent: heptane/THF=10/1) to obtain a compound (105S) (28.0 g, 0.116 mol).

(Stage 4) Synthesis of Compound (107S)

Under a nitrogen gas stream, an n-butyl lithium/n-hexane solution (1.62 mol/L) (74.0 mL, 0.120 mol) was slowly dripped in a solution of a compound (106S) (30.0 g, 0.114 mol) in THF (130 mL) at −40° C., and the resultant was stirred for 1 hour while the temperature was maintained. Next, a dibromodifluoroethane (28.8 g, 0.137 mol)/THF (70 mL) solution was slowly dripped in the system while the temperature was maintained, and the resultant was stirred for 1 hour while the temperature was gradually returned to room temperature. The reaction solution was poured into water, and extracted with toluene (250 mL). The organic phase was concentrated under reduced pressure after being washed three times with water. The residue was purified by silica gel column chromatography (solvent: toluene/n-heptane=1/1) to obtain a compound (107S) (45.5 g (78%), 0.115 mol). In the next reaction, the mixture was used directly.

(Stage 5) Synthesis of Compound (1-1-1S)

Under a nitrogen gas stream, a mixed solution of the compound (105S) (3.23 g, 13.4 mmol) obtained in stage 3, the compound (107S) (7.00 g (78%), 13.4 mmol) obtained in the previous stage, potassium carbonate (3.87 g, 28.0 mmol), tetrabutylammonium bromide (1.29 g, 4.01 mmol) in 1,4-dioxane (40 mL) was heated and stirred at 70° C. for 2 hours. The reaction solution was poured into water, and extracted with toluene (100 mL). The organic phase was concentrated under reduced pressure after being washed three times with water and twice with sodium bicarbonate water. The residue was purified by silica gel column chromatography (solvent: toluene/n-heptane=1/5), and then by recrystallization-filtration (solvent: ethanol/n-heptane=1/1) to obtain the compound (1-1-1S) (4.30 g, 7.76 mmol) as a final product. A phase transition temperature (° C.) of this compound was C 73.3N 83.3 I.

$^1$H-NMR (CDCl$_3$): δ (ppm) 0.939-0.968 (3H, t), 1.35-1.42 (2H, m), 1.60-1.67 (2H, m), 2.65-2.68 (2H, t), 6.98-7.04 (1H, dd), 7.06-7.08 (1H, dd), 7.21-7.25 (6H, in), 7.32-7.36 (2H, t).

$^{19}$F-NMR (CDCl$_3$): δ (ppm)--61.87--61.98 (2F, t), −111.32--111.46 (2F, dt), −112.94--112.95 (2F, d), −118.31--118.36 (1F, dd), −137.96--138.13 (2F, m).

Next, the four compounds described above as the mother liquid crystal A were mixed together to prepare a mother liquid crystal A having the nematic phase. Physical properties of this mother liquid crystal A were as follows.

Upper-limit temperature ($T_{NI}$)=71.7° C.; dielectric anisotropy (Δ∈)=11.0; refractive index anisotropy (Δn)=0.137.

A liquid crystal composition AS1 including the mother liquid crystal A (85 wt %) and the resultant compound (1-1-1S) (15 wt %) was prepared. Physical properties of the resultant liquid crystal composition AS1 were measured, and extrapolated values of physical properties of the compound (1-1-1S) were calculated by extrapolating the measured values. The values were as follows.

Upper-limit temperature $(T_{NI})$=53.0° C.; dielectric anisotropy (A)=42.1; refractive index anisotropy (Δn)=0.164.

From this, it is known that the compound (1-1-1S) is a compound having large dielectric anisotropy (Δ∈), large refractive index anisotropy and good compatibility.

Example 2

A compound (1-3-1S) of this application was synthesized according to the following scheme.

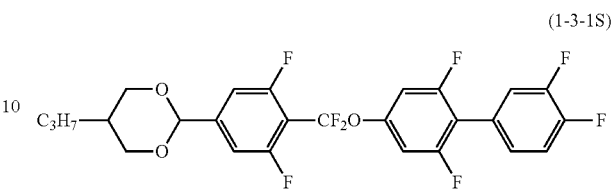

(1-3-1S)

(Compound of formula (1-3-1) with $R^{1A}$ being propyl)

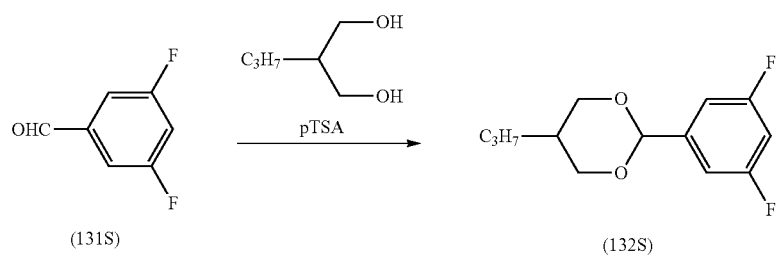

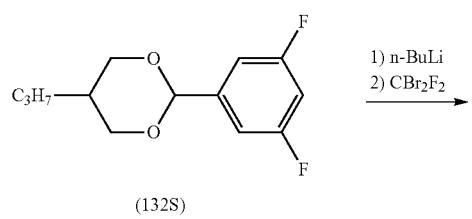

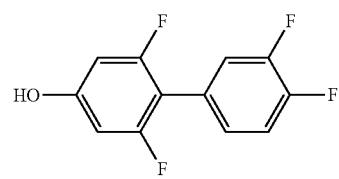

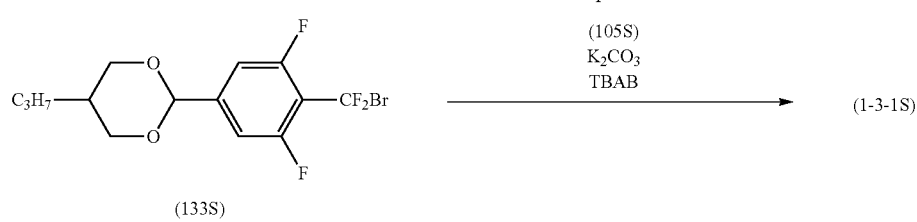

(Stage 1) Synthesis of Compound (132S)

Under a nitrogen gas stream, a solution of a compound (131S) (60.0 g, 0.422 mol), 2-propylpropan-1,3-diol (54.8 g, 0.464 mol), and p☐toluenesulfonic acid monohydrate (1.80 g) in toluene (300 mL) was heated under reflux at 110° C. for 2 hours while generated water was removed from the system. The reaction solution was poured into water, and toluene (200 mL) was added. The organic phase was concentrated under reduced pressure after being washed three times with water. The residue was purified by silica gel column chromatography (solvent: toluene/n-heptane=1/1) to obtain a compound (132S) (94.0 g, 0.388 mol).

(Stage 2) Synthesis of Compound (133S)

Under a nitrogen gas stream, an n-butyl lithium/n-hexane solution (1.65 mol/L) (121 mL, 0.200 mol) was slowly dripped in a solution of the compound (132S) (50.0 g, 0.206 mol) in THF (500 mL) at −40° C., and the resultant was stirred for 1 hour while the temperature was maintained. Next, a dibromodifluoromethane (51.8 g, 0.247 mol)/THF (50 mL) solution was slowly dripped in the system while the temperature was maintained, and the resultant was stirred for 1 hour while the temperature was gradually returned to room temperature. The reaction solution was poured into water, and extracted twice with toluene (400 mL). The organic phase was concentrated under reduced pressure after being washed three times with water. The residue was purified by silica gel column chromatography (solvent: toluene/n-heptane=1/2) to obtain a compound (133S) (67.1 g (72%), 0.132 mol). In the next reaction, the mixture was used directly.

(Stage 3) Synthesis of Compound (1-3-1 S)

Under a nitrogen gas stream, a mixed solution of the compound (105S) (3.28 g, 13.6 mmol) obtained in stage 5 of Example 1, the compound (133S) (7.00 g (72%), 13.6 mmol) obtained in the previous stage, potassium carbonate (3.94 g, 28.5 mmol), tetrabutylammonium bromide (1.31 g, 4.07 mmol) in 1,4-dioxane (35 mL) was heated and stirred at 70° C. for 2 hours. The reaction solution was poured into water, and extracted with toluene (100 mL). The organic phase was concentrated under reduced pressure after being washed three times with water and twice with sodium bicarbonate water. The residue was purified by silica gel column chromatography (solvent: toluene/n-heptane=1/1), and then by recrystallization-filtration (solvent: ethanol/n-heptane=2/1) to obtain the compound (1-3-1S) (4.00 g, 7.51 mmol) as a final product. A phase transition temperature (° C.) of this compound was C 85.2 N 90.3 I.

$^1$H-NMR (CDCl$_3$): δ (ppm) 0.917-0.946 (3H, t), 1.07-1.12 (2H, m), 1.31-1.38 (2H, m), 2.01-2.15 (1H, m), 3.51-3.55 (2H, dd), 4.22-4.26 (2H, dd), 5.38 (1H, s), 6.93-6.98 (2H, d), 7.14-7.19 (3H, m), 7.22-7.26 (1H, m), 7.26-7.30 (1H, m).

$^{19}$F-NMR (CDCl$_3$): δ (ppm) −61.75--−61.86 (2F, t), −110.49--−110.63 (2F, dt), −112.90--−112.92 (2F, d), −138.02--−118.36 (1F, dd), −137.96--−138.13 (2F, in).

A liquid crystal composition AS2 including the mother liquid crystal A (85 wt %) and the resultant compound (1-3-1S) (15 wt %) was prepared. Physical properties of the resultant liquid crystal composition AS2 were measured, and extrapolated values of physical properties of the compound (1-3-1S) were calculated by extrapolating the measured values. The values were as follows.

Upper-limit temperature (T$_{NI}$)=63.0° C.; dielectric anisotropy (Δ∈)=41.4; refractive index anisotropy (Δn)=0.124.

From this, it is known that the compound (1-3-1S) is a compound having large dielectric anisotropy (Δ∈), large refractive index anisotropy and good compatibility.

Example 3

A compound (1-1-2S) of this application was synthesized according to the same scheme as that in Example 1.

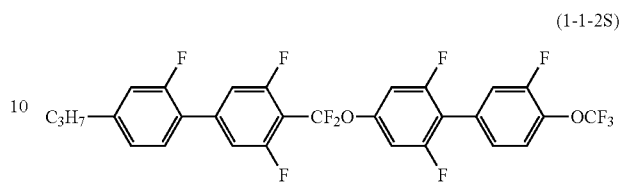

(1-1-2S)

(Compound of formula (1-1-2) with R$^{1,4}$ being propyl)

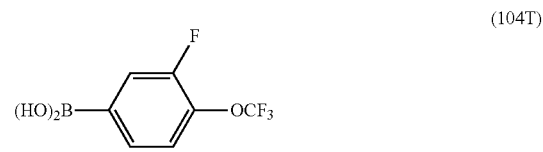 [SMILES: OB(O)c1ccc(OC(F)(F)F)c(F)c1]

(104T)

By the same method as in Example 1 and by use of a compound in which the alkyl chain in the compound (106S) is propyl and a compound (104T) in place of the compound (104S), the compound (1-1-2S) (4.4 g, 7.26 mmol) was obtained. A phase transition temperature (° C.) of this compound was C 52.9 N 111.5 I.

$^1$H-NMR (CDCl$_3$): δ (ppm) 0.962-0.991 (3H, t), 1.65-1.72 (2H, m), 2.63-2.66 (2H, t), 7.00-7.03 (3H, m), 7.07-7.08 (1H, dd), 7.22-7.24 (2H, d), 7.26-7.28 (1H, dd), 7.33-7.36 (2H, m), 7.38-7.41 (1H, dt).

$^{19}$F-NMR (CDCl$_3$): δ (ppm) −59.08--−59.13 (3F, d), −61.88--−61.99 (2F, t), −111.30--−111.44 (2F, dt), −112.75--−112.77 (2F, d), −118.31--−118.36 (1F, dd), −128.94--−129.00 (1F, in).

A liquid crystal composition AS3 including the mother liquid crystal A (85 wt %) and the resultant compound (1-1-2S) (15 wt %) was prepared. Physical properties of the resultant liquid crystal composition AS3 were measured, and extrapolated values of physical properties of the compound (1-1-2S) were calculated by extrapolating the measured values. The values were as follows.

Upper-limit temperature (T$_{NI}$)=61.7° C.; dielectric anisotropy (Δ∈)=48.1; refractive index anisotropy (Δn)=0.170.

From this, it is known that the compound (1-1-2S) is a compound having large dielectric anisotropy (Δ∈), large refractive index anisotropy and good compatibility.

Example 4

A compound (1-1-3S) of this application was synthesized according to the same scheme as that in Example 1.

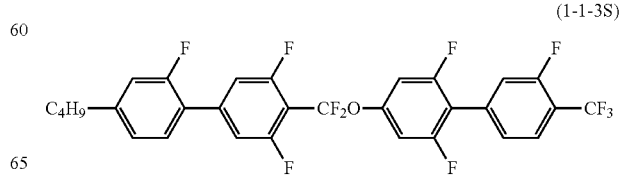

(1-1-3S)

(Compound of formula (1-1-3) with $R^{1.4}$ being butyl)

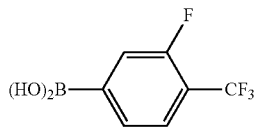
(104U)

By the same method as in Example 1 and by use of a compound (104U) in place of the compound (104S), the compound (1-1-3S) (8.7 g, 14.4 mmol) was obtained. A phase transition temperature (° C.) of this compound was C 81.8 (N 74.1) I.

$^1$H-NMR (CDCl$_3$): δ(ppm) 0.939-0.968 (3H, t), 1.35-1.41 (2H, m), 1.60-1.65 (2H, m), 2.65-2.68 (2H, t), 7.01-7.04 (3H, in), 7.07-7.09 (1H, dd), 7.22-7.24 (2H, d), 7.32-7.37 (3H, m), 7.68-7.71 (1H, t).

$^{19}$F-NMR (CDCl$_3$): δ (ppm) −61.91--−61.94 (3F, d), −61.91--−62.02 (2F, t), −111.32--−111.45 (2F, dt), −112.58--−112.59 (2F, d), −114.63--−114.75 (1F, m), −118.31--−118.35 (1F, dd).

A liquid crystal composition AS4 including the mother liquid crystal A (85 wt %) and the resultant compound (1-1-3S) (15 wt %) was prepared. Physical properties of the resultant liquid crystal composition AS4 were measured, and extrapolated values of physical properties of the compound (1-1-3S) were calculated by extrapolating the measured values. The values were as follows.

Upper-limit temperature ($T_{NI}$)=39.7° C.; dielectric anisotropy (Δ∈)=57.9; refractive index anisotropy (Δn)=0.150.

From this, it is known that the compound (1-1-3S) is a compound having large dielectric anisotropy (Δ∈), large refractive index anisotropy and good compatibility.

Example 5

A compound (1-1-3T) of this application was synthesized according to the same scheme as that in Example 1.

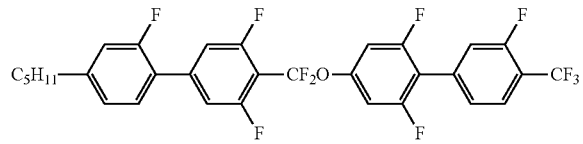
(1-1-3T)

(Compound of formula (1-1-3) with $R^{1.4}$ being butyl)

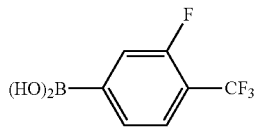
(104U)

By the same method as in Example 1 and by use of a compound in which the alkyl chain in the compound (106S) is butyl and the compound (104U) in place of the compound (104S), the compound (1-1-3T) (6.1 g, 9.86 mmol) was obtained. A phase transition temperature (° C.) of this compound was C 63.5 (SmA 61.8) N 81.8 I.

$^1$H-NMR (CDCl$_3$): δ (ppm) 0.899-0.953 (3H, t), 1.30-1.40 (4H, m), 1.64-1.67 (2H, m), 2.64-2.67 (2H, t), 7.01-7.04 (3H, m), 7.07-7.08 (1H, dd), 7.22-7.26 (2H, d), 7.32-7.37 (3H, m), 7.68-7.71 (1H, t).

$^{19}$F-NMR (CDCl$_3$): δ (ppm) −61.91--−61.93 (3F, d), −61.82--−62.00 (2F, t), −111.31--−111.44 (2F, dt), −112.52--−112.58 (2F, d), −114.61--−114.73 (1F, m), −118.28--−118.33 (1F, dd).

A liquid crystal composition AS5 including the mother liquid crystal A (85 wt %) and the resultant compound (1-1-3T) (15 wt %) was prepared. Physical properties of the resultant liquid crystal composition AS5 were measured, and extrapolated values of physical properties of the compound (1-1-3T) were calculated by extrapolating the measured values. The values were as follows.

Upper-limit temperature ($T_{NI}$)=45.7° C.; dielectric anisotropy (Δ∈)=56.8; refractive index anisotropy (Δn)=0.157.

From this, it is known that the compound (1-1-3T) is a compound having large dielectric anisotropy (Δ∈), large refractive index anisotropy and good compatibility.

Example 6

A compound (1-3-2S) of this application was synthesized according to the same scheme as that in Example 2.

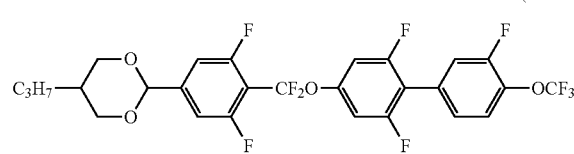
(1-3-2S)

(Compound of formula (1-3-2) with $R^{1.4}$ being propyl)

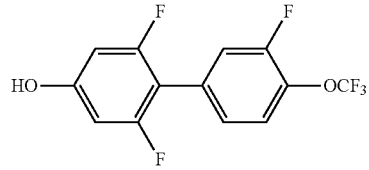
(105T)

By the same method as in Example 2 and by use of a compound (105T) in place of the compound (105S), the compound (1-3-2S) (3.8 g, 6.35 mmol) was obtained. A phase transition temperature (° C.) of this compound was C 93.7 N 96.8 I.

$^1$H-NMR (CDCl$_3$): δ (ppm) 0.918-0.947 (3H, t), 1.07-1.12 (4H, dt), 1.31-1.37 (2H, m), 2.11-2.15 (1H, m), 3.51-3.55 (2H, dd), 4.23-4.26 (2H, m), 5.38 (1H, s), 6.95-6.99 (2H, d), 7.14-7.16 (2H, d), 7.25-7.26 (1H, dd), 7.31-7.34 (1H, dd), 7.37-7.40 (1H, dd).

$^{19}$F-NMR (CDCl$_3$): δ (ppm) −59.13--−59.14 (3F, d), −61.78--−61.89 (2F, t), −110.49--−110.63 (2F, dt), −112.73--−112.75 (2F, d), −128.98--−129.05 (1F, m).

A liquid crystal composition AS6 including the mother liquid crystal A (90 wt %) and the resultant compound (1-3-2S) (10 wt %) was prepared. Physical properties of the resultant liquid crystal composition AS6 were measured, and extrapolated values of physical properties of the compound (1-3-2S) were calculated by extrapolating the measured values. The values were as follows.

Upper-limit temperature ($T_{NI}$)=67.7° C.; dielectric anisotropy ($\Delta\epsilon$)=43.1; refractive index anisotropy ($\Delta n$)=0.137.

From this, it is known that the compound (1-3-2S) is a compound having large dielectric anisotropy ($\Delta\epsilon$), large refractive index anisotropy and good compatibility.

Example 7

A compound (1-5-1 S) of this application was synthesized according to the same scheme as that in Example 1.

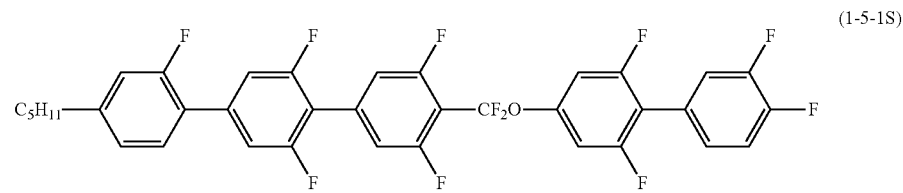

(1-5-1S)

(Compound of formula (1-5-1) with $R^{1,4}$ being pentyl).

Example 8

Preparation of nematic liquid crystal composition (NLC)

Nematic liquid crystal compositions NLC-A to NLC-C including the compound (1-1-1S) synthesized in Example 1 or 2 or the compound (1-3-1S) were prepared by mixing the compounds shown below. In addition, a liquid crystal composition NLC-R was prepared as a comparative example. NLC-A to NLC-C are compositions in which a part of the compounds of NLC-R was replaced with the compound (1).

TABLE 1

Composition of Nematic Liquid Crystal Compositions

| Compound | | NLC-A | NLC-B | NLC-C | NLC-R (Comparative Example) |
|---|---|---|---|---|---|
| C5H11—[structure]—CF2O—[structure]—F | (3-3) | 1.96 | 2.30 | 2.30 | 2.30 |
| C4H9—[structure]—CF2O—[structure]—F | (3-3) | 1.96 | 2.30 | 2.30 | 2.30 |
| C5H11—[structure]—CF2O—[structure]—F | (3-2) | 2.55 | — | 3.00 | 3.00 |
| C4H9—[structure]—CF2O—[structure]—F | (3-2) | 2.55 | — | 3.00 | 3.00 |

TABLE 1-continued

Composition of Nematic Liquid Crystal Compositions

| Structure | | NLC-A | NLC-B | NLC-C | NLC-R (Comparative Example) |
|---|---|---|---|---|---|
| C₃H₇—[2-F phenyl]—[3,5-diF phenyl]—CF₂O—[2-F phenyl]—[3,5-diF phenyl]—F | (3-2) | 2.55 | — | 3.00 | 3.00 |
| C₆H₁₃—[2-F phenyl]—[3,5-diF phenyl]—[3,5-diF phenyl]—CF₂O—[3,5-diF phenyl]—CF₃ | (3-3) | 3.19 | 3.75 | 3.75 | 3.75 |
| C₅H₁₁—[2-F phenyl]—[3,5-diF phenyl]—[3,5-diF phenyl]—CF₂O—[3,5-diF phenyl]—CF₃ | (3-3) | 3.19 | 3.75 | 3.75 | 3.75 |
| C₄H₉—[2-F phenyl]—[3,5-diF phenyl]—[3,5-diF phenyl]—CF₂O—[3,5-diF phenyl]—CF₃ | (3-3) | 3.19 | 3.75 | 3.75 | 3.75 |
| C₃H₇—[2-F phenyl]—[3,5-diF phenyl]—[3,5-diF phenyl]—CF₂O—[3,5-diF phenyl]—CF₃ | (3-3) | 3.19 | 3.75 | 3.75 | 3.75 |
| C₅H₁₁—[dioxane]—[2,6-diF phenyl]—CF₂O—[2-F phenyl]—[3,5-diF phenyl]—F | (7-2-5) | 12.75 | 15.00 | 15.00 | 15.00 |
| C₄H₉—[dioxane]—[2,6-diF phenyl]—CF₂O—[2-F phenyl]—[3,5-diF phenyl]—F | (7-2-5) | 12.75 | 15.00 | 15.00 | 15.00 |
| C₃H₇—[dioxane]—[2,6-diF phenyl]—CF₂O—[2-F phenyl]—[3,5-diF phenyl]—F | (7-2-5) | 12.75 | 15.00 | — | 15.00 |

TABLE 1-continued

Composition of Nematic Liquid Crystal Compositions

| Structure | Code | NLC-A | NLC-B | NLC-C | NLC-R (Comparative Example) |
|---|---|---|---|---|---|
| 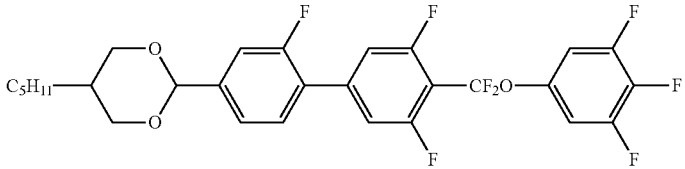 | (7-2-4) | 7.65 | 9.00 | 9.00 | 9.00 |
| 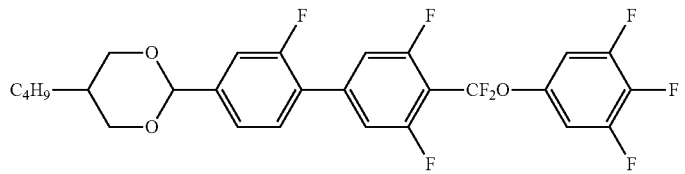 | (7-2-4) | 7.65 | 9.00 | 9.00 | 9.00 |
| 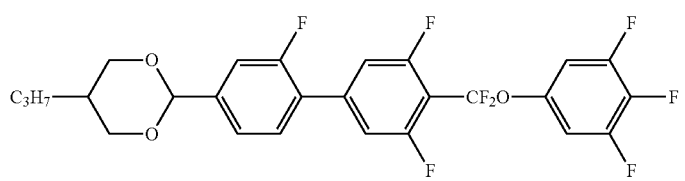 | (7-2-4) | 7.14 | 8.40 | 8.40 | 8.40 |
| 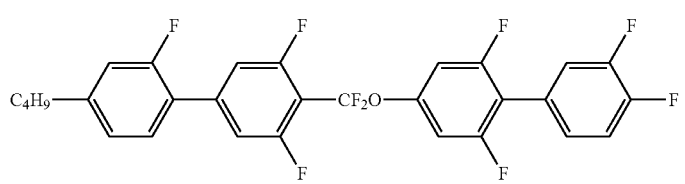 | (1-1-1S) | 15.00 | 9.00 | — | — |
| 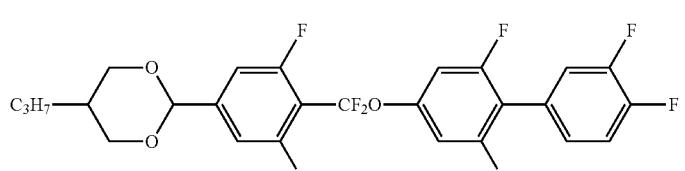 | (1-3-1S) | — | — | 15.00 | — |

Phase transition temperatures (° C.) of NLC-A to NLC-C and NLC-R were as shown in Table 2 below.

TABLE 2

N-I Transition Point of Nematic Liquid crystal compositions

| NLC | NLC-A | NLC-B | NLC-C | NLC-R |
|---|---|---|---|---|
| N-I Transition Point (° C.) | 87.7 | 87.7 | 88.9 | 87.8 |

Example 9

Preparation of chiral liquid crystal composition (CLC)

Chiral liquid crystal compositions CLC-A to CLC-C and CLC-R were prepared by mixing the nematic liquid crystal compositions obtained in Example 8 with a chiral agent (CD1) shown below. Compositions and phase transition temperatures of the chiral liquid crystal compositions were as shown in Table 3 below. Moreover, a structure of CD1 in the table is

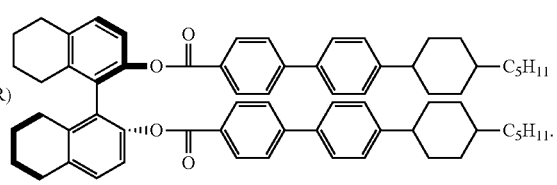

TABLE 3

Composition and phase transition point of chiral liquid crystal compositions

| CLC<br>NLC Contained | | CLC-A<br>NLC-A | CLC-B<br>NLC-B | CLC-C<br>NLC-C | CLC-R<br>NLC-R |
|---|---|---|---|---|---|
| Composition (wt %) | NLC | 95.2 | 95.2 | 95.2 | 95.2 |
| | CD-1 | 4.8 | 4.8 | 4.8 | 4.8 |
| Phase | N*-BP | 79.5-79.7 | 80.1-80.3 | 81.1-81.3 | 79.8-80.1 |

TABLE 3-continued

Composition and phase transition point of chiral liquid crystal compositions

| CLC<br>NLC Contained | CLC-A<br>NLC-A | CLC-B<br>NLC-B | CLC-C<br>NLC-C | CLC-R<br>NLC-R |
|---|---|---|---|---|
| Transition (° C.) | BP-(BP + Iso) | — | 81.0 | 82.1 | 81.2 |
| | (BP + Iso)-Iso. | — | 81.9 | 82.7 | 81.6 |

Example 10

Preparation of Liquid Crystal Composition (MLC) being Mixture with Polymerizable Monomer Liquid crystal compositions MLC-A to MLC-C and MLC-R were prepared by heating and mixing, in an isotropic phase, a mixture of the chiral liquid crystal compositions (CLC) prepared in Example 9 with a polymerizable monomer. Compositions and phase transition points (° C.) of these liquid crystal compositions are shown in Table 4 below.

Moreover, LCA-12 is 1,4-di(4-(6-(acryloyloxy)dodecyloxy)benzoyloxy)-2-methylbenzene, and DMPA is 2,2'-dimethoxyphenylacetophenone and is a photopolymerization initiator.

Example 11

Preparation of a Cell Having a Polymer/Liquid-Crystal Composite Material Sandwiched Therein The liquid crystal composition (MLC-A to MLC-C) being a mixture of the chiral liquid crystal composition obtained in Example 10 with a polymerizable monomer was interposed between a comb-shaped electrode substrate having no alignment treatment applied thereon and an opposite glass substrate (with no electrode), and the resultant was heated to a blue phase.

In this state, a polymerization reaction was performed by irradiating the resultant with UV light (UV light intensity: 23 mWcm$^{-2}$ (365 nm)) for 1 minute. Thus, cells having polymer/liquid-crystal composite materials (PSBP-A to PSBP-C) sandwiched therein were prepared (cell thickness: 7 to 9 μm). The resultant polymer/liquid-crystal composite materials (PSBP-A to PSBP-C) maintained the optically isotropic liquid crystal phase even when cooled to room temperature.

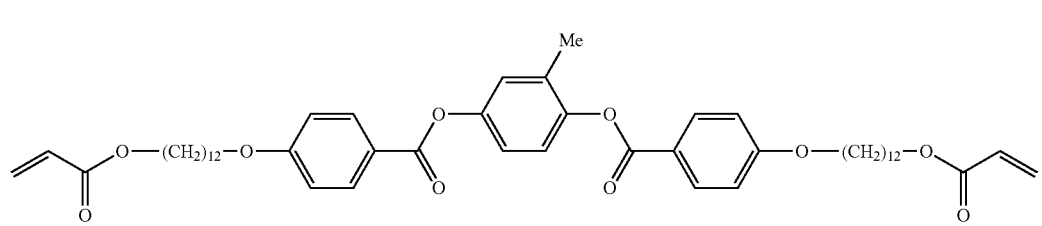

LCA-12

TABLE 4

Composition and phase transition point of mixtures of monomers and chiral liquid crystal compositions

| | MLC<br>CLC Contained | MLC-A<br>CLC-A | MLC-B<br>CLC-B | MLC-C<br>CLC-C | MLC-R<br>CLC-R |
|---|---|---|---|---|---|
| Composition (wt %) | CLC | 88.4 | 88.4 | 88.4 | 88.4 |
| | n-hexadecylacrylate | 6.2 | 6.2 | 6.2 | 6.2 |
| | LCA-12 | 5.0 | 5.0 | 5.0 | 5.0 |
| | DMPA | 0.4 | 0.4 | 0.4 | 0.4 |
| Phase Transition Heating (° C.) | N*-BP | 51.2-51.4 | 52.1-52.5 | 52.3-52.8 | 52.2-52.7 |
| | BP-(BP + Iso) | 54.4 | 55.3 | 55.8 | 53.7 |
| | (BP + Iso)-Iso. | 56.1 | 57.5 | 57.7 | 57.3 |
| Phase Transition Cooling (° C.) | Iso-BP | 54.8 | 55.0 | 55.8 | 55.7 |
| | Iso-(Iso + BP) | — | — | — | — |
| | BP-N* | 48.9 | 49.1 | 50.0 | 50.9 |

Comparative Example 1

Preparation of a Cell Having a Polymer/Liquid-Crystal Composite Material Sandwiched Therein The liquid crystal composition (MLC-R) being a mixture of the chiral liquid crystal composition obtained in Example 10 with a polymerizable monomer was interposed between a comb-shaped electrode substrate having no alignment treatment applied thereon and an opposite glass substrate (with no electrode), and the resultant was heated to a blue phase.

In this state, a polymerization reaction was performed by irradiating the resultant with UV light (UV light intensity: 23 mWcm$^{-2}$ (365 nm)) for 1 minute. Thus, a cell having a polymer/liquid-crystal composite material (PSBP-R) sandwiched therein was prepared (cell thickness: 7 to 9 μm). The thus obtained polymer/liquid-crystal composite material (PSBP-R) maintained the optically isotropic liquid crystal phase even when cooled to room temperature.

Example 12

Optical System Using Cell

Figure 2:
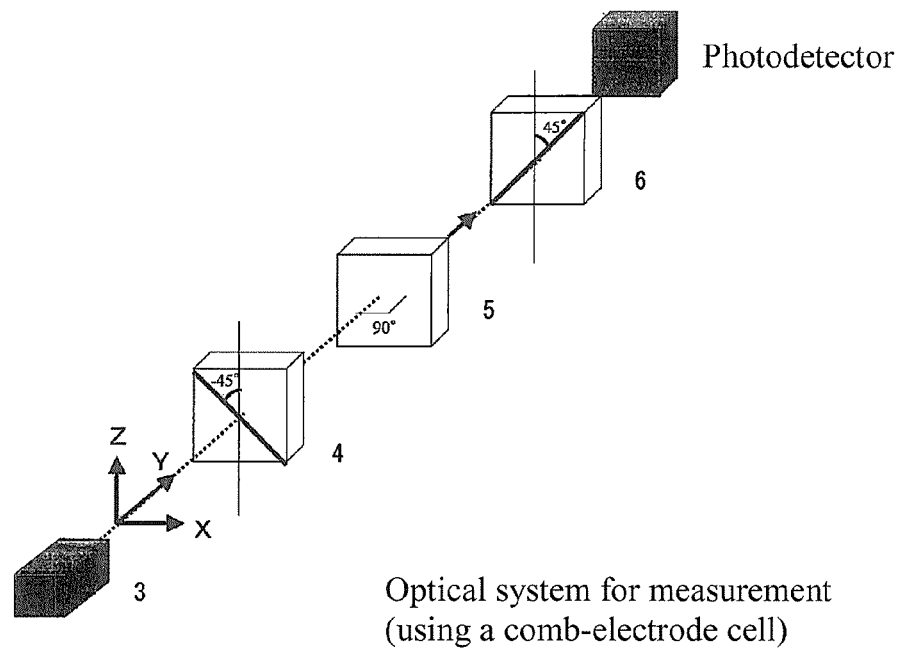
FIG. 2 shows an optical system used in the Examples.

The cell having the polymer/liquid-crystal composite material sandwiched therein as obtained in Example 11 and in Comparative Example 1 was set to an optical system shown in FIG. 2. Specifically, a white light source of a polarizing microscope (ECLIPSE LV100POL made by Nikon Corporation) was used as a light source 3, and the cell 5 having the polymer/liquid-crystal composite material sandwiched therein was set so that an incidence angle on the cell was perpendicular to the cell surface and a line direction of the comb-shaped electrode was 45° with respect to each of the polarizer 4 and the analyzer 6 polarizing plates (FIG. 2).

A relationship between applied voltage and transmittance of each of the polymer/liquid-crystal composite materials (PSBP-A to PSBP-C and PSBP-R) at room temperature was investigated using the optical system. Saturation voltage (Vmax), transmittance (%) during application of the saturation voltage, contrast ratio and response rate (ms) of the polymer/liquid-crystal composite materials (PSBP-A to PSBP-C and PSBP-R) sandwiched in the cell were as shown in Table 5. Moreover, the data of the response rate is that when the saturation voltage is applied and removed.

Furthermore, the permittivity ($\epsilon'$ (PSBP)) of the polymer/liquid-crystal composite materials (PSBP-A to PSBP-C and PSBP-R) was measured by the previously described method. The permittivity ($\epsilon'$ (PSBP)) of the polymer/liquid-crystal composite materials (PSBP-A to PSBP-C and PSBP-R) was as shown in Table 5.

From Table 5, PSBP-A to PSBP-C have a saturation voltage (Vmax) ranging from 53.4 to 59.3 (V) and permittivity ($\epsilon'$ (PSBP)) ranging from 65.1 to 68.4. PSBP-R shown as the comparative example has a saturation voltage (Vmax) of 55.9 (V) and permittivity ($\epsilon'$ (PSBP)) of 80.6. From this result, it is known that although the saturation voltage of PSBP-A to PSBP-C is on the same level as that of PSBP-R, the permittivity of PSBP-A to PSBP-C is approximately 12 to 15 lower than that of PSBP-R. It is known that the compound (1) is a compound effective for reducing permittivity of a polymer/liquid-crystal composite material.

Example 13

Preparation of Nematic Liquid Crystal Composition (NLC)

Nematic liquid crystal compositions NLC-D to NLC-H including the compound (1-1-2S), (1-1-3S), (1-1-3T) or (1-3-2S) synthesized in Examples 3 to 6 were prepared by mixing the compounds shown in Table 6 below. In addition, a liquid crystal composition NLC-S was prepared as a comparative example. NLC-D to NLC-H are compositions in which a part of the compounds of NLC-S was replaced with the compound (1).

TABLE 5

Preparation Conditions and Physical Property Values of Polymer/Liquid Crystal Composite Materials

| | PSBP | | | |
|---|---|---|---|---|
| MLC Used | PSBP-A MLC-A | PSBP-B MLC-B | PSBP-C MLC-C | PSBP-R (Comparative Example) MLC-R |
| Polymerization Temperature (° C.) | 51.3 | 51.9 | 52.5 | 52.4 |
| Vmax (V) | 59.3 | 53.4 | 55.9 | 55.9 |
| Transmittance (%) During Application of Vmax | 85.7 | 84.6 | 85.2 | 89.9 |
| Contrast Ratio | 911.2 | 726.3 | 837.8 | 840.1 |
| V10-90 (ms) | 0.8 | 1.3 | 1.2 | 1.0 |
| V90-10 (ms) | 0.7 | 0.6 | 0.6 | 0.7 |
| $\epsilon'$ (PSBP) | 68.4 | 65.1 | 66.2 | 80.6 |

TABLE 6

Composition of Nematic Liquid crystal compositions

| | | NLC-D | NLC-E | NLC-F | NLC-G | NLC-H | NLC-S (Comparative Example) |
|---|---|---|---|---|---|---|---|
| 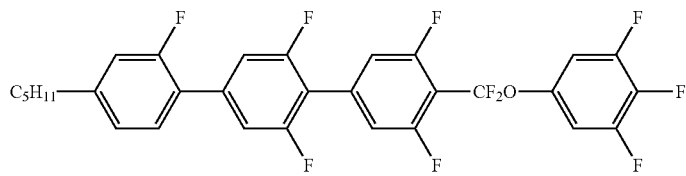 | (3-3) | 2.30 | 1.96 | 1.96 | 1.96 | 1.96 | 2.30 |
| 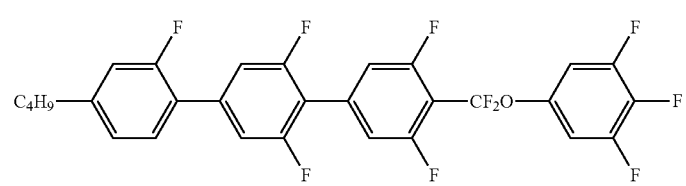 | (3-3) | 2.30 | 1.96 | 1.96 | 1.96 | 1.96 | 2.30 |

TABLE 6-continued

Composition of Nematic Liquid crystal compositions

| Structure | | NLC-D | NLC-E | NLC-F | NLC-G | NLC-H | NLC-S (Comparative Example) |
|---|---|---|---|---|---|---|---|
| C5H11—[2-F phenyl]—[2,3-F,F phenyl]—CF2O—[2,3-F,F phenyl]—[3,4-F,F phenyl]—F | (3-2) | — | 2.55 | 2.55 | 2.55 | 2.55 | 3.00 |
| C4H9—[2-F phenyl]—[2,3-F,F phenyl]—CF2O—[2,3-F,F phenyl]—[3,4-F,F phenyl]—F | (3-2) | — | 2.55 | 2.55 | 2.55 | 2.55 | 3.00 |
| C3H7—[2-F phenyl]—[2,3-F,F phenyl]—CF2O—[2,3-F,F phenyl]—[3,4-F,F phenyl]—F | (3-2) | — | 2.55 | 2.55 | 2.55 | 2.55 | 3.00 |
| C6H13—[2-F phenyl]—[2,3-F,F phenyl]—[2,3-F,F phenyl]—CF2O—[2,6-F,F phenyl]—CF3 | (3-3) | 3.75 | 3.19 | 3.19 | 3.19 | 3.19 | 3.75 |
| C5H11—[2-F phenyl]—[2,3-F,F phenyl]—[2,3-F,F phenyl]—CF2O—[2,6-F,F phenyl]—CF3 | (3-3) | 3.75 | 3.19 | 3.19 | 3.19 | 3.19 | 3.75 |
| C4H9—[2-F phenyl]—[2,3-F,F phenyl]—[2,3-F,F phenyl]—CF2O—[2,6-F,F phenyl]—CF3 | (3-3) | 3.75 | 3.19 | 3.19 | 3.19 | 3.19 | 3.75 |
| C3H7—[2-F phenyl]—[2,3-F,F phenyl]—[2,3-F,F phenyl]—CF2O—[2,6-F,F phenyl]—CF3 | (3-3) | 3.75 | 3.19 | 3.19 | 3.19 | 3.19 | 3.75 |
| C5H11—[1,3-dioxane]—[2,3-F,F phenyl]—CF2O—[2,3-F,F phenyl]—[3,4-F,F phenyl]—F | (7-2-5) | 15.00 | 12.75 | 12.75 | 12.75 | 12.75 | 15.00 |

TABLE 6-continued

Composition of Nematic Liquid crystal compositions

| | | NLC-D | NLC-E | NLC-F | NLC-G | NLC-H | NLC-S (Comparative Example) |
|---|---|---|---|---|---|---|---|
| [C4H9-dioxane-C6H2F2-CF2O-C6H2F-C6H2F2-F structure] | (7-2-5) | 15.00 | 12.75 | 12.75 | 12.75 | 12.75 | 15.00 |
| [C3H7-dioxane-C6H2F2-CF2O-C6H2F-C6H2F2-F structure] | (7-2-5) | 15.00 | 12.75 | 12.75 | 12.75 | 12.75 | 15.00 |
| [C5H11-dioxane-C6H2F-C6H2F-CF2O-C6H2F2-F structure] | (7-2-4) | 9.00 | 7.65 | 7.65 | 7.65 | 7.65 | 9.00 |
| [C4H9-dioxane-C6H2F-C6H2F-CF2O-C6H2F2-F structure] | (7-2-4) | 9.00 | 7.65 | 7.65 | 7.65 | 7.65 | 9.00 |
| [C3H7-dioxane-C6H2F-C6H2F-CF2O-C6H2F2-F structure] | (7-2-4) | 8.40 | 7.14 | 7.14 | 7.14 | 7.14 | 8.40 |
| [C4H9-C6H2F-C6H2F-CF2O-C6H2F-C6H2F-CF3 structure] | (1-1-3S) | | 15.00 | | | | — |
| [C3H7-C6H2F-C6H2F-CF2O-C6H2F-C6H2F-OCF3 structure] | (1-1-2S) | | 15.00 | | | | — |

TABLE 6-continued

Composition of Nematic Liquid crystal compositions

| | | NLC-D | NLC-E | NLC-F | NLC-G | NLC-H | NLC-S (Comparative Example) |
|---|---|---|---|---|---|---|---|
| [Structure: C$_5$H$_{11}$–(2-F phenyl)–(3-F, 5-F phenyl)–CF$_2$O–(2-F, 6-F phenyl)–(3-F phenyl)–CF$_3$] | (1-1-3T) | 9.00 | | | 15.00 | | — |
| [Structure: C$_3$H$_7$–(1,3-dioxane)–(3-F, 5-F phenyl)–CF$_2$O–(2-F, 6-F phenyl)–(3-F phenyl)–OCF$_3$] | (1-3-2S) | | | | | 15.00 | — |

Phase transition temperatures (° C.) of NLC-D to NLC-H and NLC-S were as shown in Table 7 below.

TABLE 7

N-I Transition Point of Nematic Liquid crystal compositions

| | NLC | | | | | |
|---|---|---|---|---|---|---|
| | NLC-D | NLC-E | NLC-F | NLC-G | NLC-H | NLC-S |
| N-I Transition Point (° C.) | 88.2-88.4 | 84.8-85.0 | 91.2-91.4 | 85.8-86.0 | 92.2-92.3 | 87.8 |

Example 14

Preparation of Chiral Liquid Crystal Composition (CLC)

Chiral liquid crystal compositions CLC-D to CLC-H and CLC-S were prepared by mixing the nematic liquid crystal compositions obtained in Example 13 with a chiral agent (CD1) shown below. Compositions and phase transition temperatures of the chiral liquid crystal compositions were as shown in Table 8 below. Moreover, the structure of CD1 in the table is the same as that described above.

TABLE 8

Composition and Phase Transition Point of Chiral Liquid crystal compositions

| | | CLC | | | | | |
|---|---|---|---|---|---|---|---|
| | | CLC-D | CLC-E | CLC-F | CLC-G | CLC-H | CLC-S |
| | | NLC Contained | | | | | |
| | | NLC-D | NLC-E | NLC-F | NLC-G | NLC-H | NLC-S |
| Composition (wt %) | NLC | 95.2 | 95.2 | 95.2 | 95.2 | 95.2 | 95.2 |
| | CD-1 | 4.8 | 4.8 | 4.8 | 4.8 | 4.8 | 4.8 |
| Phase Transition (° C.) | N*-BP | 79.0-79.3 | 77.2-77.4 | 83.1-83.3 | 77.7-77.9 | 83.3-83.5 | 79.8-80.1 |
| | BP-(BP + Iso) | 80.7 | — | 84.4 | 79.0 | — | 81.2 |
| | (BP + Iso)-Iso. | 81.0 | — | 84.7 | 79.4 | 85.7 | 81.6 |

Example 15

Preparation of Liquid Crystal Composition (MLC) being Mixture with Polymerizable Monomer Liquid crystal compositions MLC-D to MLC-H and MLC-S were prepared by heating and mixing, in an isotropic phase, a mixture of the chiral liquid crystal compositions (CLC) prepared in Example 14 with a polymerizable monomer. Compositions and phase transition points (° C.) of these liquid crystal compositions are shown in Table 9 below.

Moreover, LCA-12 is 1,4-di(4-(6-(acryloyloxy)dodecyloxy)benzoyloxy)-2-methylbenzene, and DMPA is 2,2'-dimethoxyphenylacetophenone and is a photopolymerization initiator.

15 with a polymerizable monomer was interposed between a comb-shaped electrode substrate having no alignment treatment applied thereon and an opposite glass substrate (with no electrode), and the resultant was heated to a blue phase.

In this state, a polymerization reaction was performed by irradiating the resultant with UV light (UV light intensity: 23 mWcm$^{-2}$ (365 nm)) for 1 minute. Thus, cells having polymer/liquid-crystal composite materials (PSBP-S) sandwiched therein were prepared (cell thickness: 7 to 9 μm). The thus obtained polymer/liquid-crystal composite material (PSBP-S) maintained the optically isotropic liquid crystal phase even when cooled to room temperature.

TABLE 9

Composition and Phase Transition Point of Mixtures of Monomers and Chiral Liquid crystal compositions

| | | MLC | | | | | |
|---|---|---|---|---|---|---|---|
| | | MLC-D | MLC-E | MLC-F | MLC-G | MLC-H | MLC-S |
| | | \multicolumn{6}{c}{CLC Contained} | | | | | |
| | | CLC-D | CLC-E | CLC-F | CLC-G | CLC-H | CLC-S |
| Composition (wt %) | CLC | 88.4 | 88.4 | 88.5 | 88.4 | 88.4 | 88.4 |
| | n-hexadecylacrylate | 6.2 | 6.2 | 6.2 | 6.2 | 6.2 | 6.2 |
| | LCA-12 | 5.0 | 5.0 | 5.0 | 5.0 | 5.0 | 5.0 |
| | DMPA | 0.4 | 0.4 | 0.4 | 0.4 | 0.4 | 0.4 |
| Phase Transition Heating (° C.) | N*-BP | 51.5-51.8 | 49.5-50.0 | 53.5-53.9 | 50.4-50.7 | 53.4-53.6 | 52.2-52.7 |
| | BP-(BP + Iso) | 53.8 | 54.7 | 58.4 | 55.2 | 59.0 | 53.7 |
| | (BP + Iso)-Iso. | 54.4 | 55.0 | 58.8 | 55.7 | 59.4 | 57.3 |
| Phase Transition Cooling (° C.) | Iso-BP | — | — | 57.6 | 54.5 | 57.9 | 55.7 |
| | Iso-(Iso + BP) | 52.1 | 51.0 | — | — | — | — |
| | BP-N* | 49.8 | 47.7 | 51.5 | 48.7 | 51.9 | 50.9 |

Example 16

Preparation of a Cell Having a Polymer/Liquid-Crystal Composite Material Sandwiched Therein The liquid crystal composition (MLC-D to MLC-H) being a mixture of the chiral liquid crystal composition obtained in Example 15 with a polymerizable monomer was interposed between a comb-shaped electrode substrate having no alignment treatment applied thereon and an opposite glass substrate (with no electrode), and the resultant was heated to a blue phase.

In this state, a polymerization reaction was performed by irradiating the resultant with UV light (UV light intensity: 23 mWcm$^{-2}$ (365 nm)) for 1 minute. Thus, cells having polymer/liquid-crystal composite materials (PSBP-D to PSBP-H) sandwiched therein were prepared (cell thickness: 7 to 9 μm). The resultant polymer/liquid-crystal composite materials (PSBP-D to PSBP-H) maintained the optically isotropic liquid crystal phase even when cooled to room temperature.

Comparative Example 2

Preparation of a Cell Having a Polymer/Liquid-Crystal Composite Material Sandwiched Therein The liquid crystal composition (MLC-S) being a mixture of the chiral liquid crystal composition obtained in Example

Example 17

Optical System Using Cell

The cell having the polymer/liquid-crystal composite material sandwiched therein as obtained in Example 16 and in Comparative Example 2 was set to the optical system shown in FIG. 2. Specifically, a white light source of a polarizing microscope (ECLIPSE LV100POL made by Nikon Corporation) was used as a light source 3, and the cell 5 having the polymer/liquid-crystal composite material sandwiched therein was set so that an incidence angle on the cell was perpendicular to the cell surface and a line direction of the comb-shaped electrode was 45° with respect to each of the polarizer 4 and the analyzer 6 polarizing plates (FIG. 2).

The relationship between applied voltage and transmittance of each of the polymer/liquid-crystal composite materials (PSBP-D to PSBP-H and PSBP-S) at room temperature was investigated using the optical system. Saturation voltage (Vmax), transmittance (%) during application of the saturation voltage, contrast ratio and response rate (ms) of the polymer/liquid-crystal composite materials (PSBP-D to PSBP-H and PSBP-S) sandwiched in the cell were as shown in Table 10. Moreover, the data of the response rate is that when the saturation voltage is applied and removed.

Furthermore, the permittivity ($\in$' (PSBP)) of the polymer/liquid-crystal composite materials (PSBP-D to PSBP-H and PSBP-S) was measured by the previously described method.

The permittivity (ϵ' (PSBP)) of the polymer/liquid-crystal composite materials (PSBP-D to PSBP-H and PSBP-S) was as shown in Table 10.

TABLE 10

Preparation Conditions and Physical Property Values of Polymer/Liquid Crystal Composite Materials

| | PSBP | | | | | PSBP-S (Comparative Example) |
|---|---|---|---|---|---|---|
| | PSBP-D | PSBP-E | PSBP-F | PSBP-G | PSBP-H | |
| | MLC Used | | | | | |
| | MLC-D | MLC-E | MLC-F | MLC-G | MLC-H | MLC-S |
| Polymerization Temperature (° C.) | 51.7 | 50.0 | 53.9 | 50.7 | 53.4 | 52.0 |
| Vmax (V) | 50.3 | 52.8 | 47.8 | 52.8 | 52.7 | 50.3 |
| Transmittance (%) During Application of Vmax | 89.7 | 89.4 | 89.3 | 89.9 | 88.4 | 90.0 |
| Contrast Ratio | 699.7 | 747.6 | 571.3 | 750.5 | 682.3 | 775.0 |
| V10-90 (ms) | 1.2 | 1.0 | 1.5 | 1.1 | 1.2 | 1.3 |
| V90-10 (ms) | 0.7 | 0.7 | 0.7 | 0.5 | 0.5 | 0.7 |
| ϵ' (PSBP) | 75.3 | 72.5 | 70.7 | 67.5 | 72.1 | 77.0 |

From Table 10, PSBP-D to PSBP-H have a saturation voltage (Vmax) ranging from 47.8 to 52.8 (V) and permittivity (ϵ' (PSBP)) ranging from 67.5 to 75.3. PSBP-S shown as the comparative example has a saturation voltage (Vmax) of 50.3 (V) and permittivity (ϵ' (PSBP)) of 77.0. From this result, it is known that although the saturation voltage of PSBP-D to PSBP-H is on the same level as that of PSBP-S, the permittivity of PSBP-D to PSBP-H is approximately 1.7 to 9.5 lower than that of PSBP-S. It is known that the compound (1) is a compound effective for reducing permittivity of a polymer/liquid-crystal composite material.

Examples of the applications of the invention include an optical device such as a display device using a polymer/liquid-crystal composite.

What is claimed is:

1. A liquid crystal composition, containing an achiral component (T) and a chiral agent (K), and exhibiting an optically isotropic liquid crystal phase, wherein the achiral component (T) comprises, as a first component, at least one compound (1) represented by formula (1),

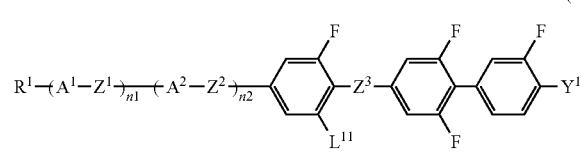

(1)

wherein in formula (1), $R^1$ is hydrogen, alkyl having 1 to 12 carbons, alkenyl having 2 to 12 carbons, alkynyl having 2 to 12 carbons, or alkoxy having 1 to 11 carbons;

$A^1$ is independently 1,3-dioxane-2,5-diyl, 1,4-phenylene, 3-fluoro-1,4-phenylene, 3,5-difluoro-1,4-phenylene or 3-fluoro-5-chloro-1,4-phenylene;

$Z^1$ is independently a single bond, or alkylene having 1 to 4 carbons;

$Z^3$ is —CF$_2$O—;

$L^{11}$ is hydrogen or fluorine;

$Y^1$ is fluorine, —CF$_3$ or —OCF$_3$; and n1 is 1;

wherein the chiral agent (K) comprises, as a chiral component, at least one compound (K6-6) represented by formula (K6-6),

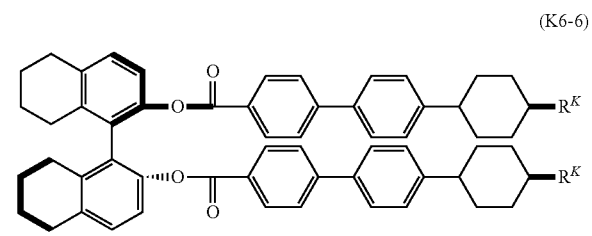

(K6-6)

wherein in formula (K6-6), each $R^K$ is independently alkyl having 3 to 10 carbons.

2. The liquid crystal composition of claim 1, wherein the achiral component (T) comprises at least one compound represented by any one of formulae (1-1) or (1-3),

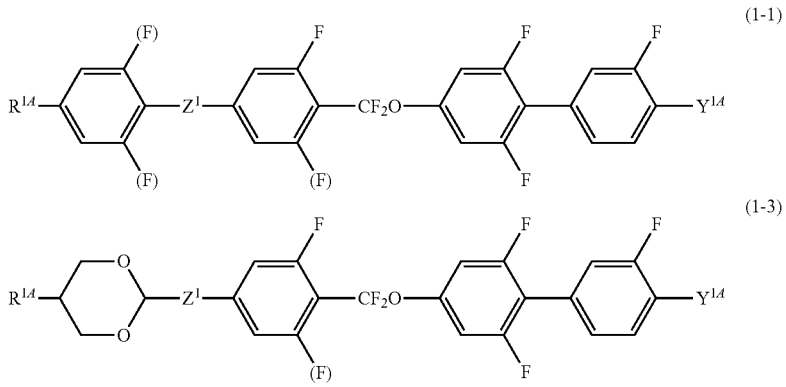

(1-1)

(1-3)

wherein in formulae (1-1) or (1-3), $R^{1A}$ is alkyl having 1 to 12 carbons or alkenyl having 2 to 12 carbons;

$Z^1$ is independently a single bond, or alkylene having 1 to 4 carbons;

$Y^{1A}$ is fluorine, —$OCF_3$ or —$CF_3$; and (F) is fluorine or hydrogen.

3. The liquid crystal composition according to claim 1, further comprising, as a second component of the achiral component (T), at least one selected from the group consisting of a compound (3) represented by formula (3) and a compound (7) represented by formula (7),

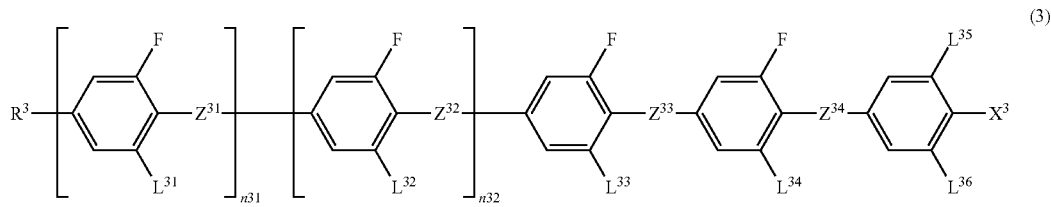

(3)

wherein in formula (3), $R^3$ is hydrogen, or alkyl having 1 to 12 carbons, wherein at least one —$CH_2$— in $R^3$ is optionally replaced with —O—, —S—, —COO— or —OCO—, at least one —$CH_2$—$CH_2$— in $R^3$ is optionally replaced with —CH=CH—, —CF=CF— or —C≡C—, at least one hydrogen in $R^3$ is optionally replaced with fluorine or chlorine, and in $R^3$, —O— and —CH=CH— are not adjacent to each other and —CO— and —CH=CH— are not adjacent to each other;

$Z^{31}$, $Z^{32}$, $Z^{33}$ and $Z^{34}$ are each independently a single bond, or alkylene having 1 to 4 carbons, wherein at least one —$CH_2$— in the alkylene is optionally replaced with —O—, —COO— or —$CF_2O$—;

$L^{31}$, $L^{32}$, $L^{33}$, $L^{34}$, $L^{35}$ and $L^{36}$ are each independently hydrogen or fluorine;

$X^3$ is hydrogen, halogen, —$SF_5$, or alkyl having 1 to 10 carbons, wherein at least one —$CH_2$— in $X^3$ is optionally replaced with —O—, —S—, —COO— or —OCO—, at least one —$CH_2$—$CH_2$— in $X^3$ is optionally replaced with —CH=CH—, —CF=CF— or —C≡C—, at least one hydrogen in $X^3$ is optionally replaced with fluorine or chlorine, and in $X^3$, —O— and —CH=CH— are not adjacent to each other and —CO— and —CH=CH— are not adjacent to each other;

n31 and n32 are each independently 0 or 1; and when $Z^{33}$ is —$CF_2O$— or —COO—, $Z^{34}$ is a single bond and $L^{34}$ is fluorine, both $L^{35}$ and $L^{36}$ are fluorine;

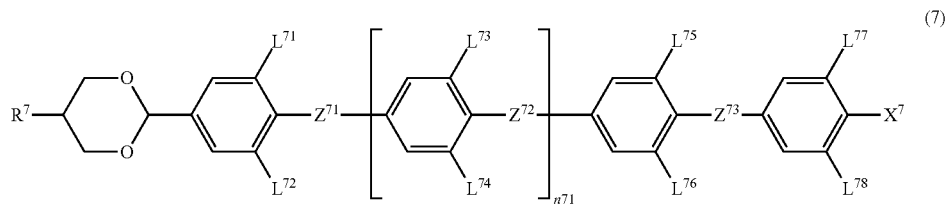

(7)

and in formula (7), $R^7$ is hydrogen, or alkyl having 1 to 12 carbons, wherein at least one —$CH_2$— in $R^7$ is optionally replaced with —O—, —S—, —COO— or —OCO—, at least one —$CH_2$—$CH_2$— in $R^7$ is optionally replaced with —CH=CH—, —CF=CF— or —C≡C—, at least one hydrogen in $R^7$ is optionally replaced with fluorine or chlorine, and in $R^7$, —O— and —CH=CH— are not adjacent to each other and —CO— and —CH=CH— are not adjacent to each other;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond, —COO— or —$CF_2O$—;

$X^7$ is hydrogen, halogen, —$SF_5$, or alkyl having 1 to 10 carbons, wherein at least one —$CH_2$— in $X^7$ is optionally replaced with —O—, —S—, —COO— or —OCO—, at least one —$CH_2$—$CH_2$— in $X^7$ is optionally replaced with —CH=CH—, —CF=CF— or —C≡C—, at least one hydrogen in $X^7$ is optionally replaced with fluorine or chlorine, and in $X^7$, —O— and —CH=CH— are not adjacent to each other and —CO— and —CH=CH— are not adjacent to each other;

n71 is 0 or 1;

when n71=1, $Z^{72}$ is —$CF_2O$— or —COO—, $Z^{73}$ is a single bond, and both $L^{75}$ and $L^{76}$ are fluorine, both $L^{77}$ and $L^{78}$ are fluorine; and when n71=0, $Z^{71}$ is —$CF_2O$— or —COO—, $Z^{73}$ is a single bond, and both $L^{75}$ and $L^{76}$ are fluorine, both $L^{77}$ and $L^{78}$ are fluorine.

4. The liquid crystal composition of claim 3, wherein the compound (3) is a compound represented by any one of formulae (3-1) to (3-3), (3-1)
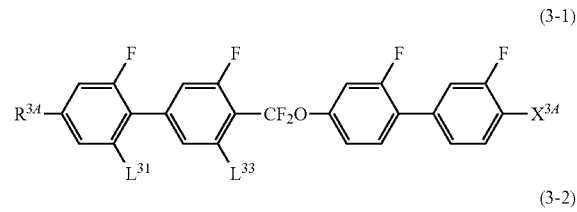

(3-2)
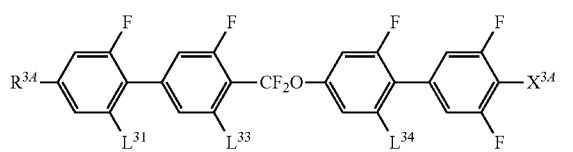

(3-3)
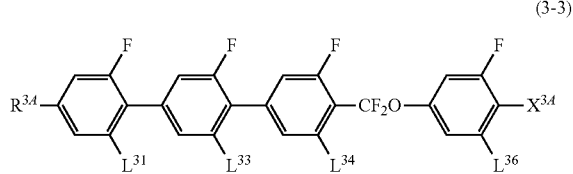

wherein in formulae (3-1) to (3-3), each $R^{3A}$ is independently alkyl having 1 to 12 carbons, alkenyl having 2 to 12 carbons, or alkoxy having 1 to 11 carbons;

$L^{31}$, $L^{33}$, $L^{34}$ and $L^{36}$ are each independently hydrogen or fluorine; and $X^{3A}$ is fluorine, chlorine, —$CF_3$ or —$OCF_3$.

5. The liquid crystal composition of claim 3, wherein the compound (7) is a compound represented by any one of formulae (7-1) to (7-8), (7-1)
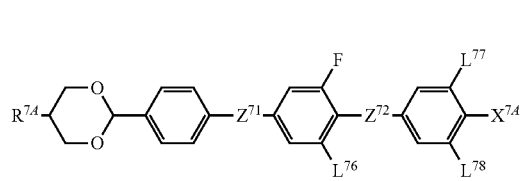

(7-2)
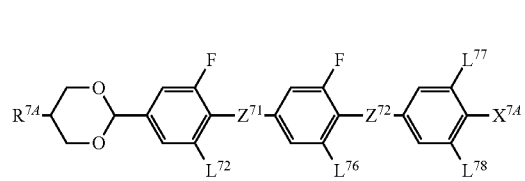

(7-3)
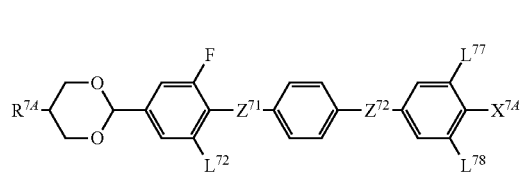

(7-4)
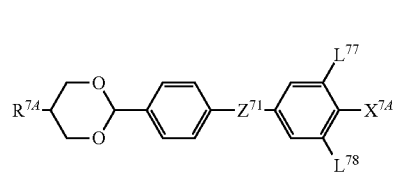

(7-5)
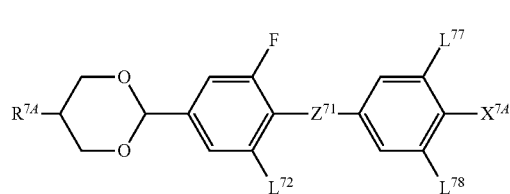

(7-6)
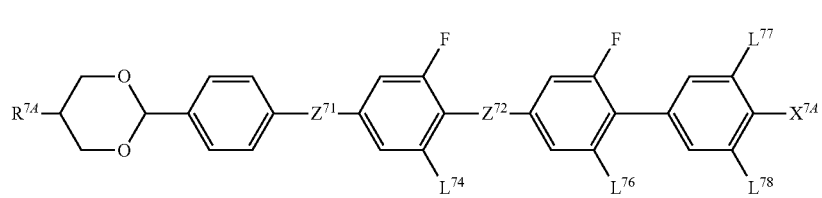

(7-7)

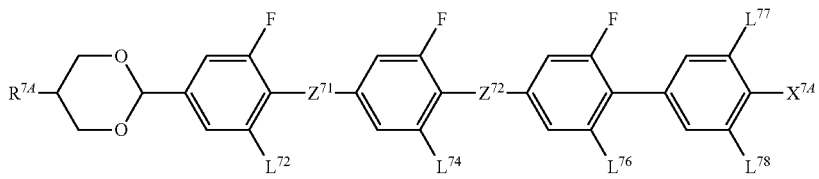

(7-8)

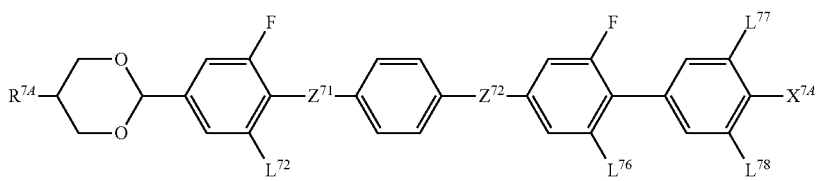

wherein in formulae (7-1) to (7-8), each $R^{7A}$ is independently hydrogen, alkyl having 1 to 12 carbons, alkenyl having 2 to 12 carbons, or alkoxy having 1 to 11 carbons;

$L^{72}$, $L^{74}$, $L^{76}$, $L^{77}$ and $L^{78}$ are each independently hydrogen or fluorine;

each $X^{7A}$ is independently fluorine, chlorine, —$CF_3$ or —$OCF_3$;

$Z^{71}$ and $Z^{72}$ are each independently a single bond, —COO— or —$CF_2O$—, wherein at least one of $Z^{71}$ and $Z^{72}$ is —COO— or —$CF_2O$—; and when $L^{76}$ is fluorine, both $L^{77}$ and $L^{78}$ are fluorine.

6. The liquid crystal composition of claim 3, wherein the compound (7) is a compound represented by any one of formulae (7-2-1) to (7-2-7), (7-2-1)

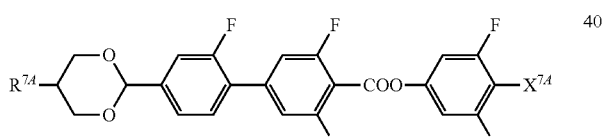

(7-2-2)

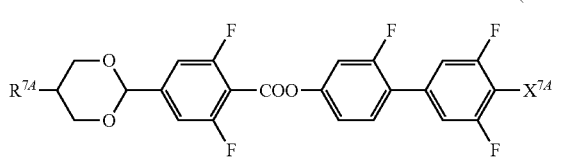

(7-2-3)

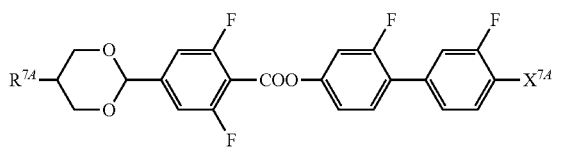

(7-2-4)

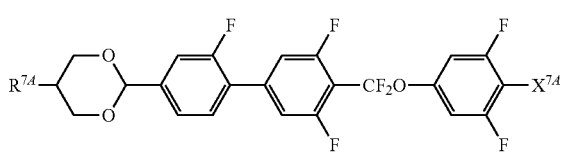

(7-2-5)

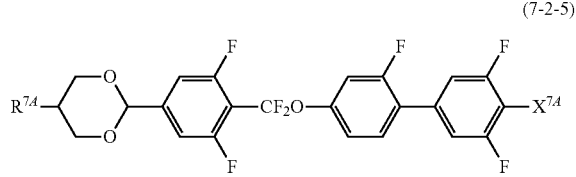

(7-2-6)

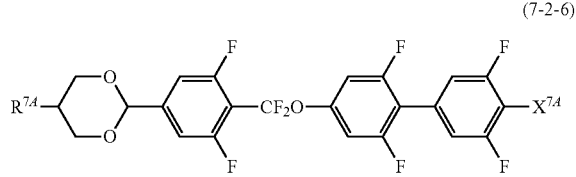

(7-2-7)

wherein in formulae (7-2-1) to (7-2-7), each $R^{7A}$ is independently alkyl having 1 to 12 carbons, alkenyl having 2 to 12 carbons, or alkoxy having 1 to 11 carbons; and $X^{7A}$ is fluorine, chlorine, —$CF_3$ or —$OCF_3$.

7. The liquid crystal composition of claim 3, containing a total of 10 to 30 wt % of the compound (1), a total of 20 to 60 wt % of the compound (3) and a total of 30 to 70 wt % of the compound (7), based on a total weight of the achiral component (T).

8. The liquid crystal composition of claim 3, further comprising, as a third component of the achiral component (T), at least one selected from the group consisting of a compound (4) represented by formula (4) and a compound (2) represented by formula (2),

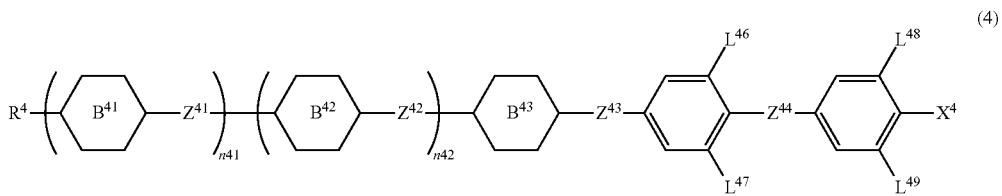

wherein in formula (4),
- $R^4$ is alkyl having 1 to 12 carbons, alkenyl having 2 to 12 carbons, or alkoxy having 1 to 11 carbons;
- $B^{41}$, $B^{42}$ and $B^{43}$ are each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2,5-diyl, wherein at least one of $B^{41}$, $B^{42}$ and $B^{43}$ is 1,4-cyclohexylene, 1,4-phenylene or pyrimidine-2,5-diyl;
- $Z^{41}$, $Z^{42}$, $Z^{43}$ and $Z^{44}$ are each independently a single bond, ethylene, —COO—, —OCO—, —CF$_2$O— or —OCF$_2$—;
- $L^{46}$, $L^{47}$, $L^{48}$ and $L^{49}$ are each independently hydrogen or fluorine;
- $X^4$ is fluorine, chlorine, —CF$_3$ or —OCF$_3$;
- n41 and n42 are each independently 0 or 1; and
- when $Z^{43}$ is —CF$_2$O— or —COO—, $Z^{44}$ is a single bond and both $L^{46}$ and $L^{47}$ are fluorine, both $L^{48}$ and $L^{49}$ are fluorine;

and in formula (2),
- $R^2$ is hydrogen, or alkyl having 1 to 12 carbons, wherein at least one —CH$_2$— in $R^2$ is optionally replaced with —O—, —S—, —COO—, —OCO—, —CH=CH—, —CF=CF— or —C≡C—, at least one hydrogen in $R^2$ is optionally replaced with halogen, or alkyl having 1 to 3 carbons, and in $R^2$, —O— and —CH=CH— are not adjacent to each other and —CO— and —CH=CH— are not adjacent to each other;
- $A^{21}$, $A^{22}$, $A^{23}$ and $A^{24}$ are each independently 1,4-cyclohexylene, 1,3-dioxane-2,5-diyl, 1,4-phenylene, 1,4-phenylene in which one or two hydrogens are replaced with fluorine, 1,4-phenylene in which two hydrogens are replaced with fluorine and chlorine respectively, pyridine-2,5-diyl, or pyrimidine-2,5-diyl;
- $Z^{21}$, $Z^{22}$, $Z^{23}$, $Z^{24}$, $Z^{25}$ and $Z^{26}$ are each independently a single bond, or alkylene having 1 to 4 carbons, wherein at least one —CH$_2$— in the alkylene is optionally replaced with —O—, —COO— or —CF$_2$O—;
- $L^{21}$, $L^{22}$ and $L^{23}$ are each independently hydrogen or fluorine;
- $X^2$ is fluorine, chlorine, —CF$_3$ or —OCF$_3$;
- n21, n22, n23 and n24 are each independently 0 or 1, and $1 \leq n21+n22+n23+n24 \leq 2$; and
- when $Z^{26}$ is a single bond and $L^{21}$ is fluorine, both $L^{22}$ and $L^{23}$ are fluorine.

9. The liquid crystal composition of claim 8, wherein the compound (4) is a compound represented by any one of formulae (4-1) to (4-10),

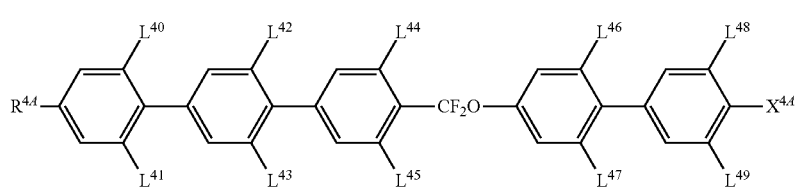
(4-1)
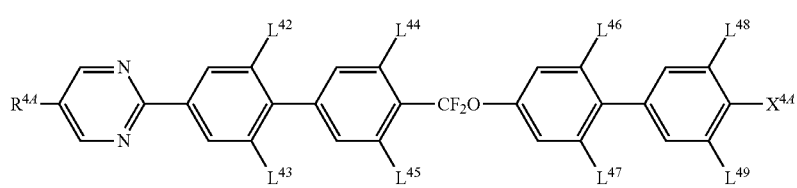
(4-2)
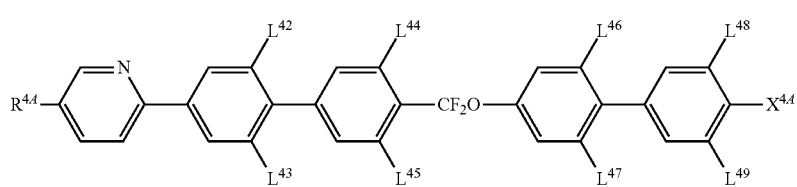
(4-3)
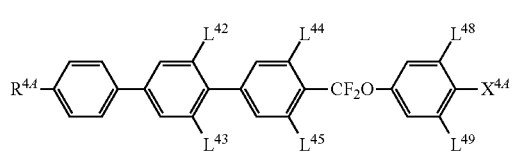
(4-4)
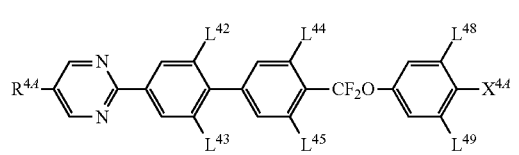
(4-5)
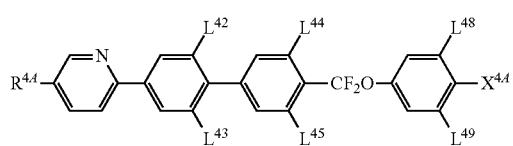
(4-6)
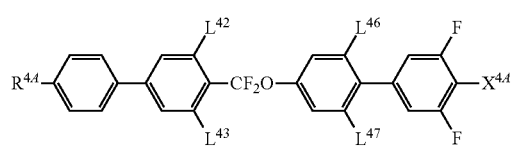
(4-7)
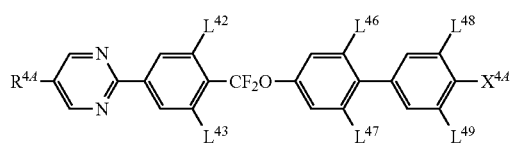
(4-8)
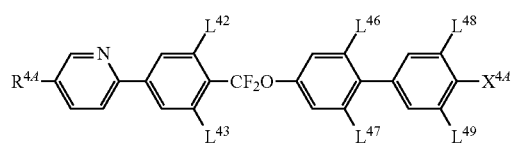
(4-9)
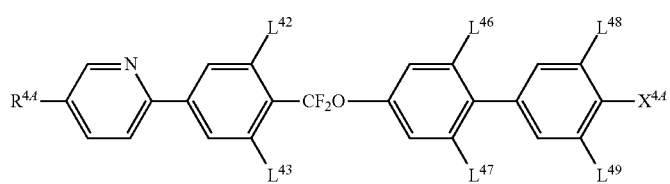
(4-10)
wherein in formulae (4-1) to (4-10),
each $R^{4A}$ is independently alkyl having 1 to 12 carbons, alkenyl having 2 to 12 carbons, or alkoxy having 1 to 11 carbons;
$X^{4A}$ is fluorine, chlorine, —$CF_3$ or —$OCF_3$; and
$L^{40}$ to $L^{49}$ are each independently hydrogen or fluorine, wherein when both $L^{46}$ and $L^{47}$ are fluorine, both $L^{48}$ and $L^{49}$ are fluorine.

10. The liquid crystal composition of claim 8, wherein the compound (2) is a compound represented by any one of formulae (2-1-1-2), (2-1-2-1), (2-1-3-1), (2-1-3-2), (2-1-4-2) and (2-1-4-3), 13. A polymer/liquid-crystal composite material, obtained by polymerizing the mixture of claim 12, for use in a device driven in an optically isotropic liquid crystal phase.

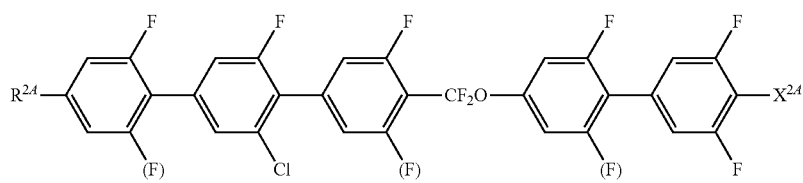
(2-1-1-2)

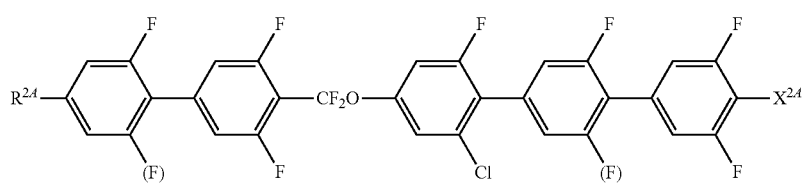
(2-1-2-1)

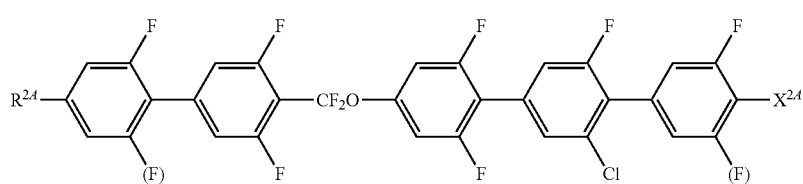
(2-1-3-1)

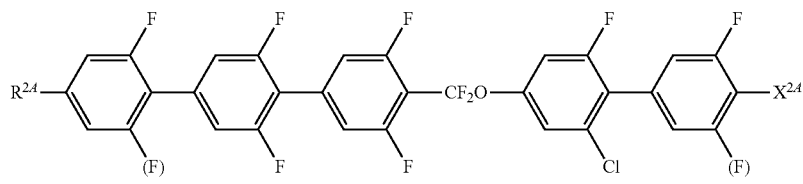
(2-1-3-2)

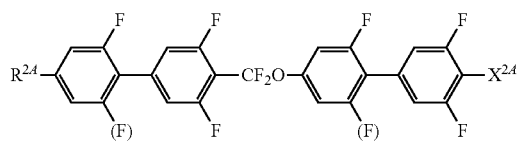
(2-1-4-2)

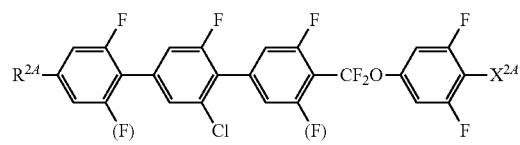
(2-1-4-3)

wherein in formulae (2-1-1-2), (2-1-2-1), (2-1-3-1), (2-1-3-2), (2-1-4-2) and (2-1-4-3), each $R^{2A}$ is independently alkyl having 1 to 12 carbons, alkenyl having 2 to 12 carbons, or alkoxy having 1 to 11 carbons;

each (F) is independently hydrogen or fluorine; and $X^{2A}$ is fluorine, chlorine, —$CF_3$ or —$OCF_3$.

11. The liquid crystal composition of claim 1, exhibiting a chiral nematic phase at any temperature in a range of −20 to 70° C., and having a helical pitch of 700 nm or less within at least a part of the temperature range.

12. A mixture, comprising the liquid crystal composition of claim 1 and a polymerizable monomer.

14. An optical device, comprising two substrates in which electrodes are disposed on one or both thereof, a liquid crystal medium disposed between the substrates, and an electric field applying means for applying an electric field to the liquid crystal medium through the electrodes, wherein the liquid crystal medium is the liquid crystal composition of claim 1.

15. An optical device, comprising two substrates in which electrodes are disposed on one or both thereof, a liquid crystal medium disposed between the substrates, and an electric field applying means for applying an electric field to the liquid crystal medium through the electrodes, wherein the liquid crystal medium is the polymer/liquid-crystal composite material of claim 13.

* * * * *